United States Patent
Koh et al.

(10) Patent No.: US 9,228,218 B2
(45) Date of Patent: Jan. 5, 2016

(54) EXPRESSION VECTOR FOR ANIMAL CELLS INCLUDING CSP-B 5'-SAR FACTOR AND METHOD FOR PRODUCING RECOMBINANT PROTEINS USING SAME

(75) Inventors: Yeo-Wook Koh, Yongin-si (KR); Sang-Yong Lee, Yongin-si (KR); Su-Yon Kim, Yongin-si (KR); Seung-Kee Moon, Yongin-si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 0 days.

(21) Appl. No.: 14/125,705

(22) PCT Filed: May 21, 2012

(86) PCT No.: PCT/KR2012/003995
§ 371 (c)(1),
(2), (4) Date: Dec. 12, 2013

(87) PCT Pub. No.: WO2012/173344
PCT Pub. Date: Dec. 20, 2012

(65) Prior Publication Data
US 2014/0093914 A1    Apr. 3, 2014

(30) Foreign Application Priority Data

Jun. 13, 2011  (KR) .......................... 10-2011-0056685

(51) Int. Cl.
| | |
|---|---|
| *C12N 15/85* | (2006.01) |
| *C12N 9/64* | (2006.01) |
| *C12P 21/00* | (2006.01) |
| *C12N 9/48* | (2006.01) |
| *C12N 9/50* | (2006.01) |
| *C12P 21/04* | (2006.01) |
| *C12P 21/06* | (2006.01) |
| *C07H 21/04* | (2006.01) |

(52) U.S. Cl.
CPC ............... *C12P 21/00* (2013.01); *C12N 9/6408* (2013.01); *C12N 15/85* (2013.01); *C12N 2830/46* (2013.01); *C12N 2830/85* (2013.01)

(58) Field of Classification Search
None
See application file for complete search history.

(56) References Cited

U.S. PATENT DOCUMENTS 7,422,874 B2 *   9/2008   Kim et al. .................... 435/69.1

OTHER PUBLICATIONS

Kim et al., "Improved recombinant gene expression in CHO cells using matrix attachment regions" 107 Journal of Biotechnology 95-105 (2004).*
Kim et al., "Efficient Selection of Stable Chinese Hamster Ovary (CHO) Cell Lines for Expression of Recombinant Proteins by Using Human Interferon β SAR Element" 21 Biotechnology Progress 933-937 (2005).*
Hanson et al., "A-T-rich scaffold attachment regions flank the hematopoietic serine protease genes clustered on chromosome 14q11.2," Blood. 79(3):610-8 (1992).
Thompson et al., "Scaffold attachment regions stimulate HSP70.1 expression in mouse preimplantation embryos but not in differentiated tissues," Mol Cell Biol. 14(7):4694-703 (1994).
International Search Report for International Patent Application No. PCT/KR2012/003995, mailed Nov. 29, 2012 (2 pages).

* cited by examiner

*Primary Examiner* — Nancy J Leith
(74) *Attorney, Agent, or Firm* — Clark & Elbing LLP; Susan M. Michaud

(57) ABSTRACT

The present invention relates to an expression vector for animal cells, comprising: (a) CSP-B (Cytotoxic Serine Protease-B) 5'-SAR (Scaffold or Matrix Attachment Region); (b) a promoter operable in animal cells; and (c) a polyadenylation sequence, and to a method for producing recombinant proteins using same. The vector of the present invention includes CSP-B 5'-SAR, and thus has the effect of overcoming the inhibition of gene expression according to the position of a foreign gene introduced into an animal cell, and significantly improving the expression rate of a target protein. The vector of the present invention effectively expresses recombinant proteins for drugs or antibodies in animal cells. The vector of the present invention and the method for producing recombinant proteins using same may be very usefully applied to the industrial mass production of drugs.

6 Claims, 23 Drawing Sheets

SEQUENCE LISTING

<160> NUMBER OF SEQ ID NOS: 65

<210> SEQ ID NO 1
<211> LENGTH: 12452

```
<212> TYPE: DNA
<213> ORGANISM: Artificial Sequence
<220> FEATURE:
<223> OTHER INFORMATION: pCLS09G1f1 vector
<220> FEATURE:
<221> NAME/KEY: promoter
<222> LOCATION: (4140)..(4834)
<220> FEATURE:
<221> NAME/KEY: gene
<222> LOCATION: (4937)..(8164)
<220> FEATURE:
<221> NAME/KEY: gene
<222> LOCATION: (8216)..(8418)
<220> FEATURE:
<221> NAME/KEY: gene
<222> LOCATION: (8711)..(11139)

<400> SEQUENCE: 1
cacgtagtgg gccatcgccc tgatagacgg ttttcgccc tttgacgttg gagtccacgt      60
tctttaatag tggactcttg ttccaaactg gaacaacact caaccctatc tcggtctatt    120
cttttgattt ataagggatt ttggggattt cggcctattg gttaaaaaat gagctgattt    180
aacaaaaatt taacgcgaat taattctgtg gaatgtgtgt cagttagggt gtggaaagtc    240
cccaggctcc ccagcaggca gaagtatgca aagcatgcat ctcaattagt cagcaaccag    300
gtgtggaaag tccccaggct ccccagcagg cagaagtatg caaagcatgc atctcaatta    360
gtcagcaacc atagtcccgc ccctaactcc gcccatcccg ccctaactc cgcccagttc    420
cgcccattct ccgccccatg gctgactaat tttttttatt tatgcagagg ccgaggccgc    480
ctctgcctct gagctattcc agaagtagtg aggaggcttt tttggaggcc taggcttttg    540
caaaaagctc ccgggagctt gtatatccat tttcggatct gatcaagaga caggatgagg    600
atcgtttcgc atgattgaac aagatggatt gcacgcaggt tctccggccg cttgggtgga    660
gaggctattc ggctatgact gggcacaaca gacaatcggc tgctctgatg ccgccgtgtt    720
ccggctgtca gcgcaggggc gcccggttct ttttgtcaag accgacctgt ccggtgccct    780
gaatgaactg caggacgagg cagcgcggct atcgtggctg gccacgacgg gcgttccttg    840
cgcagctgtg ctcgacgttg tcactgaagc gggaagggac tggctgctat tgggcgaagt    900
gccggggcag gatctcctgt catctcacct tgctcctgcc gagaaagtat ccatcatggc    960
tgatgcaatg cggcggctgc atacgcttga tccggctacc tgcccattcg accaccaagc   1020
gaaacatcgc atcgagcgag cacgtactcg gatggaagcc ggtcttgtcg atcaggatga   1080
tctggacgaa gagcatcagg ggctcgcgcc agccgaactg ttcgccaggc tcaaggcgcg   1140
catgcccgac ggcgaggatc tcgtcgtgac ccatggcgat gcctgcttgc cgaatatcat   1200
ggtggaaaat ggccgctttt ctggattcat cgactgtggc cggctgggtg tggcggaccg   1260
ctatcaggac atagcgttgg ctacccgtga tattgctgaa gagcttggcg gcgaatgggc   1320
tgaccgcttc ctcgtgcttt acggtatcgc cgctcccgat tcgcagcgca tcgccttcta   1380
tcgccttctt gacgagttct tctgagcggg actctgggt tcgcgaaatg accgaccaag   1440
cgacgcccaa cctgccatca cgagatttcg attccaccgc cgccttctat gaaaggttgg   1500
gcttcggaat cgttttccgg gacgccggct ggatgatcct ccagcgcggg gatctcatgc   1560
tggagttctt cgcccacccc aacttgttta ttgcagctta atggttac aaataaagca    1620
atagcatcac aaatttcaca aataaagcat ttttttcact gcattctagt tgtggtttgt   1680
ccaaactcat caatgtatct tatcatgtct gtataccgtc gacctctagc tagagcttgg   1740
cgtaatcatg gtcatagctg tttcctgtgt gaaattgtta tccgctcaca attccacaca   1800
```

```
acatacgagc cggaagcata aagtgtaaag cctggggtgc ctaatgagtg agctaactca    1860
cattaattgc gttgcgctca ctgcccgctt tccagtcggg aaacctgtcg tgccagctgc    1920
attaatgaat cggccaacgc gcggggagag gcggtttgcg tattgggcgc tcttccgctt    1980
cctcgctcac tgactcgctg cgctcggtcg ttcggctgcg gcgagcggta tcagctcact    2040
caaaggcggt aatacggtta ccacagaat cagggataa cgcaggaaag aacatgtgag    2100
caaaaggcca gcaaaaggcc aggaaccgta aaaaggccgc gttgctggcg ttttccata    2160 ggctccgccc ccctgacgag catcacaaaa atcgacgctc aagtcagagg tggcgaaacc    2220
cgacaggact ataaagatac caggcgtttc ccccctggaag ctcccctcgtg cgctctcctg    2280 ttccgaccct gccgcttacc ggatacctgt ccgcctttct cccttcggga agcgtggcgc    2340
tttctcaatg ctcacgctgt aggtatctca gttcggtgta ggtcgttcgc tccaagctgg    2400
gctgtgtgca cgaaccccccc gttcagcccg accgctgcgc cttatccggt aactatcgtc    2460
ttgagtccaa cccggtaaga cacgacttat cgccactggc agcagccact ggtaacagga    2520
ttagcagagc gaggtatgta ggcggtgcta cagagttctt gaagtggtgg cctaactacg    2580
gctacactag aaggacagta tttggtatct gcgctctgct gaagccagtt accttcggaa    2640
aaagagttgg tagctcttga tccggcaaac aaaccaccgc tggtagcggt ggtttttttg    2700
tttgcaagca gcagattacg cgcagaaaaa aaggatctca agaagatcct ttgatctttt    2760
ctacggggtc tgacgctcag tggaacgaaa actcacgtta agggattttg gtcatgagat    2820
tatcaaaaag gatcttcacc tagatccttt taaattaaaa atgaagtttt aaatcaatct    2880
aaagtatata tgagtaaact tggtctgaca gttaccaatg cttaatcagt gaggcaccta    2940
tctcagcgat ctgtctattt cgttcatcca tagttgcctg actccccgtc gtgtagataa    3000
ctacgatacg ggagggctta ccatctggcc ccagtgctgc aatgataccg cgagacccac    3060
gctcaccggc tccagattta tcagcaataa accagccagc cggaagggcc gagcgcagaa    3120
gtggtcctgc aactttatcc gcctccatcc agtctattaa ttgttgccgg gaagctagag    3180
taagtagttc gccagttaat agtttgcgca acgttgttgc cattgctaca ggcatcgtgg    3240
tgtcacgctc gtcgtttggt atggcttcat tcagctccgg ttcccaacga tcaaggcgag    3300
ttacatgatc ccccatgttg tgcaaaaaag cggttagctc cttcggtcct ccgatcgttg    3360
tcagaagtaa gttggccgca gtgttatcac tcatggttat ggcagcactg cataattctc    3420
ttactgtcat gccatccgta agatgctttt ctgtgactgg tgagtactca accaagtcat    3480
tctgagaata gtgtatgcgg cgaccgagtt gctcttgccc ggcgtcaata cgggataata    3540
ccgcgccaca tagcagaact ttaaaagtgc tcatcattgg aaaacgttct cggggcgaa    3600 aactctcaag gatcttaccg ctgttgagat ccagttcgat gtaacccact cgtgcaccca    3660
actgatcttc agcatctttt actttcacca gcgtttctgg gtgagcaaaa acaggaaggc    3720
aaaatgccgc aaaaaaggga ataagggcga cacggaaatg ttgaatactc atactcttcc    3780 ttttttcaata ttattgaagc atttatcagg gttattgtct catgagcgga tacatatttg    3840
aatgtattta gaaaaataaa caaatagggg ttccgcgcac atttccccga aaagtgccac    3900
ctgacgtcga cggatcggga gatctcccga tcccctatgg tcgactctca gtacaatctg    3960
ctctgatgcc gcatagttaa gccagtatct gctccctgct tgtgtgttgg aggtcgctga    4020
gtagtgcgcg agcaaaattt aagctacaac aaggcaaggc ttgaccgaca attgcatgaa    4080
gaatctgctt agggttaggc gttttgcgct gcttcgcgat gtacgggcca gatatacgcg    4140
ttgacattga ttattgacta gttattaata gtaatcaatt acgggtcat tagttcatag    4200
```

```
cccatatatg gagttccgcg ttacataact tacggtaaat ggcccgcctg gctgaccgcc   4260
caacgacccc cgcccattga cgtcaataat gacgtatgtt cccatagtaa cgccaatagg   4320
gactttccat tgacgtcaat gggtggagta tttacggtaa actgcccact tggcagtaca   4380
tcaagtgtat catatgccaa gtacgccccc tattgacgtc aatgacggta atggcccgc    4440 ctggcattat gcccagtaca tgaccttatg ggactttcct acttggcagt acatctacgt   4500
attagtcatc gctattacca tggtgatgcg gttttggcag tacatcaatg ggcgtggata   4560
gcggtttgac tcacggggat ttccaagtct caccccatt gacgtcaatg ggagtttgtt    4620
ttggcaccaa aatcaacggg actttccaaa atgtcgtaac aactccgccc cattgacgca   4680
aatgggcggt aggcgtgtac ggtgggaggt ctatataagc agagctcgtt tagtgaaccg   4740
tcagatcgcc tggagacgcc atccacgctg ttttgacctc catagaagac accgggaccg   4800
atccagcctc cggactctag aggatcgaac ccttaagctt ctcgcgcaac ctattttccc   4860
ctcgaacact ttttaagccg tagataaaca ggctgggaca cttcacatga gcgaaaaata   4920
catcgtcacc tgggacatgt tgcagatcca tgcacgtaaa ctcgcaagcc gactgatgcc   4980
ttctgaacaa tggaaaggca ttattgccgt aagccgtggc ggtctggtac cggtgggtga   5040
agaccagaaa cagcacctcg aactgagccg cgatattgcc cagcgtttca acgcgctgta   5100
tggcgagatc gatcccgtcg ttttacaacg tcgtgactgg gaaaaccctg gcgttaccca   5160
acttaatcgc cttgcagcac atcccccttt cgccagctgg cgtaatagcg aagaggcccg   5220
caccgatcgc ccttcccaac agttgcgcag cctgaatggc gaatggcgct ttgcctggtt   5280
tccggcacca gaagcggtgc cggaaagctg gctggagtgc gatcttcctg aggccgatac   5340
tgtcgtcgtc ccctcaaact ggcagatgca cggttacgat gcgcccatct acaccaacgt   5400
gacctatccc attacggtca atccgccgtt tgttcccacg gagaatccga cggggttgtta   5460 ctcgctcaca tttaatgttg atgaaagctg gctacaggaa ggccagacgc gaattatttt   5520
tgatggcgtt aactcggcgt ttcatctgtg gtgcaacggg cgctgggtcg gttacggcca   5580
ggacagtcgt ttgccgtctg aatttgacct gagcgcattt ttacgcgccg gagaaaaccg   5640
cctcgcggtg atggtgctgc gctggagtga cggcagttat ctggaagatc aggatatgtg   5700
gcggatgagc ggcatttttcc gtgacgtctc gttgctgcat aaaccgacta cacaaatcag   5760
cgatttccat gttgccactc gctttaatga tgatttcagc cgcgctgtac tggaggctga   5820
agttcagatg tgcggcgagt tgcgtgacta cctacgggta acagtttctt tatggcaggg   5880
tgaaacgcag tcgccagcg gcaccgcgcc tttcggcggt gaaattatcg atgagcgtgg   5940
tggttatgcc gatcgcgtca cactacgtct gaacgtcgaa aacccgaaac tgtggagcgc   6000
cgaaatcccg aatctctatc gtgcggtggt tgaactgcac accgccgacg gcacgctgat   6060
tgaagcagaa gcctgcgatg tcggtttccg cgaggtgcgg attgaaaatg gtctgctgct   6120
gctgaacggc aagccgttgc tgattcgagg cgttaaccgt cacagcatc atcctctgca    6180 tggtcaggtc atggatgagc agacgatggt gcaggatatc ctgctgatga agcagaacaa   6240
ctttaacgcc gtgcgctgtt cgcattatcc gaaccatccg ctgtggtaca cgctgtgcga   6300
ccgctacggc ctgtatgtgg tggatgaagc caatattgaa acccacgca tggtgccaat    6360 gaatcgtctg accgatgatc cgcgctggct accggcgatg agcgaacgcg taacgcgaat   6420
ggtgcagcgc gatcgtaatc acccgagtgt gatcatctgg tcgctgggga atgaatcagg   6480
ccacggcgct aatcacgacg cgctgtatcg ctggatcaaa tctgtcgatc cttcccgccc   6540
```

```
ggtgcagtat gaaggcggcg gagccgacac cacggccacc gatattattt gcccgatgta      6600
cgcgcgcgtg gatgaagacc agcccttccc ggctgtgccg aaatggtcca tcaaaaaatg      6660
gctttcgcta cctggagaga cgcgcccgct gatcctttgc gaatacgccc acgcgatggg      6720
taacagtctt ggcggtttcg ctaaatactg gcaggcgttt cgtcagtatc cccgtttaca      6780
gggcggcttc gtctgggact gggtggatca gtcgctgatt aaatatgatg aaaacggcaa      6840
cccgtggtcg gcttacggcg gtgattttgg cgatacgccg aacgatcgcc agttctgtat      6900
gaacggtctg gtctttgccg accgcacgcc gcatccagcg ctgacggaag caaaacacca      6960
gcagcagttt ttccagttcc gtttatccgg gcaaaccatc gaagtgacca gcgaatacct      7020
gttccgtcat agcgataacg agctcctgca ctggatggtg gcgctggatg gtaagccgct      7080
ggcaagcggt gaagtgcctc tggatgtcgc tccacaaggt aaacagttga ttgaactgcc      7140
tgaactaccg cagccggaga cgccgggca actctggctc acagtacgcg tagtgcaacc      7200
gaacgcgacc gcatggtcag aagccgggca catcagcgcc tggcagcagt ggcgtctggc      7260
ggaaaacctc agtgtgacgc tccccgccgc gtcccacgcc atcccgcatc tgaccaccag      7320
cgaaatggat ttttgcatcg agctgggtaa taagcgttgg caatttaacc gccagtcagg      7380 ctttcttttca cagatgtgga ttggcgataa aaaacaactg ctgacgccgc tgcgcgatca      7440
gttcacccgt gcaccgctgg ataacgacat tggcgtaagt gaagcgaccc gcattgaccc      7500
taacgcctgg gtcgaacgct ggaaggcggc gggccattac caggccgaag cagcgttgtt      7560
gcagtgcacg gcagatacac ttgctgatgc ggtgctgatt acgaccgctc acgcgtggca      7620
gcatcagggg aaaaaccttat ttatcagccg gaaaacctac cggattgatg gtagtggtca      7680
aatggcgatt accgttgatg ttgaagtggc gagcgataca ccgcatccgg cgcggattgg      7740
cctgaactgc cagctggcgc aggtagcaga gcgggtaaac tggctcggat tagggccgca      7800
agaaaactat cccgaccgcc ttactgccgc ctgttttgac cgctgggatc tgccattgtc      7860
agacatgtat accccgtacg tcttcccgag cgaaaacggt ctgcgctgcg ggacgcgcga      7920
attgaattat ggcccacacc agtggcgcgg cgacttccag ttcaacatca gccgctacag      7980
tcaacagcaa ctgatggaaa ccagccatcg ccatctgctg cacgcggaag aaggcacatg      8040
gctgaatatc gacggttttc atatggggat tggtggcgac gactcctgga gcccgtcagt      8100
atcggcggaa ttccagctga gcgcggtcg ctaccattac cagttggtct ggtgtcaaaa      8160
ataataataa ccgggcaggc catgtctgcc cgtatttcgc gtaaggaaat ccattatgta      8220
ctatttaaaa aacacaaact tttggatgtt cggtttattc tttttctttt acttttttat      8280
catgggagcc tacttcccgt ttttcccgat ttggctacat gacatcaacc atatcagcaa      8340
aagtgatacg ggtattattt ttgccgctat ttctctgttc tcgctattat tccaaccgct      8400
gtttggtctg ctttctgaca aactcggctc gagctgtgcc ttctagttgc cagccatctg      8460
ttgtttgccc ctccccgtg ccttccttga ccctggaagg tgccactccc actgtccttt      8520
cctaataaaa tgaggaaatt gcatcgcatt gtctgagtag gtgtcattct attctggggg      8580
gtgggttggg gcaggacagc aagggggagg attgggaaga caatagcagg catgctgggg      8640
atgcggtggg ctctatggct tctgaggcgg aaagaaccag ctggggctct agctagcata      8700
tacctgcagg gaattcctaa acagagcaat taggtaagaa aatgaaagaa aaggtatcca      8760
attatgaagg aagaagtaaa actatttcta tttgcagatg acatgactgt atacaaagaa      8820
aatcccaaat aatccacaca aaaactagta gagttaataa gcaaattcaa caaatttcag      8880
ggtacaaaat cagttgtgtt tctatacaca aacccacaat gaacaataaa aaaaggaaac      8940
```

```
taagaaaaca atttcctttg taataacatc ccaaagaata aaatacatgg gactaaattt    9000
aaccaaggaa gtgaaagaat tgtacactaa aaaccacaaa taattgctga ttaaatggaa    9060
agatgtccca tgttcacgga tagggatact taatattgtt aaatggcaat acttcccaaa    9120
gcaatctata gattcaatgc aatctctgtc aaaatttcaa atggtcttct ttgctgaaat    9180
ggaaaagcca atcctaaaat tcatatgtaa ttccatagga tccaaaaaag caaaaccaat    9240
attgaaaatag aaaaacaaag ttggagtact tacacttctc aatttcaaaa cttacaagct    9300
acagtaatta aaacagcatg gcaaaggcat aaggatagac atatggatca atggaataga    9360
ttcagagtcc agaaataaac acaacattta tggccatttg attttgata aggattgtca    9420
aggggggtctt gaacattcag tggggaaaga ataatatctt caacaagtgg tgctggaaca    9480
attggatagc catgtgcaaa atactctagt agactcctac cttatgtcac atacaataat    9540
taatttaaaa taaatcaatc ctaaatataa gggccaaaac cataaaactc ttagaagaaa    9600
acaggcgtaa tcttcatggt ttctgatttg tcaatggatt cttaaatttg acaccaaaag    9660
cacaagcaac aaaagataaa attgatacat ttgaatgcat aaaattttt taatttgcac    9720
atgaaatgac aatatcaaga aaatgaaaag acaatctgca gaatgggaga aaatatttac    9780
aagccacata tctgataagg gctgagtatc cagaatatat aacaaactct tccagctcaa    9840
caatgaaaac aaaaacaacg caattttaag aatgggcaaa ggacttgaat caacatttct    9900
ccaaagaaga tatgcgaata accagcaaac acatgaagtg atgctcaaca tcattactca    9960
taaaggaaat gtgaatcaaa accatatgac atactacttt acacccatta ggatgaagat   10020
aataatttta aaataacaag tgtcagcaag gatgcagaga aataggaact ttcctatgtt   10080
gctgataagc aatgcaaaag gatacaacca ctgtggaaaa cagtttggtg gttccttaaa   10140
aaattaaaaa taggattatt gtataactca gaaattccaa agtatatat atttggtata   10200
tatccaaaag aactgaaaac atattgttca tgcagaaatt tgtacacaaa tgcttattat   10260
tgctgcatta gctacaatag ccaaaagatg aaaacaaccc aaatgtccat tgacagatga   10320
acaaataact tgtggtataa acatacaatg ggaatattat ttttccatca aaaagaacga   10380
atactggcat gtgctacagc ttgtatgaat ctcagaaaca ttattacaag tgaatgtagc   10440
cagccacaac aggccatgta ttgtgtgatt ccgtttatat gaaatatcca gaggtggtgg   10500
ttgcagattt tgaatgtgct aaatgtcact gaattgaata ctttaaaatg gttaattgta   10560
tgttatgtga atttttaccctc aatttttaaa atgggtcata aacttatgtt tagcataatc   10620
cccttttaat tttaaaaaat gcagatatta catgagaaaa aatgtgctag agcatatttc   10680
aagacattaa agatggttat cagtgaatga tgagaaatta ggtaatgttt attattttcg   10740
ctttgctaaa attatttaaa aattacttgc atattaaatt ttttaatgcc taggaaagaa   10800
agactatagt tgtattgact aagatttcta cgagcatggg gaaaatgctt aatttgtagg   10860
gttaatcaag gataaaataa attgcattgt atgtacaatg tgatcccaag tattaaaac   10920
acactgctta tggtaacagt cagtctgtgg gagacaggtt aaaaagtgat attttccctt   10980
cctactctcc aaatttttctt aacaaacata tattatgact ataatcagaa aaaattattt   11040
ttaaaacgtc tactatgggg caagctaggt tcaaaaata aagtttgat aaatgtagtt   11100
ggcttgctat tgacaaggaa gacgtttaca ctggaattcg ggccctatat ggccatcatg   11160
gccatatagc gatcgctata tgctagcgat aacaattca cacaggaaac agctatgacc   11220
atgattacgc caagctctag ctagaggtcg acggtaatgg cagggcctgc cgccccgacg   11280
```

```
ttggctgcga gccctgggcc ttcacccgaa cttgggggt ggggtgggga aaaggaagaa      11340
acgcgggcgt attggcccca atgggtctc ggtggggtat cgacagagtg ccagccctgg      11400
gaccgaaccc cgcgtttatg aacaaacgac ccaacacccg tgcgttttat tctgtctttt      11460
tattgccgtc atagcgcggg ttccttccgg tattgtctcc ttccgtgttt cagttagcct      11520
cccccgttta aactcattac taaccggttt tagtcttcct tctcgtagac ttcaaactta      11580
tacttgatgc cttttcctc ctggacctca gagaggacgc ctgggtattc tgggagaagt      11640
ttatatttcc ccaaatcaat ttctgggaaa acgtgtcac tttcaaattc ctgcatgatc      11700
cttgtcacaa agagtctgag gtggcctggt tgattcatgg cttcctggta acagaactg       11760 cctccgacta tccaaaccat gtctacttta cttgccaatt ccggttgttc aataagtctt      11820
aaggcatcat ccaaactttt ggcaagaaaa tgagctcctc gtggtggttc tttgagttct      11880
ctactgagaa ctatattaat tctgtccttt aaaggtcgat tcttctcagg aatggagaac      11940
caggttttcc tacccataat caccagattc tgtttacctt ccactgaaga ggttgtggtc      12000
attctttgga agtacttgaa ctcgttcctg agcggaggcc agggtaggtc tccgttcttg      12060
ccaatcccca tattttggga cacggcgacg atgcagttca atggtcgaac catgatggcg      12120
cgaaacgatc ctcatcctgt ctcttgatca gatccgaaaa tggatataca agctcccggg      12180
agctttttgc aaaagcctag gcctccaaaa aagcctcctc actacttctg gaatagctca      12240
gaggcagagg cggcctcggc ctctgcataa ataaaaaaaa ttagtcagcc atggggcgga      12300
gaatgggcgg aactgggcgg agttaggggc gggatgggcg gagttagggg cgggactatg      12360
gttgctgact aattgagatg catgctttgc atacttctgc ctgctgggga gcctggggac      12420
tttccacacc ctaactgaca cacattccac ag                                    12452

<210> SEQ ID NO 2
<211> LENGTH: 14876
<212> TYPE: DNA
<213> ORGANISM: Artificial Sequence
<220> FEATURE:
<223> OTHER INFORMATION: pCLS09G1f2 vector
<220> FEATURE:
<221> NAME/KEY: promoter
<222> LOCATION: (4140)..(4834)
<220> FEATURE:
<221> NAME/KEY: gene
<222> LOCATION: (4937)..(8164)
<220> FEATURE:
<221> NAME/KEY: gene
<222> LOCATION: (8216)..(8418)
<220> FEATURE:
<221> NAME/KEY: gene
<222> LOCATION: (8711)..(11139)
<220> FEATURE:
<221> NAME/KEY: gene
<222> LOCATION: (11146)..(13574)

<400> SEQUENCE: 2
cacgtagtgg gccatcgccc tgatagacgg ttttcgccc tttgacgttg gagtccacgt        60
tctttaatag tggactcttg ttccaaactg gaacaacact caaccctatc tcggtctatt      120
cttttgattt ataagggatt ttgggatt cggcctattg gttaaaaaat gagctgattt        180
aacaaaaatt taacgcgaat taattctgtg gaatgtgtgt cagttagggt gtggaaagtc      240
cccaggctcc ccagcaggca gaagtatgca aagcatgcat ctcaattagt cagcaaccag      300
gtgtggaaag tccccaggct ccccagcagg cagaagtatg caaagcatgc atctcaatta      360
gtcagcaacc atagtcccgc ccctaactcc gcccatcccg cccctaactc cgcccagttc      420
```

```
cgcccattct ccgccccatg gctgactaat ttttttttatt tatgcagagg ccgaggccgc      480
ctctgcctct gagctattcc agaagtagtg aggaggcttt tttggaggcc taggcttttg      540
caaaaagctc ccgggagctt gtatatccat tttcggatct gatcaagaga caggatgagg      600
atcgtttcgc atgattgaac aagatggatt gcacgcaggt tctccggccg cttgggtgga      660
gaggctattc ggctatgact gggcacaaca gacaatcggc tgctctgatg ccgccgtgtt      720
ccggctgtca gcgcaggggc gcccggttct ttttgtcaag accgacctgt ccggtgccct      780
gaatgaactg caggacgagg cagcgcggct atcgtggctg gccacgacgg gcgttccttg      840
cgcagctgtg ctcgacgttg tcactgaagc gggaagggac tggctgctat tgggcgaagt      900
gccggggcag gatctcctgt catctcacct tgctcctgcc gagaaagtat ccatcatggc      960
tgatgcaatg cggcggctgc atacgcttga tccggctacc tgcccattcg accaccaagc     1020
gaaacatcgc atcgagcgag cacgtactcg gatggaagcc ggtcttgtcg atcaggatga     1080
tctggacgaa gagcatcagg ggctcgcgcc agccgaactg ttcgccaggc tcaaggcgcg     1140
catgcccgac ggcgaggatc tcgtcgtgac ccatggcgat gcctgcttgc cgaatatcat     1200
ggtggaaaat ggccgctttt ctggattcat cgactgtggc cggctgggtg tggcggaccg     1260
ctatcaggac atagcgttgg ctacccgtga tattgctgaa gagcttggcg gcgaatgggc     1320
tgaccgcttc ctcgtgcttt acggtatcgc cgctcccgat tcgcagcgca tcgccttcta     1380
tcgccttctt gacgagttct tctgagcggg actctgggt tcgcgaaatg accgaccaag     1440
cgacgcccaa cctgccatca cgagatttcg attccaccgc cgccttctat gaaaggttgg     1500
gcttcggaat cgtttccgg gacgccggct ggatgatcct ccagcgcggg gatctcatgc     1560
tggagttctt cgcccacccc aacttgttta ttgcagctta taatggttac aaataaagca     1620
atagcatcac aaatttcaca aataaagcat ttttttcact gcattctagt tgtggtttgt     1680
ccaaactcat caatgtatct tatcatgtct gtataccgtc gacctctagc tagagcttgg     1740
cgtaatcatg gtcatagctg tttcctgtgt gaaattgtta tccgctcaca attccacaca     1800
acatacgagc cggaagcata aagtgtaaag cctggggtgc ctaatgagtg agctaactca     1860
cattaattgc gttgcgctca ctgcccgctt tccagtcggg aaacctgtcg tgccagctgc     1920
attaatgaat cggccaacgc gcggggagag gcggtttgcg tattgggcgc tcttccgctt     1980
cctcgctcac tgactcgctg cgctcggtcg ttcggctgcg gcgagcggta tcagctcact     2040
caaaggcggt aatacggtta tccacagaat caggggataa cgcaggaaag aacatgtgag     2100
caaaaggcca gcaaaaggcc aggaaccgta aaaaggccgc gttgctggcg ttttttccata     2160 ggctccgccc ccctgacgag catcacaaaa atcgacgctc aagtcagagg tggcgaaacc     2220
cgacaggact ataaagatac caggcgtttc ccctggaag ctccctcgtg cgctctcctg      2280
ttccgaccct gccgcttacc ggatacctgt ccgcctttct cccttcggga agcgtggcgc     2340
tttctcaatg ctcacgctgt aggtatctca gttcggtgta ggtcgttcgc tccaagctgg     2400
gctgtgtgca cgaaccccc gttcagcccg accgctgcgc cttatccggt aactatcgtc      2460
ttgagtccaa cccggtaaga cacgacttat cgccactggc agcagccact ggtaacagga     2520
ttagcagagc gaggtatgta ggcggtgcta cagagttctt gaagtggtgg cctaactacg     2580
gctacactag aaggacagta tttggtatct gcgctctgct gaagccagtt accttcggaa     2640
aaagagttgg tagctcttga tccggcaaac aaaccaccgc tggtagcggt ggtttttttg     2700
tttgcaagca gcagattacg cgcagaaaaa aaggatctca agaagatcct ttgatctttt     2760
ctacggggtc tgacgctcag tggaacgaaa actcacgtta agggattttg gtcatgagat     2820
```

```
tatcaaaaag gatcttcacc tagatccttt taaattaaaa atgaagtttt aaatcaatct   2880
aaagtatata tgagtaaact tggtctgaca gttaccaatg cttaatcagt gaggcaccta   2940
tctcagcgat ctgtctattt cgttcatcca tagttgcctg actcccgtc gtgtagataa    3000 ctacgatacg ggagggctta ccatctggcc ccagtgctgc aatgataccg cgagacccac   3060
gctcaccggc tccagattta tcagcaataa accagccagc cggaagggcc gagcgcagaa   3120
gtggtcctgc aactttatcc gcctccatcc agtctattaa ttgttgccgg gaagctagag   3180
taagtagttc gccagttaat agtttgcgca acgttgttgc cattgctaca ggcatcgtgg   3240
tgtcacgctc gtcgtttggt atggcttcat tcagctccgg ttcccaacga tcaaggcgag   3300
ttacatgatc ccccatgttg tgcaaaaaag cggttagctc cttcggtcct ccgatcgttg   3360
tcagaagtaa gttggccgca gtgttatcac tcatggttat ggcagcactg cataattctc   3420
ttactgtcat gccatccgta agatgctttt ctgtgactgg tgagtactca accaagtcat   3480
tctgagaata gtgtatgcgg cgaccgagtt gctcttgccc ggcgtcaata cgggataata   3540
ccgcgccaca tagcagaact ttaaaagtgc tcatcattgg aaaacgttct cggggcgaa    3600 aactctcaag gatcttaccg ctgttgagat ccagttcgat gtaacccact cgtgcaccca   3660
actgatcttc agcatctttt actttcacca gcgtttctgg gtgagcaaaa acaggaaggc   3720
aaaatgccgc aaaaaaggga ataagggcga cacggaaatg ttgaatactc atactcttcc   3780
tttttcaata ttattgaagc atttatcagg gttattgtct catgagcgga tacatatttg   3840
aatgtattta gaaaaataaa caaataggggt tccgcgcac atttcccga aaagtgccac     3900 ctgacgtcga cggatcggga gatctcccga tcccctatgg tcgactctca gtacaatctg   3960
ctctgatgcc gcatagttaa gccagtatct gctccctgct tgtgtgttgg aggtcgctga   4020
gtagtgcgcg agcaaaattt aagctacaac aaggcaaggc ttgaccgaca attgcatgaa   4080
gaatctgctt agggttaggc gttttgcgct gcttcgcgat gtacgggcca gatatacgcg   4140
ttgacattga ttattgacta gttattaata gtaatcaatt acgggtcat tagttcatag     4200 cccatatatg gagttccgcg ttacataact tacggtaaat ggcccgcctg gctgaccgcc   4260
caacgacccc cgcccattga cgtcaataat gacgtatgtt cccatagtaa cgccaatagg   4320
gactttccat tgacgtcaat gggtggagta tttacggtaa actgcccact tggcagtaca   4380
tcaagtgtat catatgccaa gtacgccccc tattgacgtc aatgacgta aatggcccgc     4440 ctggcattat gcccagtaca tgaccttatg ggactttcct acttggcagt acatctacgt   4500
attagtcatc gctattacca tggtgatgcg gttttggcag tacatcaatg ggcgtggata   4560
gcggtttgac tcacggggat ttccaagtct ccaccccatt gacgtcaatg ggagtttgtt   4620
ttggcaccaa aatcaacggg actttccaaa atgtcgtaac aactccgccc cattgacgca   4680
aatgggcggt aggcgtgtac ggtgggaggt ctatataagc agagctcgtt tagtgaaccg   4740
tcagatcgcc tggagacgcc atccacgctg ttttgacctc catagaagac accgggaccg   4800
atccagcctc cggactctag aggatcgaac ccttaagctt ctcgcgcaac ctattttccc   4860
ctcgaacact ttttaagccg tagataaaca ggctgggaca cttcacatga gcgaaaaata   4920
catcgtcacc tgggacatgt tgcagatcca tgcacgtaaa ctcgcaagcc gactgatgcc   4980
ttctgaacaa tggaaaggca ttattgccgt aagccgtggc ggtctggtac cggtgggtga   5040
agaccagaaa cagcacctcg aactgagccg cgatattgcc cagcgtttca acgcgctgta   5100
tggcgagatc gatcccgtcg ttttacaacg tcgtgactgg gaaaaccctg gcgttaccca   5160
```

```
acttaatcgc cttgcagcac atcccccttt cgccagctgg cgtaatagcg aagaggcccg   5220
caccgatcgc ccttcccaac agttgcgcag cctgaatggc gaatggcgct ttgcctggtt   5280
tccggcacca gaagcggtgc cggaaagctg gctggagtgc gatcttcctg aggccgatac   5340
tgtcgtcgtc ccctcaaact ggcagatgca cggttacgat gcgcccatct acaccaacgt   5400
gacctatccc attacggtca atccgccgtt tgttcccacg gagaatccga cgggttgtta   5460
ctcgctcaca tttaatgttg atgaaagctg gctacaggaa ggccagacgc gaattatttt   5520
tgatggcgtt aactcggcgt ttcatctgtg gtgcaacggg cgctgggtcg gttacggcca   5580
ggacagtcgt ttgccgtctg aatttgacct gagcgcattt ttacgcgccg gagaaaaccg   5640
cctcgcggtg atggtgctgc gctggagtga cggcagttat ctggaagatc aggatatgtg   5700
gcggatgagc ggcattttcc gtgacgtctc gttgctgcat aaaccgacta cacaaatcag   5760
cgatttccat gttgccactc gctttaatga tgatttcagc cgcgctgtac tggaggctga   5820
agttcagatg tgcggcgagt tgcgtgacta cctacgggta acagtttctt tatggcaggg   5880
tgaaacgcag gtcgccagcg gcaccgcgcc tttcggcggt gaaattatcg atgagcgtgg   5940
tggttatgcc gatcgcgtca cactacgtct gaacgtcgaa acccgaaac tgtggagcgc    6000 cgaaatcccg aatctctatc gtgcggtggt tgaactgcac accgccgacg gcacgctgat   6060
tgaagcagaa gcctgcgatg tcggtttccg cgaggtgcgg attgaaaatg gtctgctgct   6120
gctgaacggc aagccgttgc tgattcgagg cgttaaccgt cacgagcatc atcctctgca   6180
tggtcaggtc atggatgagc agacgatggt gcaggatatc ctgctgatga agcagaacaa   6240
ctttaacgcg gtgcgctgtt cgcattatcc gaaccatccg ctgtggtaca cgctgtgcga   6300
ccgctacggc ctgtatgtgg tggatgaagc caatattgaa acccacggca tggtgccaat   6360
gaatcgtctg accgatgatc cgcgctggct accggcgatg agcgaacgcg taacgcgaat   6420
ggtgcagcgc gatcgtaatc acccgagtgt gatcatctgg tcgctgggga atgaatcagg   6480
ccacggcgct aatcacgacg cgctgtatcg ctggatcaaa tctgtcgatc cttcccgccc   6540
ggtgcagtat gaaggcggcg gagccgacac cacggccacc gatattattt gcccgatgta   6600
cgcgcgcgtg atgaagacc agcccttccc ggctgtgccg aaatggtcca tcaaaaaatg    6660
gctttcgcta cctggagaga cgcgcccgct gatcctttgc gaatacgccc acgcgatggg   6720
taacagtctt ggcggtttcg ctaaatactg gcaggcgttt cgtcagtatc cccgtttaca   6780
gggcggcttc gtctgggact gggtggatca gtcgctgatt aaatatgatg aaaacggcaa   6840
cccgtggtcg gcttacggcg gtgattttgg cgatacgccg aacgatcgcc agttctgtat   6900
gaacggtctg gtctttgccg accgcacgcc gcatccagcg ctgacggaag caaaacacca   6960
gcagcagttt ttccagttcc gtttatccgg gcaaaccatc gaagtgacca gcgaatacct   7020
gttccgtcat agcgataacg agctcctgca ctggatggtg gcgctggatg gtaagccgct   7080
ggcaagcggt gaagtgcctc tggatgtcgc tccacaaggt aaacagttga ttgaactgcc   7140
tgaactaccg cagccggaga cgccgggca actctggctc acagtacgcg tagtgcaacc   7200
gaacgcgacc gcatggtcag aagccgggca catcagcgcc tggcagcagt ggcgtctggc   7260
ggaaaacctc agtgtgacgc tccccgccgc gtcccacgcc atcccgcatc tgaccaccag   7320
cgaaatggat ttttgcatcg agctgggtaa taagcgttgg caatttaacc gccagtcagg   7380
ctttctttca cagatgtgga ttggcgataa aaacaactg ctgacgccgc tgcgcgatca    7440
gttcacccgt gcaccgctgg ataacgacat tggcgtaagt gaagcgaccc gcattgaccc   7500
taacgcctgg gtcgaacgct ggaaggcggc gggccattac caggccgaag cagcgttgtt   7560
```

-continued

```
gcagtgcacg gcagatacac ttgctgatgc ggtgctgatt acgaccgctc acgcgtggca    7620
gcatcagggg aaaaccttat ttatcagccg gaaaacctac cggattgatg gtagtggtca    7680
aatggcgatt accgttgatg ttgaagtggc gagcgataca ccgcatccgg cgcggattgg    7740
cctgaactgc cagctggcgc aggtagcaga gcgggtaaac tggctcggat tagggccgca    7800
agaaaactat cccgaccgcc ttactgccgc ctgttttgac cgctgggatc tgccattgtc    7860
agacatgtat accccgtacg tcttcccgag cgaaaacggt ctgcgctgcg ggacgcgcga    7920
attgaattat ggcccacacc agtggcgcgg cgacttccag ttcaacatca gccgctacag    7980
tcaacagcaa ctgatggaaa ccagccatcg ccatctgctg cacgcggaag aaggcacatg    8040
gctgaatatc gacggtttcc atatggggat tggtggcgac gactcctgga gcccgtcagt    8100
atcggcggaa ttccagctga gcgccggtcg ctaccattac cagttggtct ggtgtcaaaa    8160
ataataataa ccgggcaggc catgtctgcc cgtatttcgc gtaaggaaat ccattatgta    8220
ctatttaaaa aacacaaact tttggatgtt cggtttattc ttttttcttt acttttttat    8280
catgggagcc tacttcccgt ttttcccgat ttggctacat gacatcaacc atatcagcaa    8340
aagtgatacg ggtattattt ttgccgctat ttctctgttc tcgctattat tccaaccgct    8400
gtttggtctg ctttctgaca aactcggctc gagctgtgcc ttctagttgc cagccatctg    8460
ttgtttgccc ctccccgtg ccttccttga ccctggaagg tgccactccc actgtccttt    8520
cctaataaaa tgaggaaatt gcatcgcatt gtctgagtag gtgtcattct attctggggg    8580
gtggggtggg gcaggacagc aaggggagg attgggaaga caatagcagg catgctgggg    8640
atgcggtggg ctctatggct tctgaggcgg aaagaaccag ctggggctct agctagcata    8700
tacctgcagg gaattcctaa acagagcaat taggtaagaa aatgaaagaa aaggtatcca    8760
attatgaagg aagaagtaaa actatttcta tttgcagatg acatgactgt atacaaagaa    8820
aatcccaaat aatccacaca aaaactagta gagttaataa gcaaattcaa caaatttcag    8880
ggtacaaaat cagttgtgtt tctatacaca aacccacaat gaacaataaa aaaaggaaac    8940
taagaaaaca atttccttta taataacatc ccaaagaata aaatacatgg gactaaattt    9000
aaccaaggaa gtgaaagaat tgtacactaa aaaccacaaa taattgctga ttaaatggaa    9060
agatgtccca tgttcacgga tagggatact taatattgtt aaatggcaat acttcccaaa    9120
gcaatctata gattcaatgc aatctctgtc aaaatttcaa atggtcttct ttgctgaaat    9180
ggaaaagcca atcctaaaat tcatatgtaa ttccatagga tccaaaaaag caaaaccaat    9240
attgaaatag aaaaacaaag ttggagtact tacacttctc aatttcaaaa cttcaagct    9300
acagtaatta aaacagcatg gcaaaggcat aaggatagac atatggatca atggaataga    9360
ttcagagtcc agaaataaac acaacattta tggccctttg attttgata aggattgtca    9420
aggggtctt gaacattcag tggggaaaga ataatatctt caacaagtgg tgctggaaca    9480
attggatagc catgtgcaaa atactctagt agactcctac cttatgtcac atacaataat    9540
taatttaaaa taaatcaatc ctaaatataa gggccaaaac cataaaactc ttagaagaaa    9600
acaggcgtaa tcttcatggt ttctgatttg tcaatggatt cttaaatttg acaccaaaag    9660
cacaagcaac aaaagataaa attgatacat ttgaatgcat aaaatttttt taatttgcac    9720
atgaaatgac aatatcaaga aaatgaaaag acaatctgca gaatgggaga aaatatttac    9780
aagccacata tctgataagg gctgagtatc cagaatatat aacaaactct tccagctcaa    9840
caatgaaaac aaaaacaacg caattttaag aatgggcaaa ggacttgaat caacatttct    9900
```

```
ccaaagaaga tatgcgaata accagcaaac acatgaagtg atgctcaaca tcattactca    9960
taaaggaaat gtgaatcaaa accatatgac atactacttt acacccatta ggatgaagat   10020
aataatttta aaataacaag tgtcagcaag gatgcagaga aataggaact ttcctatgtt   10080
gctgataagc aatgcaaaag gatacaacca ctgtggaaaa cagtttggtg gttccttaaa   10140
aaattaaaaa taggattatt gtataactca gaaattccaa agtatatat  atttggtata   10200
tatccaaaag aactgaaaac atattgttca tgcagaaatt tgtacacaaa tgcttattat   10260
tgctgcatta gctacaatag ccaaaagatg aaaacaaccc aaatgtccat tgacagatga   10320
acaaataact tgtggtataa acatacaatg ggaatattat ttttccatca aaagaacga    10380
atactggcat gtgctacagc ttgtatgaat ctcagaaaca ttattacaag tgaatgtagc   10440
cagccacaac aggccatgta ttgtgtgatt ccgtttatat gaaatatcca gaggtggtgg   10500
ttgcagattt tgaatgtgct aaatgtcact gaattgaata ctttaaaatg gttaattgta   10560
tgttatgtga attttacctc aattttttaa atgggtcata aacttatgtt tagcataatc   10620
cccttttaat tttaaaaaat gcagatatta catgagaaaa aatgtgctag agcatatttc   10680
aagacattaa agatggttat cagtgaatga tgagaaatta ggtaatgttt attattttcg   10740
ctttgctaaa attatttaaa aattacttgc atattaaatt ttttaatgcc taggaaagaa   10800
agactatagt tgtattgact aagatttcta cgagcatggg gaaatgctt  aatttgtagg   10860
gttaatcaag gataaaataa attgcattgt atgtacaatg tgatcccaag tatttaaaac   10920
acactgctta tggtaacagt cagtctgtgg gagacaggtt aaaaagtgat attttcccctt  10980
cctactctcc aaattttctt aacaaacata tattatgact ataatcagaa aaaattattt   11040
ttaaaacgtc tactatgggg caagctaggt tcaaaaaata gaagtttgat aaatgtagtt   11100
ggcttgctat tgacaaggaa gacgtttaca ctggaattcg ggcccgaatt cctaaacaga   11160
gcaattaggt aagaaaatga aagaaaaggt atccaattat gaaggaagaa gtaaaactat   11220
ttctatttgc agatgacatg actgtataca aagaaaatcc caataatcc  acacaaaaac   11280
tagtagagtt aataagcaaa ttcaacaaat ttcagggtac aaaatcagtt gtgtttctat   11340
acacaaaccc acaatgaaca ataaaaaaag gaaactaaga aaacaatttc ctttataata   11400
acatcccaaa gaataaaata catgggacta aatttaacca aggaagtgaa agaattgtac   11460
actaaaaacc acaaataatt gctgattaaa tggaaagatg tcccatgttc acggatatggg  11520
atacttaata ttgttaaatg gcaatacttc ccaaagcaat ctatagattc aatgcaatct   11580
ctgtcaaaat ttcaaatggt cttctttgct gaaatggaaa agccaatcct aaaattcata   11640
tgtaattcca taggatccaa aaaagcaaaa ccaatattga aatagaaaaa caagttgga   11700
gtacttacac ttctcaattt caaaacttac aagctcagt  aattaaaaca gcatggcaaa   11760
ggcataagga tagacatatg gatcaatgga atagattcag agtccagaaa taaacacaac   11820
atttatggcc atttgatttt tgataaggat tgtcaagggg gtcttgaaca ttcagtgggg   11880
aaagaataat atcttcaaca agtggtgctg gaacaattgg atagccatgt gcaaaatact   11940
ctagtagact cctaccttat gtcacataca ataattaatt taaataaat  caatcctaaa   12000
tataagggcc aaaaccataa aactcttaga agaaaacagg cgtaatcttc atggtttctg   12060
atttgtcaat ggattcttaa atttgacacc aaaagcacaa gcaacaaaag ataaaattga   12120
tacatttgaa tgcataaaat ttttttaatt tgcacatgaa atgacaatat caagaaaatg   12180
aaaagacaat ctgcagaatg ggagaaaata tttacaagcc acatatctga taagggctga   12240
gtatccagaa tatataacaa actcttccag ctcaacaatg aaaacaaaaa caacgcaatt   12300
```

```
ttaagaatgg gcaaaggact tgaatcaaca tttctccaaa gaagatatgc gaataaccag   12360
caaacacatg aagtgatgct caacatcatt actcataaag gaaatgtgaa tcaaaaccat   12420
atgacatact actttacacc cattaggatg aagataataa ttttaaaata acaagtgtca   12480
gcaaggatgc agagaaatag gaactttcct atgttgctga taagcaatgc aaaaggatac   12540
aaccactgtg gaaacagtt tggtggttcc ttaaaaaatt aaaaatagga ttattgtata   12600
actcagaaat tccaaaagta tatatatttg gtatatatcc aaaagaactg aaaacatatt   12660
gttcatgcag aaatttgtac acaaatgctt attattgctg cattagctac aatagccaaa   12720
agatgaaaac aacccaaatg tccattgaca gatgaacaaa taacttgtgg tataaacata   12780
caatgggaat attattttc catcaaaaag aacgaatact ggcatgtgct acagcttgta   12840
tgaatctcag aaacattatt acaagtgaat gtagccagcc acaacaggcc atgtattgtg   12900
tgattccgtt tatatgaaat atccagaggt ggtggttgca gattttgaat gtgctaaatg   12960
tcactgaatt gaatacttta aaatggttaa ttgtatgtta tgtgaatttt acctcaattt   13020
tttaaatggg tcataaactt atgtttagca taatcccctt ttaattttaa aaaatgcaga   13080
tattacatga gaaaaaatgt gctagagcat atttcaagac attaaagatg gttatcagtg   13140
aatgatgaga aattaggtaa tgtttattat tttcgctttg ctaaaattat ttaaaaatta   13200
cttgcatatt aaatttttta atgcctagga aagaaagact atagttgtat tgactaagat   13260
ttctacgagc atggggaaaa tgcttaattt gtagggttaa tcaaggataa aataaattgc   13320
attgtatgta caatgtgatc ccaagtattt aaaacacact gcttatggta acagtcagtc   13380
tgtgggagac aggttaaaaa gtgatatttt cccttcctac tctccaaatt ttcttaacaa   13440
acatatatta tgactataat cagaaaaaat tattttttaaa acgtctacta tggggcaagc   13500
taggttcaaa aaatagaagt ttgataaatg tagttggctt gctattgaca aggaagacgt   13560
ttacactgga attcggccat catggccata tagcgatcgc tatatgctag cgataacaat   13620
ttcacacagg aaacagctat gaccatgatt acgccaagct ctagctagag gtcgacggta   13680
atggcagggc ctgccgcccc gacgttggct gcgagccctg ggccttcacc cgaacttggg   13740 gggtgggtg gggaaaagga agaaacgcgg gcgtattggc cccaatgggg tctcggtggg   13800
gtatcgacag agtgccagcc ctgggaccga accccgcgtt tatgaacaaa cgacccaaca   13860
cccgtgcgtt ttattctgtc tttttattgc cgtcatagcg cgggttcctt ccggtattgt   13920
ctccttccgt gtttcagtta gcctcccccg tttaaactca ttactaaccg gttttagtct   13980
ttcttctcgt agacttcaaa cttatacttg atgcctttt cctcctggac tcagagagg   14040 acgcctgggt attctgggag aagtttatat ttccccaaat caatttctgg gaaaaacgtg   14100
tcactttcaa attcctgcat gatccttgtc acaaagagtc tgaggtggcc tggttgattc   14160
atggcttcct ggtaaacaga actgcctccg actatccaaa ccatgtctac tttacttgcc   14220
aattccggtt gttcaataag tcttaaggca tcatccaaac ttttggcaag aaaatgagct   14280
cctcgtggtg gttctttgag ttctctactg agaactatat taattctgtc ctttaaaggt   14340
cgattcttct caggaatgga gaaccaggtt ttcctaccca taatcaccag attctgttta   14400
ccttccactg aagaggttgt ggtcattctt tggaagtact tgaactcgtt cctgagcgga   14460
ggccagggta ggtctccgtt cttgccaatc cccatatttt gggacacggc gacgatgcag   14520
ttcaatggtc gaaccatgat ggcgcgaaac gatcctcatc ctgtctcttg atcagatccg   14580
aaaatggata tacaagctcc cgggagcttt ttgcaaaagc ctaggcctcc aaaaaagcct   14640
```

-continued

```
cctcactact tctggaatag ctcagaggca gaggcggcct cggcctctgc ataaataaaa    14700
aaaattagtc agccatgggg cggagaatgg gcggaactgg gcggagttag ggcgggatg    14760 ggcggagtta ggggcgggac tatggttgct gactaattga gatgcatgct ttgcatactt    14820
ctgcctgctg gggagcctgg gactttcca caccctaact gacacacatt ccacag        14876
```

<210> SEQ ID NO 3
<211> LENGTH: 17311
<212> TYPE: DNA
<213> ORGANISM: Artificial Sequence
<220> FEATURE:
<223> OTHER INFORMATION: pCLS09G1f3 vector
<220> FEATURE:
<221> NAME/KEY: gene
<222> LOCATION: (3926)..(6354)
<220> FEATURE:
<221> NAME/KEY: promoter
<222> LOCATION: (6575)..(7269)
<220> FEATURE:
<221> NAME/KEY: gene
<222> LOCATION: (7372)..(10599)
<220> FEATURE:
<221> NAME/KEY: gene
<222> LOCATION: (10651)..(10853)
<220> FEATURE:
<221> NAME/KEY: gene
<222> LOCATION: (11146)..(13574)
<220> FEATURE:
<221> NAME/KEY: gene
<222> LOCATION: (13581)..(16009)

<400> SEQUENCE: 3

```
cacgtagtgg gccatcgccc tgatagacgg ttttcgccc tttgacgttg gagtccacgt     60
tctttaatag tggactcttg ttccaaactg gaacaacact caaccctatc tcggtctatt    120
cttttgattt ataagggatt ttggggattt cggcctattg gttaaaaaat gagctgattt    180
aacaaaaatt taacgcgaat taattctgtg gaatgtgtgt cagttagggt gtggaaagtc    240
cccaggctcc ccagcaggca gaagtatgca aagcatgcat ctcaattagt cagcaaccag    300
gtgtggaaag tccccaggct ccccagcagg cagaagtatg caaagcatgc atctcaatta    360
gtcagcaacc atagtcccgc ccctaactcc gcccatcccg cccctaactc cgcccagttc    420
cgcccattct ccgccccatg ctgactaat ttttttttatt tatgcagagg ccgaggccgc    480
ctctgcctct gagctattcc agaagtagtg aggaggcttt tttggaggcc taggcttttg    540
caaaaagctc ccgggagctt gtatatccat tttcggatct gatcaagaga caggatgagg    600
atcgtttcgc atgattgaac aagatggatt gcacgcaggt tctccggccg cttgggtgga    660
gaggctattc ggctatgact gggcacaaca gacaatcggc tgctctgatg ccgccgtgtt    720
ccggctgtca gcgcaggggc gcccggttct ttttgtcaag accgacctgt ccggtgccct    780
gaatgaactg caggacgagg cagcgcggct atcgtggctg gccacgacgg gcgttccttg    840
cgcagctgtg ctcgacgttg tcactgaagc gggaagggac tggctgctat tgggcgaagt    900
gccggggcag gatctcctgt catctcacct tgctcctgcc gagaaagtat ccatcatggc    960
tgatgcaatg cggcggctgc atacgcttga tccggctacc tgcccattcg accaccaagc    1020
gaaacatcgc atcgagcgag cacgtactcg gatggaagcc ggtcttgtcg atcaggatga    1080
tctggacgaa gagcatcagg ggctcgcgcc agccgaactg ttcgccaggc tcaaggcgcg    1140
catgcccgac ggcgaggatc tcgtcgtgac ccatggcgat gcctgcttgc cgaatatcat    1200
ggtggaaaat ggccgctttt ctggattcat cgactgtggc cggctgggtg tggcggaccg    1260
ctatcaggac atagcgttgg ctacccgtga tattgctgaa gagcttggcg gcgaatgggc    1320
```

```
tgaccgcttc ctcgtgcttt acggtatcgc cgctcccgat tcgcagcgca tcgccttcta    1380
tcgccttctt gacgagttct tctgagcggg actctggggt tcgcgaaatg accgaccaag    1440
cgacgcccaa cctgccatca cgagatttcg attccaccgc cgccttctat gaaaggttgg    1500
gcttcggaat cgttttccgg gacgccggct ggatgatcct ccagcgcggg gatctcatgc    1560
tggagttctt cgcccacccc aacttgttta ttgcagctta taatggttac aaataaagca    1620
atagcatcac aaatttcaca aataaagcat tttttcact gcattctagt tgtggtttgt     1680
ccaaactcat caatgtatct tatcatgtct gtataccgtc gacctctagc tagagcttgg    1740
cgtaatcatg gtcatagctg tttcctgtgt gaaattgtta tccgctcaca attccacaca    1800
acatacgagc cggaagcata agtgtaaag cctggggtgc ctaatgagtg agctaactca     1860
cattaattgc gttgcgctca ctgcccgctt tccagtcggg aaacctgtcg tgccagctgc    1920
attaatgaat cggccaacgc gcggggagag gcggtttgcg tattgggcgc tcttccgctt    1980
cctcgctcac tgactcgctg cgctcggtcg ttcggctgcg gcgagcggta tcagctcact    2040
caaaggcggt aatacggtta ccacagaat caggggataa cgcaggaaag aacatgtgag     2100
caaaaggcca gcaaaaggcc aggaaccgta aaaaggccgc gttgctggcg tttttccata    2160
ggctccgccc ccctgacgag catcacaaaa atcgacgctc aagtcagagg tggcgaaacc    2220
cgacaggact ataaagatac caggcgtttc ccccctggaag ctcccctcgtg cgctctcctg   2280 ttccgaccct gccgcttacc ggatacctgt ccgcctttct cccttcggga agcgtggcgc    2340
tttctcaatg ctcacgctgt aggtatctca gttcggtgta ggtcgttcgc tccaagctgg    2400
gctgtgtgca cgaaccccc gttcagcccg accgctgcgc cttatccggt aactatcgtc     2460
ttgagtccaa cccggtaaga cacgacttat cgccactggc agcagccact ggtaacagga    2520
ttagcagagc gaggtatgta ggcggtgcta cagagttctt gaagtggtgg cctaactacg    2580
gctacactag aaggacagta tttggtatct gcgctctgct gaagccagtt accttcggaa    2640
aaagagttgg tagctcttga tccggcaaac aaaccaccgc tggtagcggt ggtttttttg    2700
tttgcaagca gcagattacg cgcagaaaaa aaggatctca agaagatcct ttgatctttt    2760
ctacggggtc tgacgctcag tggaacgaaa actcacgtta agggattttg gtcatgagat    2820
tatcaaaaag gatcttcacc tagatccttt taaattaaaa atgaagtttt aaatcaatct    2880
aaagtatata tgagtaaact tggtctgaca gttaccaatg cttaatcagt gaggcaccta    2940
tctcagcgat ctgtctattt cgttcatcca tagttgcctg actccccgtc gtgtagataa    3000
ctacgatacg ggagggctta ccatctggcc ccagtgctgc aatgataccg cgagacccac    3060
gctcaccggc tccagattta tcagcaataa accagccagc cggaagggcc gagcgcagaa    3120
gtggtcctgc aactttatcc gcctccatcc agtctattaa ttgttgccgg gaagctagag    3180
taagtagttc gccagttaat agtttgcgca acgttgttgc cattgctaca ggcatcgtgg    3240
tgtcacgctc gtcgtttggt atggcttcat tcagctccgg ttcccaacga tcaaggcgag    3300
ttacatgatc ccccatgttg tgcaaaaaag cggttagctc cttcggtcct ccgatcgttg    3360
tcagaagtaa gttggccgca gtgttatcac tcatggttat ggcagcactg cataattctc    3420
ttactgtcat gccatccgta agatgctttt ctgtgactgg tgagtactca accaagtcat    3480
tctgagaata gtgtatgcgg cgaccgagtt gctcttgccc ggcgtcaata cgggataata    3540
ccgcgccaca tagcagaact ttaaaagtgc tcatcattgg aaaacgttct cggggcgaa     3600 aactctcaag gatcttaccg ctgttgagat ccagttcgat gtaacccact cgtgcaccca    3660
```

```
actgatcttc agcatctttt actttcacca gcgtttctgg gtgagcaaaa acaggaaggc    3720
aaaatgccgc aaaaaaggga ataagggcga cacggaaatg ttgaatactc atactcttcc    3780
tttttcaata ttattgaagc atttatcagg gttattgtct catgagcgga tacatatttg    3840
aatgtattta gaaaataaaa caaataggg ttccgcgcac atttccccga aaagtgccac    3900
ctgacgtcga cggatcggga gatctgaatt cctaaacaga gcaattaggt aagaaaatga    3960
aagaaaaggt atccaattat gaaggaagaa gtaaaactat ttctatttgc agatgacatg    4020
actgtataca aagaaaatcc caaataatcc acacaaaaac tagtagagtt aataagcaaa    4080
ttcaacaaat ttcagggtac aaaatcagtt gtgtttctat acacaaaccc acaatgaaca    4140
ataaaaaaag gaaactaaga aaacaatttc ctttataata acatcccaaa gaataaaata    4200
catgggacta aatttaacca aggaagtgaa agaattgtac actaaaaacc acaataatt    4260 gctgattaaa tggaaagatg tcccatgttc acggataggg atacttaata ttgttaaatg    4320
gcaatacttc ccaaagcaat ctatagattc aatgcaatct ctgtcaaaat ttcaaatggt    4380
cttctttgct gaaatggaaa agccaatcct aaaattcata tgtaattcca taggatccaa    4440
aaaagcaaaa ccaatattga aatagaaaaa caagttgga gtacttacac ttctcaattt    4500
caaaacttac aagctacagt aattaaaaca gcatggcaaa ggcataagga tagacatatg    4560
gatcaatgga atagattcag agtccagaaa taaacacaac atttatggcc atttgatttt    4620
tgataaggat tgtcaagggg gtcttgaaca ttcagtgggg aaagaataat atcttcaaca    4680
agtggtgctg gaacaattgg atagccatgt gcaaaatact ctagtagact cctaccttat    4740
gtcacataca ataattaatt taaaataaat caatcctaaa tataagggcc aaaaccataa    4800
aactcttaga agaaaacagg cgtaatcttc atggtttctg atttgtcaat ggattcttaa    4860
atttgacacc aaaagcacaa gcaacaaaag ataaaattga tacatttgaa tgcataaaat    4920
ttttttaatt tgcacatgaa atgacaatat caagaaaatg aaaagacaat ctgcagaatg    4980
ggagaaaata tttacaagcc acatatctga taagggctga gtatccagaa tatataacaa    5040
actcttccag ctcaacaatg aaaacaaaaa caacgcaatt ttaagaatgg gcaaaggact    5100
tgaatcaaca tttctccaaa gaagatatgc gaataaccag caaacacatg aagtgatgct    5160
caacatcatt actcataaag gaaatgtgaa tcaaaccat atgacatact actttacacc    5220
cattaggatg aagataataa ttttaaaata acaagtgtca gcaaggatgc agagaaatag    5280 gaacttttcct atgttgctga taagcaatgc aaaaggatac aaccactgtg gaaaacagtt    5340
tggtggttcc ttaaaaaatt aaaaatagga ttattgtata actcagaaat tccaaaagta    5400
tatatatttg gtatatatcc aaaagaactg aaaacatatt gttcatgcag aaatttgtac    5460
acaaatgctt attattgctg cattagctac aatagccaaa agatgaaaac aacccaaatg    5520
tccattgaca gatgaacaaa taacttgtgg tataaacata caatgggaat attattttc    5580 catcaaaaag aacgaatact ggcatgtgct acagcttgta tgaatctcag aaacattatt    5640
acaagtgaat gtagccagcc acaacaggcc atgtattgtg tgattccgtt tatatgaaat    5700
atccagaggt ggtggttgca gattttgaat gtgctaaatg tcactgaatt gaatactta    5760 aaatggttaa ttgtatgtta tgtgaatttt acctcaattt tttaaatggg tcataaactt    5820
atgtttagca taatccccctt ttaattttaa aaaatgcaga tattacatga gaaaaaatgt    5880
gctagagcat atttcaagac attaaagatg gttatcagtg aatgatgaga aattaggtaa    5940
tgtttattat tttcgctttg ctaaaattat ttaaaaatta cttgcatatt aaattttta    6000 atgcctagga aagaaagact atagttgtat tgactaagat ttctacgagc atggggaaaa    6060
```

```
tgcttaattt gtagggttaa tcaaggataa aataaattgc attgtatgta caatgtgatc   6120
ccaagtattt aaaacacact gcttatggta acagtcagtc tgtgggagac aggttaaaaa   6180
gtgatatttt cccttcctac tctccaaatt ttcttaacaa acatatatta tgactataat   6240
cagaaaaaat tattttaaa acgtctacta tggggcaagc taggttcaaa aaatagaagt    6300
ttgataaatg tagttggctt gctattgaca aggaagacgt ttacactgga attcagatct   6360
cccgatcccc tatggtcgac tctcagtaca atctgctctg atgccgcata gttaagccag   6420
tatctgctcc ctgcttgtgt gttggaggtc gctgagtagt gcgcgagcaa aatttaagct   6480
acaacaaggc aaggcttgac cgacaattgc atgaagaatc tgcttagggt taggcgtttt   6540
gcgctgcttc gcgatgtacg ggccagatat acgcgttgac attgattatt gactagttat   6600
taatagtaat caattacggg gtcattagtt catagcccat atatggagtt ccgcgttaca   6660
taacttacgg taaatggccc gcctggctga ccgcccaacg acccccgccc attgacgtca   6720
ataatgacgt atgttcccat agtaacgcca tagggactt tccattgacg tcaatgggtg    6780
gagtatttac ggtaaactgc ccacttggca gtacatcaag tgtatcatat gccaagtacg   6840 cccccctattg acgtcaatga cggtaaatgg cccgcctggc attatgccca gtacatgacc   6900
ttatgggact ttcctacttg gcagtacatc tacgtattag tcatcgctat taccatggtg   6960
atgcggtttt ggcagtacat caatgggcgt ggatagcggt ttgactcacg ggatttcca    7020 agtctccacc ccattgacgt caatgggagt ttgttttggc accaaaatca acgggacttt   7080
ccaaaatgtc gtaacaactc cgccccattg acgcaaatgg gcggtaggcg tgtacggtgg   7140
gaggtctata taagcagagc tcgtttagtg aaccgtcaga tcgcctggag acgccatcca   7200
cgctgttttg acctccatag aagacaccgg gaccgatcca gcctccggac tctagaggat   7260 cgaacccta agcttctcgc gcaacctatt ttcccctcga acactttta agccgtagat    7320 aaacaggctg ggacacttca catgagcgaa aaatacatcg tcacctggga catgttgcag   7380
atccatgcac gtaaactcgc aagccgactg atgccttctg aacaatggaa aggcattatt   7440
gccgtaagcc gtggcggtct ggtaccggtg ggtgaagacc agaaacagca cctcgaactg   7500
agccgcgata ttgcccagcg tttcaacgcg ctgtatggcg agatcgatcc cgtcgtttta   7560
caacgtcgtg actgggaaaa ccctggcgtt acccaactta atcgccttgc agcacatccc   7620
cctttcgcca gctggcgtaa tagcgaagag gcccgcaccg atcgcccttc ccaacagttg   7680
cgcagcctga atggcgaatg gcgctttgcc tggtttccgg caccagaagc ggtgccggaa   7740
agctggctga gtgcgatct tcctgaggcc gatactgtcg tcgtccctc aaactggcag     7800 atgcacggtt acgatgcgcc catctacacc aacgtgacct atcccattac ggtcaatccg   7860
ccgtttgttc ccacggagaa tccgacgggt tgttactcgc tcacatttaa tgttgatgaa   7920
agctggctac aggaaggcca gacgcgaatt attttttgatg gcgttaactc ggcgtttcat   7980
ctgtggtgca acgggcgctg ggtcggttac ggccaggaca gtcgtttgcc gtctgaattt   8040
gacctgagcg catttttacg cgccggagaa aaccgcctcg cggtgatggt gctgcgctgg   8100
agtgacggca gttatctgga agatcaggat atgtggcgga tgagcggcat tttccgtgac   8160
gtctcgttgc tgcataaacc gactacacaa atcagcgatt tccatgttgc cactcgcttt   8220
aatgatgatt tcagccgcgc tgtactggag gctgaagttc agatgtgcgg cgagttgcgt   8280
gactacctac gggtaacagt ttctttatgg cagggtgaaa cgcaggtcgc cagcggcacc   8340
gcgcctttcg gcggtgaaat tatcgatgag cgtggtggtt atgccgatcg cgtcacacta   8400
```

```
cgtctgaacg tcgaaaaccc gaaactgtgg agcgccgaaa tcccgaatct ctatcgtgcg    8460
gtggttgaac tgcacaccgc cgacggcacg ctgattgaag cagaagcctg cgatgtcggt    8520
ttccgcgagg tgcggattga aaatggtctg ctgctgctga acggcaagcc gttgctgatt    8580
cgaggcgtta accgtcacga gcatcatcct ctgcatggtc aggtcatgga tgagcagacg    8640
atggtgcagg atatcctgct gatgaagcag aacaacttta acgccgtgcg ctgttcgcat    8700
tatccgaacc atccgctgtg gtacacgctg tgcgaccgct acggcctgta tgtggtggat    8760
gaagccaata ttgaaaccca cggcatggtg ccaatgaatc gtctgaccga tgatccgcgc    8820
tggctaccgg cgatgagcga acgcgtaacg cgaatggtgc agcgcgatcg taatcacccg    8880
agtgtgatca tctggtcgct ggggaatgaa tcaggccacg gcgctaatca cgacgcgctg    8940
tatcgctgga tcaaatctgt cgatccttcc cgcccggtgc agtatgaagg cggcggagcc    9000
gacaccacgg ccaccgatat tatttgcccg atgtacgcgc gcgtggatga agaccagccc    9060
ttcccggctg tgccgaaatg gtccatcaaa aaatggcttt cgctacctgg agagacgcgc    9120
ccgctgatcc tttgcgaata cgcccacgcg atgggtaaca gtcttggcgg tttcgctaaa    9180
tactggcagg cgtttcgtca gtatccccgt ttacagggcg gcttcgtctg ggactgggtg    9240
gatcagtcgc tgattaaata tgatgaaaac ggcaacccgt ggtcggctta cggcggtgat    9300
tttggcgata cgccaacga tcgccagttc tgtatgaacg gtctggtctt tgccgaccgc    9360
acgccgcatc cagcgctgac ggaagcaaaa caccagcagc agttttttcca gttccgttta    9420
tccgggcaaa ccatcgaagt gaccagcgaa tacctgttcc gtcatagcga taacgagctc    9480
ctgcactgga tggtggcgct ggatggtaag ccgctggcaa gcggtgaagt gcctctggat    9540
gtcgctccac aaggtaaaca gttgattgaa ctgcctgaac taccgcagcc ggagagcgcc    9600
gggcaactct ggctcacagt acgcgtagtg caaccgaacg cgaccgcatg gtcagaagcc    9660
gggcacatca gcgcctggca gcagtggcgt ctggcggaaa acctcagtgt gacgctcccc    9720
gccgcgtccc acgccatccc gcatctgacc accagcgaaa tggattttg catcgagctg    9780
ggtaataagc gttggcaatt taaccgccag tcaggctttc tttcacagat gtggattggc    9840
gataaaaaac aactgctgac gccgctgcgc gatcagttca cccgtgcacc gctggataac    9900
gacattggcg taagtgaagc gacccgcatt gaccctaacg cctgggtcga acgctggaag    9960
gcggcgggcc attaccaggc cgaagcagcg ttgttgcagt gcacggcaga tacacttgct   10020
gatgcggtgc tgattacgac cgctcacgcg tggcagcatc aggggaaaac cttatttatc   10080
agccggaaaa cctaccggat tgatggtagt ggtcaaatgg cgattaccgt tgatgttgaa   10140
gtggcgagcg ataccgca tccggcgcgg attggcctga actgccagct ggcgcaggta   10200
gcagagcggg taaactggct cggattaggg ccgcaagaaa actatcccga ccgccttact   10260
gccgcctgtt ttgaccgctg ggatctgcca ttgtcagaca tgtataccc gtacgtcttc   10320
ccgagcgaaa acggtctgcg ctgcgggacg cgcgaattga attatggccc acaccagtgg   10380
cgcggcgact ccagttcaa catcagccgc tacagtcaac agcaactgat ggaaaccagc   10440
catcgccatc tgctgcacgc ggaagaaggc acatggctga atatcgacgg tttccatatg   10500
gggattggtg gcgacgactc ctggagcccg tcagtatcgg cggaattcca gctgagcgcc   10560
ggtcgctacc attaccagtt ggtctggtgt caaaaataat aataaccggg caggccatgt   10620
ctgcccgtat ttcgcgtaag gaaatccatt atgtactatt taaaaaacac aaacttttgg   10680
atgttcggtt tattcttttt cttttacttt tttatcatgg gagcctactt cccgtttttc   10740
ccgatttggc tacatgacat caaccatatc agcaaaagtg atacgggtat tatttttgcc   10800
```

```
gctatttctc tgttctcgct attattccaa ccgctgtttg gtctgctttc tgacaaactc   10860
ggctcgagct gtgccttcta gttgccagcc atctgttgtt tgcccctccc ccgtgccttc   10920
cttgaccctg gaaggtgcca ctcccactgt cctttcctaa taaaatgagg aaattgcatc   10980
gcattgtctg agtaggtgtc attctattct gggggtggg gtggggcagg acagcaaggg    11040
ggaggattgg gaagacaata gcaggcatgc tggggatgcg gtgggctcta tggcttctga   11100
ggcggaaaga accagctggg gctctagcta gcatatacct gcagggaatt cctaaacaga   11160
gcaattaggt aagaaaatga aagaaaaggt atccaattat gaaggaagaa gtaaaactat   11220
ttctatttgc agatgacatg actgtataca aagaaaatcc caaataatcc acacaaaaac   11280
tagtagagtt aataagcaaa ttcaacaaat ttcagggtac aaaatcagtt gtgtttctat   11340
acacaaaccc acaatgaaca ataaaaaaag gaaactaaga aaacaatttc ctttataata   11400
acatcccaaa gaataaaata catgggacta aatttaacca aggaagtgaa agaattgtac   11460
actaaaaacc acaataatt gctgattaaa tggaaagatg tcccatgttc acggataggg    11520
atacttaata ttgttaaatg gcaatacttc ccaaagcaat ctatagattc aatgcaatct   11580
ctgtcaaaat ttcaaatggt cttctttgct gaaatggaaa agccaatcct aaaattcata   11640
tgtaattcca taggatccaa aaaagcaaaa ccaatattga aatagaaaaa caaagttgga   11700
gtacttacac ttctcaattt caaaacttac aagctacagt aattaaaaca gcatggcaaa   11760
ggcataagga tagacatatg gatcaatgga atagattcag agtccagaaa taaacacaac   11820
atttatggcc atttgatttt tgataaggat tgtcaagggg gtcttgaaca ttcagtgggg   11880
aaagaataat atcttcaaca agtggtgctg gaacaattgg atagccatgt gcaaaatact   11940
ctagtagact cctaccttat gtcacataca ataattaatt taaataaat caatcctaaa    12000 tataagggcc aaaaccataa aactcttaga agaaaacagg cgtaatcttc atggttcctg   12060
atttgtcaat ggattcttaa atttgacacc aaaagcacaa gcaacaaaag ataaaattga   12120
tacatttgaa tgcataaaat ttttttaatt tgcacatgaa atgacaatat caagaaaatg   12180
aaaagacaat ctgcagaatg ggagaaaata tttacaagcc acatatctga taagggctga   12240
gtatccagaa tatataacaa actcttccag ctcaacaatg aaaacaaaaa caacgcaatt   12300
ttaagaatgg gcaaaggact tgaatcaaca tttctccaaa gaagatatgc gaataaccag   12360
caaacacatg aagtgatgct caacatcatt actcataaag gaaatgtgaa tcaaaaccat   12420
atgacatact actttacacc cattaggatg aagataataa ttttaaaata acaagtgtca   12480
gcaaggatgc agagaaatag gaactttcct atgttgctga taagcaatgc aaaaggatac   12540
aaccactgtg gaaaacagtt tggtggttcc ttaaaaaatt aaaaatagga ttattgtata   12600
actcagaaat tccaaaagta tatatatttg gtatatatcc aaaagaactg aaaacatatt   12660
gttcatgcag aaatttgtac acaaatgctt attattgctg cattagctac aatagccaaa   12720
agatgaaaac aacccaaatg tccattgaca gatgaacaaa taacttgtgg tataaacata   12780
caatgggaat attattttc catcaaaaag aacgaatact ggcatgtgct acagcttgta    12840
tgaatctcag aaacattatt acaagtgaat gtagccagcc acaacaggcc atgtattgtg   12900
tgattccgtt tatatgaaat atccagaggt ggtggttgca gattttgaat gtgctaaatg   12960
tcactgaatt gaatacttta aaatggttaa ttgtatgtta tgtgaatttt acctcaattt   13020
tttaaatggg tcataaactt atgtttagca taatcccctt ttaattttaa aaatgcaga    13080 tattacatga gaaaaaatgt gctagagcat atttcaagac attaaagatg gttatcagtg   13140
```

```
aatgatgaga aattaggtaa tgtttattat tttcgctttg ctaaaattat ttaaaaatta    13200
cttgcatatt aaattttta atgcctagga aagaaagact atagttgtat tgactaagat      13260
ttctacgagc atggggaaaa tgcttaattt gtagggttaa tcaaggataa aataaattgc     13320
attgtatgta caatgtgatc ccaagtattt aaaacacact gcttatggta acagtcagtc     13380
tgtgggagac aggttaaaaa gtgatatttt cccttcctac tctccaaatt ttcttaacaa     13440
acatatatta tgactataat cagaaaaaat tattttaaaa acgtctacta tggggcaagc     13500
taggttcaaa aaatagaagt ttgataaatg tagttggctt gctattgaca aggaagacgt     13560
ttacactgga attcgggccc gaattcctaa acagagcaat taggtaagaa aatgaaagaa     13620
aaggtatcca attatgaagg aagaagtaaa actatttcta tttgcagatg acatgactgt     13680
atacaaagaa aatcccaaat aatccacaca aaaactagta gagttaataa gcaaattcaa     13740
caaatttcag ggtacaaaat cagttgtgtt tctatacaca aacccacaat gaacaataaa     13800
aaaaggaaac taagaaaaca atttcctta taataacatc ccaaagaata aaatacatgg      13860
gactaaattt aaccaaggaa gtgaaagaat tgtacactaa aaaccacaaa taattgctga     13920
ttaaatggaa agatgtccca tgttcacgga tagggatact taatattgtt aaatggcaat     13980
acttcccaaa gcaatctata gattcaatgc aatctctgtc aaaatttcaa atggtcttct     14040
ttgctgaaat ggaaaagcca atcctaaaat tcatatgtaa ttccatagga tccaaaaaag     14100 caaaccaat attgaaatag aaaaacaaag ttggagtact tacacttctc aatttcaaaa      14160
cttacaagct acagtaatta aaacagcatg gcaaaggcat aaggatagac atatggatca     14220
atggaataga ttcagagtcc agaaataaac acaacattta tggccatttg attttgata     14280 aggattgtca aggggggtctt gaacattcag tggggaaaga ataatatctt caacaagtgg    14340
tgctggaaca attggatagc catgtgcaaa atactctagt agactcctac cttatgtcac    14400
atacaataat taatttaaaa taaatcaatc ctaaatataa gggccaaaac cataaaactc    14460
ttagaagaaa acaggcgtaa tcttcatggt ttctgatttg tcaatggatt cttaaatttg    14520
acaccaaaag cacaagcaac aaaagataaa attgatacat ttgaatgcat aaaatttttt   14580
taatttgcac atgaaatgac aatatcaaga aaatgaaaag acaatctgca gaatgggaga    14640
aaatatttac aagccacata tctgataagg gctgagtatc cagaatatat aacaaactct    14700
tccagctcaa caatgaaaac aaaaacaacg caattttaag aatgggcaaa ggacttgaat    14760
caacatttct ccaaagaaga tatgcgaata accagcaaac acatgaagtg atgctcaaca   14820
tcattactca taaggaaat gtgaatcaaa accatatgac atactacttt acacccatta      14880
ggatgaagat aataatttta aaataacaag tgtcagcaag gatgcagaga aataggaact    14940
ttcctatgtt gctgataagc aatgcaaaag gatacaacca ctgtggaaaa cagtttggtg    15000
gttccttaaa aaattaaaaa taggattatt gtataactca gaaattccaa aagtatatat     15060
atttggtata tatccaaaag aactgaaaac atattgttca tgcagaaatt tgtacacaaa    15120
tgcttattat tgctgcatta gctacaatag ccaaaagatg aaaacaaccc aaatgtccat    15180
tgacagatga acaaataact tgtggtataa acatacaatg ggaatattat ttttccatca    15240 aaagaacga atactggcat gtgctacagc ttgtatgaat ctcagaaaca ttattacaag     15300
tgaatgtagc cagccacaac aggccatgta ttgtgtgatt ccgtttatat gaaatatcca    15360
gaggtggtgg ttgcagattt tgaatgtgct aaatgtcact gaattgaata ctttaaaatg    15420
gttaattgta tgttatgtga attttacctc aattttttaa atgggtcata aacttatgtt    15480
tagcataatc ccctttaat tttaaaaaat gcagatatta catgagaaaa aatgtgctag    15540
```

```
agcatatttc aagacattaa agatggttat cagtgaatga tgagaaatta ggtaatgttt    15600
attattttcg ctttgctaaa attatttaaa aattacttgc atattaaatt ttttaatgcc    15660
taggaaagaa agactatagt tgtattgact aagatttcta cgagcatggg gaaaatgctt    15720
aatttgtagg gttaatcaag gataaaataa attgcattgt atgtacaatg tgatcccaag    15780
tatttaaaac acactgctta tggtaacagt cagtctgtgg gagacaggtt aaaaagtgat    15840 attttcccctt cctactctcc aaattttctt aacaaacata tattatgact ataatcagaa    15900
aaaattattt ttaaaacgtc tactatgggg caagctaggt tcaaaaaata gaagtttgat    15960
aaatgtagtt ggcttgctat tgacaaggaa gacgtttaca ctggaattcg gccatcatgg    16020
ccatatagcg atcgctatat gctagcgata acaatttcac acaggaaaca gctatgacca    16080
tgattacgcc aagctctagc tagaggtcga cggtaatggc agggcctgcc gccccgacgt    16140
tggctgcgag ccctgggcct tcacccgaac ttgggggtg gggtggggaa aaggaagaaa    16200
cgcgggcgta ttggccccaa tggggtctcg gtggggtatc gacagagtgc cagccctggg    16260
accgaacccc gcgtttatga acaaacgacc caacacccgt gcgttttatt ctgtcttttt    16320
attgccgtca tagcgcgggt tccttccggt attgtctcct tccgtgtttc agttagcctc    16380
ccccgtttaa actcattact aaccggtttt agtctttctt ctcgtagact tcaaacttat    16440
acttgatgcc ttttcctcc tggacctcag agaggacgcc tgggtattct gggagaagtt    16500
tatatttccc caaatcaatt tctgggaaaa acgtgtcact ttcaaattcc tgcatgatcc    16560
ttgtcacaaa gagtctgagg tggcctggtt gattcatggc ttcctggtaa acagaactgc    16620
ctccgactat ccaaaccatg tctactttac ttgccaattc cggttgttca ataagtctta    16680
aggcatcatc caaacttttg gcaagaaaat gagctcctcg tggtggttct ttgagttctc    16740
tactgagaac tatattaatt ctgtccttta aaggtcgatt cttctcagga atggagaacc    16800
aggttttcct acccataatc accagattct gtttaccttc cactgaagag gttgtggtca    16860
ttctttggaa gtacttgaac tcgttcctga gcggaggcca gggtaggtct ccgttcttgc    16920
caatccccat attttgggac acggcgacga tgcagttcaa tggtcgaacc atgatggcgc    16980
gaaacgatcc tcatcctgtc tcttgatcag atccgaaaat ggatatacaa gctcccggga    17040 gcttttttgca aaagcctagg cctccaaaaa agcctcctca ctacttctgg aatagctcag    17100
aggcagaggc ggcctcggcc tctgcataaa taaaaaaaat tagtcagcca tggggcgag    17160 aatgggcgga actgggcgga gttaggggcg ggatgggcgg agttaggggc gggactatgg    17220
ttgctgacta attgagatgc atgctttgca tacttctgcc tgctggggag cctggggact    17280
ttccacaccc taactgacac acattccaca g                                  17311
```

<210> SEQ ID NO 4
<211> LENGTH: 14887
<212> TYPE: DNA
<213> ORGANISM: Artificial Sequence
<220> FEATURE:
<223> OTHER INFORMATION: pCLS09G1f4 vector
<220> FEATURE:
<221> NAME/KEY: gene
<222> LOCATION: (3926)..(6354)
<220> FEATURE:
<221> NAME/KEY: promoter
<222> LOCATION: (6575)..(7269)
<220> FEATURE:
<221> NAME/KEY: gene
<222> LOCATION: (7372)..(10599)
<220> FEATURE:
<221> NAME/KEY: gene

```
<222> LOCATION: (10651)..(10853)
<220> FEATURE:
<221> NAME/KEY: gene
<222> LOCATION: (11146)..(13574)

<400> SEQUENCE: 4
cacgtagtgg gccatcgccc tgatagacgg ttttcgccc tttgacgttg gagtccacgt      60
tctttaatag tggactcttg ttccaaactg aacaacact caaccctatc tcggtctatt     120
cttttgattt ataagggatt ttggggattt cggcctattg gttaaaaaat gagctgattt    180
aacaaaaatt taacgcgaat taattctgtg aatgtgtgt cagttagggt gtggaaagtc     240
cccaggctcc ccagcaggca gaagtatgca aagcatgcat ctcaattagt cagcaaccag    300
gtgtggaaag tccccaggct ccccagcagg cagaagtatg caaagcatgc atctcaatta    360
gtcagcaacc atagtcccgc ccctaactcc gcccatcccg cccctaactc cgcccagttc    420
cgcccattct ccgccccatg gctgactaat tttttttatt tatgcagagg ccgaggccgc    480
ctctgcctct gagctattcc agaagtagtg aggaggcttt tttggaggcc taggcttttg    540
caaaaagctc ccgggagctt gtatatccat tttcggatct gatcaagaga caggatgagg    600
atcgtttcgc atgattgaac aagatggatt gcacgcaggt tctccggccg cttgggtgga    660
gaggctattc ggctatgact gggcacaaca gacaatcggc tgctctgatg ccgccgtgtt    720
ccggctgtca gcgcagggc gcccggttct ttttgtcaag accgacctgt ccggtgccct    780
gaatgaactg caggacgagg cagcgcggct atcgtggctg gccacgacgg gcgttccttg    840
cgcagctgtg ctcgacgttg tcactgaagc gggaagggac tggctgctat tgggcgaagt    900
gccggggcag gatctcctgt catctcacct tgctcctgcc gagaaagtat ccatcatggc    960
tgatgcaatg cggcggctgc atacgcttga tccggctacc tgcccattcg accaccaagc   1020
gaaacatcgc atcgagcgag cacgtactcg gatggaagcc ggtcttgtcg atcaggatga   1080
tctggacgaa gagcatcagg ggctcgcgcc agccgaactg ttcgccaggc tcaaggcgcg   1140
catgcccgac ggcgaggatc tcgtcgtgac ccatggcgat gcctgcttgc cgaatatcat   1200
ggtggaaaat ggccgctttt ctggattcat cgactgtggc cggctgggtg tggcggaccg   1260
ctatcaggac atagcgttgg ctacccgtga tattgctgaa gagcttggcg gcgaatgggc   1320
tgaccgcttc ctcgtgcttt acggtatcgc cgctcccgat tcgcagcgca tcgccttcta   1380
tcgccttctt gacgagttct tctgagcggg actctgggt tcgcgaaatg accgaccaag   1440
cgacgcccaa cctgccatca cgagatttcg attccaccgc cgccttctat gaaaggttgg   1500
gcttcggaat cgtttccgg gacgccggct ggatgatcct ccagcgcggg gatctcatgc   1560
tggagttctt cgcccacccc aacttgttta ttgcagctta taatggttac aaataaagca   1620
atagcatcac aaatttcaca aataaagcat ttttttcact gcattctagt tgtggtttgt   1680
ccaaactcat caatgtatct tatcatgtct gtataccgtc gacctctagc tagagcttgg   1740
cgtaatcatg gtcatagctg tttcctgtgt gaaattgtta tccgctcaca attccacaca   1800
acatacgagc cggaagcata aagtgtaaag cctggggtgc ctaatgagtg agctaactca   1860
cattaattgc gttgcgctca ctgcccgctt tccagtcggg aaacctgtcg tgccagctgc   1920
attaatgaat cggccaacgc gcggggagag gcggtttgcg tattgggcgc tcttccgctt   1980
cctcgctcac tgactcgctg cgctcggtcg ttcggctgcg gcgagcggta tcagctcact   2040
caaaggcggt aatacggtta tccacagaat caggggataa cgcaggaaag aacatgtgag   2100
caaaaggcca gcaaaaggcc aggaaccgta aaaaggccgc gttgctggcg ttttccata    2160
```

```
ggctccgccc ccctgacgag catcacaaaa atcgacgctc aagtcagagg tggcgaaacc      2220
cgacaggact ataaagatac caggcgtttc ccctggaag ctccctcgtg cgctctcctg      2280
ttccgaccct gccgcttacc ggatacctgt ccgcctttct cccttcggga agcgtggcgc      2340
tttctcaatg ctcacgctgt aggtatctca gttcggtgta ggtcgttcgc tccaagctgg      2400
gctgtgtgca cgaacccccc gttcagcccg accgctgcgc cttatccggt aactatcgtc      2460
ttgagtccaa cccggtaaga cacgacttat cgccactggc agcagccact ggtaacagga      2520
ttagcagagc gaggtatgta ggcggtgcta cagagttctt gaagtggtgg cctaactacg      2580
gctacactag aaggacagta tttggtatct gcgctctgct gaagccagtt accttcggaa      2640
aaagagttgg tagctcttga tccggcaaac aaaccaccgc tggtagcggt ggttttttg      2700 tttgcaagca gcagattacg cgcagaaaaa aaggatctca agaagatcct ttgatctttt      2760
ctacggggtc tgacgctcag tggaacgaaa actcacgtta agggattttg gtcatgagat      2820
tatcaaaaag gatcttcacc tagatccttt taaattaaaa atgaagtttt aaatcaatct      2880
aaagtatata tgagtaaact tggtctgaca gttaccaatg cttaatcagt gaggcaccta      2940
tctcagcgat ctgtctattt cgttcatcca tagttgcctg actccccgtc gtgtagataa      3000
ctacgatacg ggagggctta ccatctggcc ccagtgctgc aatgataccg cgagacccac      3060
gctcaccggc tccagattta tcagcaataa accagccagc cggaagggcc gagcgcagaa      3120
gtggtcctgc aactttatcc gcctccatcc agtctattaa ttgttgccgg gaagctagag      3180
taagtagttc gccagttaat agtttgcgca acgttgttgc cattgctaca ggcatcgtgg      3240
tgtcacgctc gtcgtttggt atggcttcat tcagctccgg ttcccaacga tcaaggcgag      3300
ttacatgatc ccccatgttg tgcaaaaaag cggttagctc cttcggtcct ccgatcgttg      3360
tcagaagtaa gttggccgca gtgttatcac tcatggttat ggcagcactg cataattctc      3420
ttactgtcat gccatccgta agatgctttt ctgtgactgg tgagtactca accaagtcat      3480
tctgagaata gtgtatgcgg cgaccgagtt gctcttgccc ggcgtcaata cgggataata      3540
ccgcgccaca tagcagaact ttaaaagtgc tcatcattgg aaaacgttct cggggcgaa      3600 aactctcaag gatcttaccg ctgttgagat ccagttcgat gtaacccact cgtgcaccca      3660
actgatcttc agcatctttt actttcacca gcgtttctgg gtgagcaaaa acaggaaggc      3720
aaaatgccgc aaaaaaggga ataagggcga cacggaaatg ttgaatactc atactcttcc      3780
tttttcaata ttattgaagc atttatcagg gttattgtct catgagcgga tacatatttg      3840
aatgtattta gaaaaataaa caataggggt tccgcgcac atttccccga aaagtgccac      3900
ctgacgtcga cggatcggga gatctgaatt cctaaacaga gcaattaggt aagaaaatga      3960 aagaaaggt atccaattat gaaggaagaa gtaaaactat ttctatttgc agatgacatg      4020
actgtataca aagaaaatcc caaataatcc acacaaaaac tagtagagtt aataagcaaa      4080
ttcaacaaat ttcagggtac aaaatcagtt gtgtttctat acacaaaccc acaatgaaca      4140
ataaaaaaag gaaactaaga aaacaatttc ctttataata acatcccaaa gaataaaata      4200
catgggacta aatttaacca aggaagtgaa agaattgtac actaaaaacc acaaataatt      4260
gctgattaaa tggaaagatg tcccatgttc acggataggg atacttaata ttgttaaatg      4320
gcaatacttc ccaaagcaat ctatagattc aatgcaatct ctgtcaaaat ttcaaatggt      4380
cttctttgct gaaatggaaa agccaatcct aaaattcata tgtaattcca taggatccaa      4440
aaaagcaaaa ccaatattga aatagaaaaa caaagttgga gtacttacac ttctcaattt      4500
caaaacttac aagctacagt aattaaaaca gcatggcaaa ggcataagga tagacatatg      4560
```

```
gatcaatgga atagattcag agtccagaaa taaacacaac atttatggcc atttgatttt    4620
tgataaggat tgtcaagggg gtcttgaaca ttcagtgggg aaagaataat atcttcaaca    4680
agtggtgctg gaacaattgg atagccatgt gcaaaatact ctagtagact cctaccttat    4740
gtcacataca ataattaatt taaaataaat caatcctaaa tataagggcc aaaaccataa    4800
aactcttaga agaaaacagg cgtaatcttc atggtttctg atttgtcaat ggattcttaa    4860
atttgacacc aaaagcacaa gcaacaaaag ataaaattga tacatttgaa tgcataaaat    4920
ttttttaatt tgcacatgaa atgacaatat caagaaaatg aaaagacaat ctgcagaatg    4980
ggagaaaata tttacaagcc acatatctga taagggctga gtatccagaa tatataacaa    5040
actcttccag ctcaacaatg aaaacaaaaa caacgcaatt ttaagaatgg gcaaaggact    5100
tgaatcaaca tttctccaaa gaagatatgc gaataaccag caaacacatg aagtgatgct    5160
caacatcatt actcataaag gaatgtgaaa tcaaaccat atgacatact actttacacc      5220
cattaggata agataataa ttttaaaata acaagtgtca gcaaggatgc agagaaatag      5280
gaactttcct atgttgctga taagcaatgc aaaaggatac aaccactgtg gaaaacagtt     5340
tggtggttcc ttaaaaaatt aaaaatagga ttattgtata actcagaaat tccaaaagta    5400
tatatatttg gtatatatcc aaaagaactg aaaacatatt gttcatgcag aaatttgtac     5460
acaaatgctt attattgctg cattagctac aatagccaaa agatgaaaaac aacccaaatg   5520 tccattgaca gatgaacaaa taacttgtgg tataaacata caatgggaat attatttttc    5580
catcaaaaag aacgaatact ggcatgtgct acagcttgta tgaatctcag aaacattatt    5640
acaagtgaat gtagccagcc acaacaggcc atgtattgtg tgattccgtt tatatgaaat    5700
atccagaggt ggtggttgca gattttgaat gtgctaaatg tcactgaatt gaatacttta    5760
aaatggttaa ttgtatgtta tgtgaatttt acctcaattt tttaaatggg tcataaactt    5820
atgtttagca taatccccctt ttaattttaa aaatgcaga tattcatga gaaaaaatgt      5880 gctagagcat atttcaagac attaaagatg gttatcagtg aatgatgaga aattaggtaa     5940
tgtttattat tttcgctttg ctaaaattat ttaaaaatta cttgcatatt aaattttta      6000 atgcctagga aagaaagact atagttgtat tgactaagat ttctacgagc atggggaaaa    6060
tgcttaattt gtagggttaa tcaaggataa aataaattgc attgtatgta caatgtgatc    6120
ccaagtattt aaaacacact gcttatggta acagtcagtc tgtgggagac aggttaaaaa    6180
gtgatatttt cccttcctac tctccaaatt ttcttaacaa acatatatta tgactataat    6240
cagaaaaaat tattttttaaa acgtctacta tggggcaagc taggttcaaa aaatagaagt   6300
ttgataaatg tagttggctt gctattgaca aggaagacgt ttacactgga attcagatct    6360
cccgatcccc tatggtcgac tctcagtaca atctgctctg atgccgcata gttaagccag    6420
tatctgctcc ctgcttgtgt gttggaggtc gctgagtagt gcgcgagcaa atttaagct      6480 acaacaaggc aaggcttgac cgacaattgc atgaagaatc tgcttagggt taggcgtttt    6540
gcgctgcttc gcgatgtacg ggccagatat acgcgttgac attgattatt gactagttat    6600
taatagtaat caattacggg gtcattagtt catagcccat atatggagtt ccgcgttaca    6660
taacttacgg taaatggccc gcctggctga ccgcccaacg accccgccc  attgacgtca     6720 ataatgacgt atgttcccat agtaacgcca atagggactt tccattgacg tcaatgggtg    6780 gagtattac ggtaaactgc ccacttggca gtacatcaag tgtatcatat gccaagtacg    6840 cccctattg acgtcaatga cggtaaatgg cccgcctggc attatgccca gtacatgacc     6900
```

```
ttatgggact ttcctacttg gcagtacatc tacgtattag tcatcgctat taccatggtg   6960
atgcggtttt ggcagtacat caatgggcgt ggatagcggt ttgactcacg gggatttcca   7020
agtctccacc ccattgacgt caatgggagt ttgttttggc accaaaatca acgggacttt   7080
ccaaaatgtc gtaacaactc cgccccattg acgcaaatgg gcggtaggcg tgtacggtgg   7140
gaggtctata taagcagagc tcgtttagtg aaccgtcaga tcgcctggag acgccatcca   7200
cgctgttttg acctccatag aagacaccgg gaccgatcca gcctccggac tctagaggat   7260
cgaacccttc agcttctcgc gcaacctatt ttcccctcga acacttttta agccgtagat   7320
aaacaggctg ggacacttca catgagcgaa aaatacatcg tcacctggga catgttgcag   7380
atccatgcac gtaaactcgc aagccgactg atgccttctg aacaatggaa aggcattatt   7440
gccgtaagcc gtggcggtct ggtaccgtgg ggtgaagacc agaaacagca cctcgaactg   7500
agccgcgata ttgcccagcg tttcaacgcg ctgtatggcg agatcgatcc cgtcgtttta   7560
caacgtcgtg actgggaaaa ccctggcgtt acccaactta atcgccttgc agcacatccc   7620
cctttcgcca gctggcgtaa tagcgaagag gcccgcaccg atcgcccttc ccaacagttg   7680
cgcagcctga atggcgaatg gcgctttgcc tggtttccgg caccagaagc ggtgccggaa   7740
agctggctag agtgcgatct tcctgaggcc gatactgtcg tcgtccctc aaactggcag   7800
atgcacggtt acgatgcgcc catctacacc aacgtgacct atcccattac ggtcaatccg   7860
ccgtttgttc ccacgaagaa tccgacgggt tgttactcgc tcacatttaa tgttgatgaa   7920
agctggctac aggaaggcca gacgcgaatt atttttgatg gcgttaactc ggcgtttcat   7980
ctgtggtgca acgggcgctg ggtcggttac ggccaggaca gtcgtttgcc gtctgaattt   8040
gacctgagcg catttttacg cgccggagaa aaccgcctcg cggtgatggt gctgcgctgg   8100
agtgacggca gttatctgga agatcaggat atgtggcgga tgagcggcat tttccgtgac   8160
gtctcgttgc tgcataaacc gactacacaa atcagcgatt tccatgttgc cactcgcttt   8220
aatgatgatt tcagccgcgc tgtactggag gctgaagttc agatgtgcgg cgagttgcgt   8280
gactacctac gggtaacagt ttctttatgg cagggtgaaa cgcaggtcgc cagcggcacc   8340
gcgcctttcg gcggtgaaat tatcgatgag cgtggtggtt atgccgatcg cgtcacacta   8400
cgtctgaacg tcgaaaaccc gaaactgtgg agcgccgaaa tcccgaatct ctatcgtgcg   8460
gtggttgaac tgcacaccgc cgacggcacg ctgattgaag cagaagcctg cgatgtcggt   8520
ttccgcgagg tgcggattga aaatggtctg ctgctgctga acggcaagcc gttgctgatt   8580
cgaggcgtta accgtcacga gcatcatcct ctgcatggtc aggtcatgga tgagcagacg   8640
atggtgcagg atatcctgct gatgaagcag aacaactttc acgccgtgcg ctgttcgcat   8700
tatccgaacc atccgctgtg gtacacgctg tgcgaccgct acggcctgta tgtggtggat   8760
gaagccaata ttgaaaccca cggcatggtg ccaatgaatc gtctgaccga tgatccgcgc   8820
tggctaccgg cgatgagcga acgcgtaacg caatggtgc agcgcgatcg taatcacccg   8880
agtgtgatca tctggtcgct ggggaatgaa tcaggccacg cgctaatca cgacgcgctg   8940
tatcgctgga tcaaatctgt cgatcctcc cgcccggtgc agtatgaagg cggcggagcc   9000
gacaccacgg ccaccgatat tatttgcccg atgtacgcgc gcgtggatga agaccagccc   9060
ttcccggctg tgccgaaatg gtccatcaaa aaatggcttt cgctacctgg agagacgcgc   9120
ccgctgatcc tttgcgaata cgcccacgcg atgggtaaca gtcttggcgg tttcgctaaa   9180
tactggcagg cgtttcgtca gtatccccgt ttacagggcg gcttcgtctg ggactgggtg   9240
gatcagtcgc tgattaaata tgatgaaaac ggcaacccgt ggtcggctta cggcggtgat   9300
```

```
tttggcgata cgccgaacga tcgccagttc tgtatgaacg gtctggtctt tgccgaccgc   9360
acgccgcatc cagcgctgac ggaagcaaaa caccagcagc agttttttcca gttccgttta   9420 tccgggcaaa ccatcgaagt gaccagcgaa tacctgttcc gtcatagcga taacgagctc   9480
ctgcactgga tggtggcgct ggatggtaag ccgctggcaa gcggtgaagt gcctctggat   9540
gtcgctccac aaggtaaaca gttgattgaa ctgcctgaac taccgcagcc ggagagcgcc   9600
gggcaactct ggctcacagt acgcgtagtg caaccgaacg cgaccgcatg gtcagaagcc   9660
gggcacatca gcgcctggca gcagtggcgt ctggcggaaa acctcagtgt gacgctcccc   9720
gccgcgtccc acgccatccc gcatctgacc accagcgaaa tggatttttg catcgagctg   9780
ggtaataagc gttggcaatt taaccgccag tcaggctttc tttcacagat gtggattggc   9840
gataaaaaac aactgctgac gccgctgcgc gatcagttca cccgtgcacc gctggataac   9900
gacattggcg taagtgaagc gacccgcatt gaccctaacg cctgggtcga acgctggaag   9960
gcggcgggcc attaccaggc cgaagcagcg ttgttgcagt gcacggcaga tacacttgct  10020
gatgcggtgc tgattacgac cgctcacgcg tggcagcatc aggggaaaac cttatttatc  10080
agccggaaaa cctaccggat tgatggtagt ggtcaaatgg cgattaccgt tgatgttgaa  10140
gtggcgagcg ataccgcca tccggcgcgg attggcctga actgccagct ggcgcaggta  10200
gcagagcggg taaactggct cggattaggg ccgcaagaaa actatcccga ccgccttact  10260
gccgcctgtt ttgaccgctg ggatctgcca ttgtcagaca tgtataccc gtacgtcttc  10320 ccgagcgaaa acggtctgcg ctgcgggacg cgcgaattga attatggccc acaccagtgg  10380
cgcggcgact tccagttcaa catcagccgc tacagtcaac agcaactgat ggaaaccagc  10440
catcgccatc tgctgcacgc ggaagaaggc acatggctga atatcgacgg tttccatatg  10500
gggattggtg gcgacgactc ctggagcccg tcagtatcgg cggaattcca gctgagcgcc  10560
ggtcgctacc attaccagtt ggtctggtgt caaaataat aataaccggg caggccatgt  10620
ctgcccgtat ttcgcgtaag gaaatccatt atgtactatt taaaaaacac aaacttttgg  10680
atgttcggtt tattctttttt cttttacttt tttatcatgg gagcctactt cccgttttt   10740 ccgattggc tacatgacat caaccatatc agcaaaagtg atacgggtat tattttttgcc  10800 gctatttctc tgttctcgct attattccaa ccgctgtttg gtctgctttc tgacaaactc  10860
ggctcgagct gtgccttcta gttgccagcc atctgttgtt tgcccctccc ccgtgccttc  10920
cttgaccctg gaaggtgcca ctcccactgt cctttcctaa taaaatgagg aaattgcatc  10980
gcattgtctg agtaggtgtc attctattct gggggtggg gtggggcagg acagcaaggg  11040
ggaggattgg gaagacaata gcaggcatgc tggggatgcg gtgggctcta tggcttctga  11100
ggcggaaaga accagctggg gctctagcta gcatatacct gcagggaatt cctaaacaga  11160
gcaattaggt aagaaaatga agaaaaggt atccaattat gaaggaagaa gtaaaactat  11220
ttctatttgc agatgacatg actgtataca agaaaatcc caataatcc acacaaaaac  11280 tagtagagtt aataagcaaa ttcaacaaat ttcagggtac aaaatcagtt gtgtttctat  11340
acacaaaccc acaatgaaca ataaaaaaag gaaactaaga aaacaatttc ctttataata  11400
acatcccaaa gaataaaata catgggacta aatttaacca aggaagtgaa agaattgtac  11460
actaaaaacc acaaataatt gctgattaaa tggaaagatg tcccatgttc acggataggg  11520
atacttaata ttgttaaatg gcaatacttc ccaaagcaat ctatagattc aatgcaatct  11580
ctgtcaaaat ttcaaatggt cttctttgct gaaatgggaa agccaatcct aaaattcata  11640
```

```
tgtaattcca taggatccaa aaaagcaaaa ccaatattga aatagaaaaa caaagttgga    11700
gtacttacac ttctcaattt caaaacttac aagctacagt aattaaaaca gcatggcaaa    11760
ggcataagga tagacatatg gatcaatgga atagattcag agtccagaaa taaacacaac    11820
atttatggcc atttgatttt tgataaggat tgtcaagggg gtcttgaaca ttcagtgggg    11880
aaagaataat atcttcaaca agtggtgctg gaacaattgg atagccatgt gcaaaatact    11940
ctagtagact cctaccttat gtcacataca ataattaatt taaataaat caatcctaaa    12000 tataagggcc aaaaccataa aactcttaga agaaaacagg cgtaatcttc atggtttctg    12060
atttgtcaat ggattcttaa atttgacacc aaaagcacaa gcaacaaaag ataaaattga    12120
tacatttgaa tgcataaaat tttttttaatt tgcacatgaa atgacaatat caagaaaatg    12180
aaaagacaat ctgcagaatg ggagaaaata tttacaagcc acatatctga taagggctga    12240
gtatccagaa tatataacaa actcttccag ctcaacaatg aaaacaaaaa caacgcaatt    12300
ttaagaatgg gcaaaggact tgaatcaaca tttctccaaa gaagatatgc gaataaccag    12360
caaacacatg aagtgatgct caacatcatt actcataaag gaaatgtgaa tcaaaaccat    12420
atgacatact actttacacc cattaggatg aagataataa ttttaaaata caagtgtca    12480 gcaaggatgc agagaaatag gaactttcct atgttgctga taagcaatgc aaaaggatac    12540
aaccactgtg gaaaacagtt tggtggttcc ttaaaaaatt aaaaatagga ttattgtata    12600
actcagaaat tccaaaagta tatatatttg gtatatatcc aaaagaactg aaaacatatt    12660
gttcatgcag aaatttgtac acaaatgctt attattgctg cattagctac aatagccaaa    12720
agatgaaaac aacccaaatg tccattgaca gatgaacaaa taacttgtgg tataaacata    12780
caatgggaat attattttc catcaaaaag aacgaatact ggcatgtgct acagcttgta    12840
tgaatctcag aaacattatt acaagtgaat gtagccagcc acaacaggcc atgtattgtg    12900
tgattccgtt tatatgaaat atccagaggt ggtggttgca gattttgaat gtgctaaatg    12960
tcactgaatt gaatacttta aaatggttaa ttgtatgtta tgtgaatttt acctcaattt    13020
tttaaatggg tcataaactt atgtttagca taatccccctt ttaattttaa aaaatgcaga    13080
tattacatga gaaaaaatgt gctagagcat atttcaagac attaaagatg ttatcagtg    13140 aatgatgaga aattaggtaa tgtttattat tttcgctttg ctaaaattat ttaaaaatta    13200
cttgcatatt aaattttta atgcctagga aagaaagact atagttgtat tgactaagat    13260
ttctacgagc atggggaaaa tgcttaattt gtagggttaa tcaaggataa aataaattgc    13320
attgtatgta caatgtgatc ccaagtattt aaaacacact gcttatggta acagtcagtc    13380
tgtgggagac aggttaaaaa gtgatatttt cccttcctac tctccaaatt ttcttaacaa    13440
acatatatta tgactataat cagaaaaaat tatttttaaa acgtctacta tggggcaagc    13500
taggttcaaa aaatagaagt ttgataaatg tagttggctt gctattgaca aggaagacgt    13560
ttacactgga attcgggccc tatatggcca tcatggccat atagcgatcg ctatatgcta    13620
gcgataacaa tttcacacag gaaacagcta tgaccatgat tacgccaagc tctagctaga    13680
ggtcgacggt aatggcaggg cctgccgccc cgacgttggc tgcgagccct gggccttcac    13740
ccgaacttgg ggggtgggt ggggaaaagg aagaaacgcg ggcgtattgg ccccaatggg    13800
gtctcggtgg ggtatcgaca gagtgccagc cctgggaccg aacccgcgt ttatgaacaa    13860 acgacccaac acccgtgcgt tttattctgt cttttttattg ccgtcatagc gcgggttcct    13920
tccggtattg tctccttccg tgtttcagtt agcctccccc gttaaactc attactaacc    13980 ggttttagtc tttcttctcg tagacttcaa acttatactt gatgccttt tcctcctgga    14040
```

```
cctcagagag  gacgcctggg  tattctggga  gaagtttata  tttccccaaa  tcaatttctg    14100
ggaaaaacgt  gtcactttca  aattcctgca  tgatccttgt  cacaaagagt  ctgaggtggc    14160
ctggttgatt  catggcttcc  tggtaaacag  aactgcctcc  gactatccaa  accatgtcta    14220
ctttacttgc  caattccggt  tgttcaataa  gtcttaaggc  atcatccaaa  cttttggcaa    14280
gaaaatgagc  tcctcgtggt  ggttctttga  gttctctact  gagaactata  ttaattctgt    14340
cctttaaagg  tcgattcttc  tcaggaatgg  agaaccaggt  tttcctaccc  ataatcacca    14400
gattctgttt  accttccact  gaagaggttg  tggtcattct  ttggaagtac  ttgaactcgt    14460
tcctgagcgg  aggccagggt  aggtctccgt  tcttgccaat  ccccatattt  tgggacacgg    14520
cgacgatgca  gttcaatggt  cgaaccatga  tggcgcgaaa  cgatcctcat  cctgtctctt    14580
gatcagatcc  gaaaatggat  atacaagctc  ccgggagctt  tttgcaaaag  cctaggcctc    14640 caaaaagcc  tcctcactac  ttctggaata  gctcagaggc  agaggcggcc  tcggcctctg     14700
cataaataaa  aaaaattagt  cagccatggg  gcggagaatg  ggcggaactg  ggcggagtta    14760
ggggcgggat  gggcggagtt  aggggcggga  ctatggttgc  tgactaattg  agatgcatgc    14820
tttgcatact  tctgcctgct  ggggagcctg  gggactttcc  acacctaac   tgacacacat    14880 tccacag                                                                   14887

<210> SEQ ID NO 5
<211> LENGTH: 30
<212> TYPE: DNA
<213> ORGANISM: Artificial Sequence
<220> FEATURE:
<223> OTHER INFORMATION: Cs5S300F primer

<400> SEQUENCE: 5
attcttcagc acctccttaa ttttctccc                                30

<210> SEQ ID NO 6
<211> LENGTH: 30
<212> TYPE: DNA
<213> ORGANISM: Artificial Sequence
<220> FEATURE:
<223> OTHER INFORMATION: Cs5S300R primer

<400> SEQUENCE: 6
ccaggcagcc aaagatcagt agttgtgttg                                30

<210> SEQ ID NO 7
<211> LENGTH: 28
<212> TYPE: DNA
<213> ORGANISM: Artificial Sequence
<220> FEATURE:
<223> OTHER INFORMATION: 2kCspSF primer

<400> SEQUENCE: 7
tggttccttc attggaaaag gaaaacac                                  28

<210> SEQ ID NO 8
<211> LENGTH: 27
<212> TYPE: DNA
<213> ORGANISM: Artificial Sequence
<220> FEATURE:
<223> OTHER INFORMATION: 2kCspSR primer

<400> SEQUENCE: 8
tccgctgagg ctgtgcccac agccacc                                   27
```

<210> SEQ ID NO 9
<211> LENGTH: 27
<212> TYPE: DNA
<213> ORGANISM: Artificial Sequence
<220> FEATURE:
<223> OTHER INFORMATION: CspSF primer

<400> SEQUENCE: 9
ggatcccatt ctccttgatg tactaat                               27

<210> SEQ ID NO 10
<211> LENGTH: 28
<212> TYPE: DNA
<213> ORGANISM: Artificial Sequence
<220> FEATURE:
<223> OTHER INFORMATION: CspSR primer

<400> SEQUENCE: 10
gaattcaaac aactcaatag caagaaac                              28

<210> SEQ ID NO 11
<211> LENGTH: 38
<212> TYPE: DNA
<213> ORGANISM: Artificial Sequence
<220> FEATURE:
<223> OTHER INFORMATION: Bg5MF-100F-NheI primer

<400> SEQUENCE: 11
aattgctagc ttgtattctg tttcgtgagg caaggttt                   38

<210> SEQ ID NO 12
<211> LENGTH: 38
<212> TYPE: DNA
<213> ORGANISM: Artificial Sequence
<220> FEATURE:
<223> OTHER INFORMATION: Bg5MR-100R-XhoI primer

<400> SEQUENCE: 12
aattctcgag ttcctctcta tgttggctca aatgtcct                   38

<210> SEQ ID NO 13
<211> LENGTH: 65
<212> TYPE: DNA
<213> ORGANISM: Artificial Sequence
<220> FEATURE:
<223> OTHER INFORMATION: V6_F primer

<400> SEQUENCE: 13
aagcttggat ccgaattcat cgatggccgg ccggtaccct cgagctgtgc cttctagttg   60
ccagc                                                       65

<210> SEQ ID NO 14
<211> LENGTH: 30
<212> TYPE: DNA
<213> ORGANISM: Artificial Sequence
<220> FEATURE:
<223> OTHER INFORMATION: V6_R primer

<400> SEQUENCE: 14
gctagctaga gccccagctg gttctttccg                            30

<210> SEQ ID NO 15
<211> LENGTH: 46
<212> TYPE: DNA
<213> ORGANISM: Artificial Sequence

```
<220> FEATURE:
<223> OTHER INFORMATION: PsvApaDraF primer

<400> SEQUENCE: 15
aaaattgggc cccactacgt gctgtggaat gtgtgtcagt tagggt          46

<210> SEQ ID NO 16
<211> LENGTH: 43
<212> TYPE: DNA
<213> ORGANISM: Artificial Sequence
<220> FEATURE:
<223> OTHER INFORMATION: PsvKzDHR primer

<400> SEQUENCE: 16
tggtcgaacc atgatggcgc gaaacgatcc tcatcctgtc tct             43

<210> SEQ ID NO 17
<211> LENGTH: 43
<212> TYPE: DNA
<213> ORGANISM: Artificial Sequence
<220> FEATURE:
<223> OTHER INFORMATION: DHKzPsvF primer

<400> SEQUENCE: 17
ggatcgtttc gcgccatcat ggttcgacca ttgaactgca tcg             43

<210> SEQ ID NO 18
<211> LENGTH: 43
<212> TYPE: DNA
<213> ORGANISM: Artificial Sequence
<220> FEATURE:
<223> OTHER INFORMATION: TKNheNdeR primer

<400> SEQUENCE: 18
tgtgtgcata tggctagcga taacaatttc acacaggaaa cag             43

<210> SEQ ID NO 19
<211> LENGTH: 72
<212> TYPE: DNA
<213> ORGANISM: Artificial Sequence
<220> FEATURE:
<223> OTHER INFORMATION: enhancer

<400> SEQUENCE: 19
ggtgtggaaa gtccccaggc tccccagcag gcagaagtat gcaaagcatg catctcaatt    60
agtcagcaac ca                                                        72

<210> SEQ ID NO 20
<211> LENGTH: 52
<212> TYPE: DNA
<213> ORGANISM: Artificial Sequence
<220> FEATURE:
<223> OTHER INFORMATION: NhAsE1F primer

<400> SEQUENCE: 20
aattgctagc atatagcgat cgcgcaggac agcttccgac agcagggcca gg            52

<210> SEQ ID NO 21
<211> LENGTH: 75
<212> TYPE: DNA
<213> ORGANISM: Artificial Sequence
<220> FEATURE:
<223> OTHER INFORMATION: BbPsSbNhE1R primer

<400> SEQUENCE: 21
```

```
aattgctagc atatacctgc aggtatatgg gcccatatag ctgaggttga atgagaatat    60
cactgtccca gacac                                                    75
```

<210> SEQ ID NO 22
<211> LENGTH: 37
<212> TYPE: DNA
<213> ORGANISM: Artificial Sequence
<220> FEATURE:
<223> OTHER INFORMATION: galHinF primer

<400> SEQUENCE: 22

```
aattaagctt ctcgcgcaac ctattttccc ctcgaac                            37
```

<210> SEQ ID NO 23
<211> LENGTH: 37
<212> TYPE: DNA
<213> ORGANISM: Artificial Sequence
<220> FEATURE:
<223> OTHER INFORMATION: galXhoR primer

<400> SEQUENCE: 23

```
aattctcgag ccgagtttgt cagaaagcag accaaac                            37
```

<210> SEQ ID NO 24
<211> LENGTH: 51
<212> TYPE: DNA
<213> ORGANISM: Artificial Sequence
<220> FEATURE:
<223> OTHER INFORMATION: NhSbE1F primer

<400> SEQUENCE: 24

```
aattgctagc atatacctgc aggttgaatg agaatatcac tgtcccagac a            51
```

<210> SEQ ID NO 25
<211> LENGTH: 80
<212> TYPE: DNA
<213> ORGANISM: Artificial Sequence
<220> FEATURE:
<223> OTHER INFORMATION: NhAsSfPsE1R primer

<400> SEQUENCE: 25

```
aattgctagc atatagcgat cgctatatgg ccatgatggc catatagggc ccaggacagc   60
ttccgacagc agggccaggc                                               80
```

<210> SEQ ID NO 26
<211> LENGTH: 39
<212> TYPE: DNA
<213> ORGANISM: Artificial Sequence
<220> FEATURE:
<223> OTHER INFORMATION: cs3sSbf1F primer

<400> SEQUENCE: 26

```
aattcctgca ggggatccca ttctccttga tgtactaat                          39
```

<210> SEQ ID NO 27
<211> LENGTH: 38
<212> TYPE: DNA
<213> ORGANISM: Artificial Sequence
<220> FEATURE:
<223> OTHER INFORMATION: cs3sPsp1R primer

<400> SEQUENCE: 27

```
aattgggccc gaattcaaac aactcaatag caagaaac                           38
```

<210> SEQ ID NO 28
<211> LENGTH: 40
<212> TYPE: DNA
<213> ORGANISM: Artificial Sequence
<220> FEATURE:
<223> OTHER INFORMATION: cs5sSbf1F primer

<400> SEQUENCE: 28
aattcctgca gggaattcct aaacagagca attaggtaag        40

<210> SEQ ID NO 29
<211> LENGTH: 37
<212> TYPE: DNA
<213> ORGANISM: Artificial Sequence
<220> FEATURE:
<223> OTHER INFORMATION: cs5sPsp1R primer

<400> SEQUENCE: 29
aattgggccc gaattccagt gtaaacgtct tccttgt        37

<210> SEQ ID NO 30
<211> LENGTH: 40
<212> TYPE: DNA
<213> ORGANISM: Artificial Sequence
<220> FEATURE:
<223> OTHER INFORMATION: glmSbf1F primer

<400> SEQUENCE: 30
aattcctgca ggttgtattc tgtttcgtga ggcaaggttt        40

<210> SEQ ID NO 31
<211> LENGTH: 38
<212> TYPE: DNA
<213> ORGANISM: Artificial Sequence
<220> FEATURE:
<223> OTHER INFORMATION: glmPsp1R primer

<400> SEQUENCE: 31
aattgggccc ttcctctcta tgttggctca aatgtcct        38

<210> SEQ ID NO 32
<211> LENGTH: 37
<212> TYPE: DNA
<213> ORGANISM: Artificial Sequence
<220> FEATURE:
<223> OTHER INFORMATION: cs3sPsp2F primer

<400> SEQUENCE: 32
aattgggccc ggatcccatt ctccttgatg tactaat        37

<210> SEQ ID NO 33
<211> LENGTH: 45
<212> TYPE: DNA
<213> ORGANISM: Artificial Sequence
<220> FEATURE:
<223> OTHER INFORMATION: cs3sSfi2R primer

<400> SEQUENCE: 33
aattggccat gatggccgaa ttcaaacaac tcaatagcaa gaaac        45

<210> SEQ ID NO 34
<211> LENGTH: 38
<212> TYPE: DNA
<213> ORGANISM: Artificial Sequence
<220> FEATURE:
<223> OTHER INFORMATION: cs5sPsp2F primer

```
<400> SEQUENCE: 34
aattgggccc gaattcctaa acagagcaat taggtaag                              38

<210> SEQ ID NO 35
<211> LENGTH: 44
<212> TYPE: DNA
<213> ORGANISM: Artificial Sequence
<220> FEATURE:
<223> OTHER INFORMATION: cs5sSfi2R primer

<400> SEQUENCE: 35
aattggccat gatggccgaa ttccagtgta aacgtcttcc ttgt                       44

<210> SEQ ID NO 36
<211> LENGTH: 38
<212> TYPE: DNA
<213> ORGANISM: Artificial Sequence
<220> FEATURE:
<223> OTHER INFORMATION: cs5sBgl3F primer

<400> SEQUENCE: 36
aattagatct gaattcctaa acagagcaat taggtaag                              38

<210> SEQ ID NO 37
<211> LENGTH: 37
<212> TYPE: DNA
<213> ORGANISM: Artificial Sequence
<220> FEATURE:
<223> OTHER INFORMATION: cs5sBgl3R primer

<400> SEQUENCE: 37
aattagatct gaattccagt gtaaacgtct tccttgt                               37

<210> SEQ ID NO 38
<211> LENGTH: 25
<212> TYPE: DNA
<213> ORGANISM: Artificial Sequence
<220> FEATURE:
<223> OTHER INFORMATION: IE1ATGF primer

<400> SEQUENCE: 38 atggggtgc acgaatgtcc tgcct                                             25

<210> SEQ ID NO 39
<211> LENGTH: 26
<212> TYPE: DNA
<213> ORGANISM: Artificial Sequence
<220> FEATURE:
<223> OTHER INFORMATION: IE1TGAR primer

<400> SEQUENCE: 39
tcatctgtcc cctgtcctgc aggcct                                           26

<210> SEQ ID NO 40
<211> LENGTH: 18
<212> TYPE: DNA
<213> ORGANISM: Artificial Sequence
<220> FEATURE:
<223> OTHER INFORMATION: M13R primer

<400> SEQUENCE: 40
gaaacagcta tgaccatg                                                    18

<210> SEQ ID NO 41
<211> LENGTH: 39
```

<212> TYPE: DNA
<213> ORGANISM: Artificial Sequence
<220> FEATURE:
<223> OTHER INFORMATION: IA1g1R primer

<400> SEQUENCE: 41
ctcattcaag ctgcatgttt cattacagcc cgtcgtgat         39

<210> SEQ ID NO 42
<211> LENGTH: 20
<212> TYPE: DNA
<213> ORGANISM: Artificial Sequence
<220> FEATURE:
<223> OTHER INFORMATION: M13F primer

<400> SEQUENCE: 42
cagggttttc ccagtcacga         20

<210> SEQ ID NO 43
<211> LENGTH: 39
<212> TYPE: DNA
<213> ORGANISM: Artificial Sequence
<220> FEATURE:
<223> OTHER INFORMATION: IA1g1F primer

<400> SEQUENCE: 43
atcacgacgg gctgtaatga acatgcagc ttgaatgag         39

<210> SEQ ID NO 44
<211> LENGTH: 42
<212> TYPE: DNA
<213> ORGANISM: Artificial Sequence
<220> FEATURE:
<223> OTHER INFORMATION: IA1G2R primer

<400> SEQUENCE: 44
cacatgcagc tgcagtgtct cattcacctg ggaagagttg ac         42

<210> SEQ ID NO 45
<211> LENGTH: 42
<212> TYPE: DNA
<213> ORGANISM: Artificial Sequence
<220> FEATURE:
<223> OTHER INFORMATION: IA1G2F primer

<400> SEQUENCE: 45
gtcaactctt cccaggtgaa tgagacactg cagctgcatg tg         42

<210> SEQ ID NO 46
<211> LENGTH: 41
<212> TYPE: DNA
<213> ORGANISM: Artificial Sequence
<220> FEATURE:
<223> OTHER INFORMATION: IE1KzATGHinF primer

<400> SEQUENCE: 46
aattaagctt gccaccatgg gggtgcacga atgtcctgcc t         41

<210> SEQ ID NO 47
<211> LENGTH: 36
<212> TYPE: DNA
<213> ORGANISM: Artificial Sequence
<220> FEATURE:
<223> OTHER INFORMATION: IE1TGAXhoR primer

<400> SEQUENCE: 47

```
aattctcgag tcatctgtcc cctgtcctgc aggcct                              36
```

<210> SEQ ID NO 48
<211> LENGTH: 51
<212> TYPE: DNA
<213> ORGANISM: Artificial Sequence
<220> FEATURE:
<223> OTHER INFORMATION: NhAsf1F primer

<400> SEQUENCE: 48

```
aattgctagc atataggcgc gccaacttga ttagggtgat ggttcacgta g             51
```

<210> SEQ ID NO 49
<211> LENGTH: 73
<212> TYPE: DNA
<213> ORGANISM: Artificial Sequence
<220> FEATURE:
<223> OTHER INFORMATION: NhClPaPsf1R primer

<400> SEQUENCE: 49

```
aattgctagc atataatcga ttatatttaa ttaaatatag ggcccttgag tgttgttcca    60
gtttggaaca aga                                                       73
```

<210> SEQ ID NO 50
<211> LENGTH: 39
<212> TYPE: DNA
<213> ORGANISM: Artificial Sequence
<220> FEATURE:
<223> OTHER INFORMATION: cs3sAsc1F primer

<400> SEQUENCE: 50

```
aattggcgcg ccggatccca ttctccttga tgtactaat                           39
```

<210> SEQ ID NO 51
<211> LENGTH: 38
<212> TYPE: DNA
<213> ORGANISM: Artificial Sequence
<220> FEATURE:
<223> OTHER INFORMATION: cs3sPsp1R primer

<400> SEQUENCE: 51

```
aattgggccc gaattcaaac aactcaatag caagaaac                            38
```

<210> SEQ ID NO 52
<211> LENGTH: 40
<212> TYPE: DNA
<213> ORGANISM: Artificial Sequence
<220> FEATURE:
<223> OTHER INFORMATION: cs5sAsc1F primer

<400> SEQUENCE: 52

```
aattggcgcg ccgaattcct aaacagagca attaggtaag                          40
```

<210> SEQ ID NO 53
<211> LENGTH: 37
<212> TYPE: DNA
<213> ORGANISM: Artificial Sequence
<220> FEATURE:
<223> OTHER INFORMATION: cs5sPsp1R primer

<400> SEQUENCE: 53

```
aattgggccc gaattccagt gtaaacgtct tccttgt                             37
```

<210> SEQ ID NO 54
<211> LENGTH: 61

```
<212> TYPE: DNA
<213> ORGANISM: Artificial Sequence
<220> FEATURE:
<223> OTHER INFORMATION: V1_F primer

<400> SEQUENCE: 54
aagcttcctc agcatcgatg gccggccgga tccctgtgcc ttctagttgc cagccatctg      60
t                                                                      61

<210> SEQ ID NO 55
<211> LENGTH: 30
<212> TYPE: DNA
<213> ORGANISM: Artificial Sequence
<220> FEATURE:
<223> OTHER INFORMATION: V1_R primer

<400> SEQUENCE: 55
tagagcccca gctggttctt tccgcctcag                                       30

<210> SEQ ID NO 56
<211> LENGTH: 60
<212> TYPE: DNA
<213> ORGANISM: Artificial Sequence
<220> FEATURE:
<223> OTHER INFORMATION: V2_F primer

<400> SEQUENCE: 56
gaattctgta caggtacccc tgcaggctcg agctgtgcct tctagttgcc agccatctgt      60

<210> SEQ ID NO 57
<211> LENGTH: 30
<212> TYPE: DNA
<213> ORGANISM: Artificial Sequence
<220> FEATURE:
<223> OTHER INFORMATION: V2_R primer

<400> SEQUENCE: 57
tagagcccca gctggttctt tccgcctcag                                       30

<210> SEQ ID NO 58
<211> LENGTH: 37
<212> TYPE: DNA
<213> ORGANISM: Artificial Sequence
<220> FEATURE:
<223> OTHER INFORMATION: PcmvAgeF primer

<400> SEQUENCE: 58
aatctgaccg gtgttaggcg ttttgcgctg cttcgcg                               37

<210> SEQ ID NO 59
<211> LENGTH: 51
<212> TYPE: DNA
<213> ORGANISM: Artificial Sequence
<220> FEATURE:
<223> OTHER INFORMATION: BGHNheDraR primer

<400> SEQUENCE: 59
ttactacact acgtggatcg agctagctag agccccagct ggttctttcc g               51

<210> SEQ ID NO 60
<211> LENGTH: 63
<212> TYPE: DNA
<213> ORGANISM: Artificial Sequence
<220> FEATURE:
<223> OTHER INFORMATION: H1ssF primer
```

```
<400> SEQUENCE: 60
ctcttcttgg tagcaacagc tacaggtgtc cactccgagg tccaactggt cgaaagcggt    60
gga                                                                 63

<210> SEQ ID NO 61
<211> LENGTH: 40
<212> TYPE: DNA
<213> ORGANISM: Artificial Sequence
<220> FEATURE:
<223> OTHER INFORMATION: H1TGAXhoR primer

<400> SEQUENCE: 61
aattctcgag tcatttaccc ggagacaggg agaggctctt                          40

<210> SEQ ID NO 62
<211> LENGTH: 63
<212> TYPE: DNA
<213> ORGANISM: Artificial Sequence
<220> FEATURE:
<223> OTHER INFORMATION: H1ssEcoF primer

<400> SEQUENCE: 62
aattgaattc gccaccatgg gatggagctg tatcatcctc ttcttggtag caacagctac    60
agg                                                                 63

<210> SEQ ID NO 63
<211> LENGTH: 63
<212> TYPE: DNA
<213> ORGANISM: Artificial Sequence
<220> FEATURE:
<223> OTHER INFORMATION: H2ssF primer

<400> SEQUENCE: 63
ctcttcttgg tagcaacagc tacaggtgtc cactccgata tccagatgac ccagagtccc    60
tct                                                                 63

<210> SEQ ID NO 64
<211> LENGTH: 40
<212> TYPE: DNA
<213> ORGANISM: Artificial Sequence
<220> FEATURE:
<223> OTHER INFORMATION: H2TGABamR primer

<400> SEQUENCE: 64
aattggatcc tcaacactct cccctgttga agctctttgt                          40

<210> SEQ ID NO 65
<211> LENGTH: 63
<212> TYPE: DNA
<213> ORGANISM: Artificial Sequence
<220> FEATURE:
<223> OTHER INFORMATION: H2ssHinF primer

<400> SEQUENCE: 65
aattaagctt gccaccatgg gatggagctg tatcatcctc ttcttggtag caacagctac    60
agg                                                                 63
```

EXPRESSION VECTOR FOR ANIMAL CELLS INCLUDING CSP-B 5'-SAR FACTOR AND METHOD FOR PRODUCING RECOMBINANT PROTEINS USING SAME

CROSS-REFERENCE TO RELATED APPLICATIONS

This application is the U.S. national stage filing under 35 U.S.C. §371 of International Application PCT/KR2012/003995, filed May 21, 2012, which claims priority from Korean Patent Application 10-2011-0056685, filed Jun. 13, 2011.

TECHNICAL FIELD

The present invention relates to an expression vector for animal cells, including a 5'-scaffold or matrix attachment region (5'-SAR) of cytotoxic serine protease-B (CSP-B), and methods for producing recombinant proteins using the expression vectors.

BACKGROUND ART

The introduction of foreign genes coding recombinant proteins into animal cells such as Chinese hamster ovary (CHO) cells can produce protein drugs for clinical treatment.

A novel erythropoiesis stimulating protein (NESP), which is an erythropoiesis-stimulating factor, is also called Darbepoetin alfa, and is a protein drug obtained by adding two N-linked sugar chains to naturally occurring erythropoietin through genetic modification (Egrie and Browne, *Br. J. Cancer*, 84 Suppl. 1:3-10 (2001)). NESP promotes red blood cell production by stimulating hematopoietic stem cells and facilitating their differentiation into erythrocytes. Since the serum half-life of NESP is three times longer than that of the existing recombinant erythropoietin, equivalent therapeutic effect can be expected with fewer administrations when treating anemia of patients with chronic kidney disease.

Trastuzumab as an anti-malignant tumor agent is a humanized monoclonal antibody prepared using recombinant DNA technology, and selectively acts on human epidermal growth factor receptor 2 (HER2) on cell surfaces. HER2 overexpression is confirmed in 25~30% of primary breast cancers and trastuzumab suppresses the proliferation of HER2-overexpressed human tumor cells.

Expression levels of foreign genes may be varied depending on their insertion sites in the animal cell chromosomes since foreign gene expression is influenced by surrounding regulator elements or the chromatin structure (Zahn-Zabal et al., *J. Biotechnol*, 87, 29-42 (2001)).

When chromatin factors that prevent surrounding chromatins from influencing foreign gene expression are used, the suppression of gene expression depending on the position (position effect) can be overcome and the possibility of isolation of animal cell clones that highly express recombinant proteins can be increased, thereby decreasing the preparation time of cell lines for producing drugs. Attempts to produce stable cell lines by using chromatin factors that can overcome the suppression of gene expression depending on the position have been made. The factors therefor are boundary element (BE), scaffold or matrix attachment region (SAR/MAR), locus control region (LCR), and the like.

SAR also called MAR is 300~3000-bp DNA element. It has been known that SAR allows the chromatin to attach to proteins of the nuclear matrix and controls gene expression (Makrides (Ed.), *Gene Transfer and Expression in Mammalian Cells*. Elsevier. Chapter 10 (2003)). In addition, SAR can improve expression of foreign genes in transfected cell lines (Poljak et al., *Nucleic Acids Res*, 22, 4386-4394 (1994); Kalos and Fournier, *Mol. Cell. Biol*, 15, 198-207 (2005)).

Zahn-Zabal et al. had produced stable cells by introducing a chicken lysozyme 5'-MAR into a luciferase expression vector and transfecting CHO cells with the vector (Zahn-Zabal et al., *J. Biotechnol*, 87, 29-42 (2001)). The stable cells transfected with a vector containing lysozyme 5'-MAR exhibited a higher luciferase expression level as compared with stable cells transfected with a vector not containing MAR. In addition, the vector containing two copies of MAR exhibited a higher luciferase expression level than the vector containing one copy of lysozyme 5'-MAR. This result shows that the introduction of MAR into the animal cell expression vector can increase the target protein expression level.

Korean Patent Application No. 2000-0043996 discloses that the animal cell expression vector includes human β-globin MAR so that gene expression suppression occurring when foreign genes are introduced into animal cells can be overcome. This patent describes that, besides the human β-globin MAR, human interferon-β MAR (GenBank Accession #M83137) and CSP-B 3'-SAR (GenBank Accession #M62716) are used, and these three SARs/MARs can improve the expression level of β-galactosidase, which is a target protein. Further, this patent discloses that the β-globin MAR had excellent effects as compared with the interferon-β MAR or the CSP-B 3'-SAR.

Korean Patent Application No. 2001-0079227 discloses that the introduction of human interferon-β MAR into the animal cell expression vector can improve foreign gene expression and lead to efficient expression of recombinant proteins. In addition, Korean Patent Application No. 2007-0108451 discloses that the animal cell expression vector including two copies of human β-globin MAR can further improve the target protein expression level as compared with the vector including one copy of human β-globin MAR. This patent describes comparison results between one copy and two copies of MAR factors, but not comparison results between two copies and three copies of MAR factors.

Hanson and Ley found CSP-B 5'-SAR and CSP-B 3'-SAR from approximately 70 kb of the human chromosome 14q11.2 hematopoietic serine protease gene cluster and obtained their nucleotide sequences, and verified that these SARs bind to scaffolds derived from the cellular nucleus through in vitro experiment (Hanson and Ley, *Blood*, 79, 610-618 (1992)).

The CSP-B 5'-SAR and CSP-B 3'-SAR are registered as GenBank Accession #M62717 and GenBank Accession #M62716, respectively. They are 2429-bp long and 1233-bp long, respectively, and thus the CSP-B 5'-SAR is two folds longer than the 3'-SAR. Human chromosome 14 DNA sequence is registered as GenBank Accession #AL136018. In this sequence, the length between a transcription initiation codon for a gene coding the CSP-B protein and the 5'-SAR located upstream thereof is 1195 bp, and the length between a transcription termination codon of the gene for coding the CSP-B protein and the 3'-SAR located downstream thereof is 4543 bp.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have made efforts to develop vectors capable of efficiently producing recombinant proteins in animal cells. As a result, the present inventors have established that recombinant proteins can be produced at excellent production efficiency when cytotoxic serine protease-B (CSP-B) 5'-scaffold or matrix attachment region (SAR) is incorporated in the vector, and then completed the present invention.

Therefore, an aspect of the present invention is to provide expression vectors for animal cells.

Another aspect of the present invention is to provide animal cells transfected with the expression vectors.

Still another aspect of the present invention is to provide a method for producing recombinant proteins.

Other purposes and advantages of the present invention will become clarified by the following detailed description of invention, claims, and drawings.

Technical Solution

In accordance with an aspect of the present invention, there is provided an expression vector for animal cells, the expression vector including: (a) a 5'-scaffold or matrix attachment region (5'-SAR) of cytotoxic serine protease-B (CSP-B); (b) a promoter operable in animal cells; and (c) a polyadenylation sequence.

The present inventors have made efforts to develop vectors capable of efficiently producing recombinant proteins in animal cells. As a result, the present inventors have established that recombinant proteins can be produced at excellent production efficiency when the 5'-scaffold or matrix attachment region (5'-SAR) of cytotoxic serine protease-B (CSP-B) is incorporated in the vector.

The expression vector for animal cells of the present invention includes CSP-B 5'-SAR; a promoter operable in animal cells; and a polyadenylation sequence.

The present invention is mainly characterized by using a vector including CSP-B 5'-SAR. CSP-B 5'-SAR used herein preferably includes a nucleotide sequence registered as GenBank accession #M62717, and its exemplary nucleotide sequence is described in SEQ ID NO: 1.

CSP-B 5'-SAR significantly increases the efficiency in production of recombinant proteins in the expression vector.

CSP-B 5'-SAR may be located upstream or downstream of the nucleotide sequence coding a protein to be expressed, and is preferably located downstream of the nucleotide sequence.

According to a preferable embodiment of the present invention, two copies of the 5'-SAR are continuously present on the vector.

According to a preferable embodiment of the present invention, the two copies of the 5'-SAR are continuously present downstream of a protein-coding nucleotide sequence to be expressed.

As proved in the following examples, CSP-B 5'-SAR further improves the target protein expression level in animal cells as compared with CSP-B 3'-SAR and β-globin MAR of the related art. For example, when one copy of CSP-B 5'-SAR, CSP-B 3'-SAR, and β-globin MAR were respectively introduced into vectors expressing β galactosidase as a target protein in CHO animal cells, the β galactosidase activities for the respective cases were measured to be 10.0-fold, 2.2-fold, and 8.7-fold higher as compared with when the SAR factor was not introduced (FIG. 7). That is, CSP-B 5'-SAR exhibits a relatively higher target protein expression level than other factors.

Further, similar results were obtained when effects of the SAR factor were verified by using NESP as a target protein. When CSP-B 5'-SAR and CSP-B 3'-SAR were introduced into vectors and then CHO cells were transfected with the vectors, the NESP expression levels for the respective cases were measured to be 11.2-fold and 3.2-fold higher as compared with when the SAR factor was not introduced (Table 3 and FIG. 9). The introduction of CSP-B 5'-SAR into vectors increased the frequency of formation of positive clones expressing NESP in the transfected cells, and also increased the NESP expression levels of randomly selected clones (Tables 4 and 5 and FIGS. 10 and 11).

Meanwhile, the effects of CSP-B 5'-SAR were verified by using an anti-HER2 antibody as a target protein. When two copies of CSP-B 5'-SAR were introduced into the vector and then CHO cells were transfected with the vector, the anti-HER2 antibody expression level was measured to be relatively higher than as compared with when the SAR factor was not introduced (Table 6 and FIG. 13). The introduction of SAR into vectors increased the anti-HER2 antibody expression level of randomly selected clones (FIGS. 14 and 15).

According to a preferable embodiment of the present invention, multiple copies of CSP-B 5'-SAR may be present in the expression vector. The production efficiency of recombinant proteins are further increased when multiple copies of CSP-B 5'-SAR are present in the expression vector than when one copy of CSP-B 5'-SAR is present in the expression vector. More preferably, two copies of CSP-B 5'-SAR may be present in the expression vector. As proved in the following examples, the production efficiency of recombinant proteins was more excellent when two copies of CSP-B 5'-SAR are present in the expression vector than when three copies of CSP-B 5'-SAR are present in the expression vector.

As proved in the following examples, as a result of verifying effects of CSP-B 5'-SAR according to the copy number of CSP-B 5'-SAR by introducing one, two, and three copies of CSP-B 5'-SAR into vectors, the continuous location of two copies of the SAR factor was measured to exhibit the highest β-galactosidase activity (FIG. 8). That is, the copy number of SAR factor in the vector influences the target protein expression level, and two copies of the SAR factor may be the most desirable.

In the case where multiple copies of CSP-B 5'-SAR are present in the expression vector, the multiple copies of CSP-B 5'-SAR may be located in a continuous or non-continuous manner. Preferably, the multiple copies of SAR factors may be continuously present, and more preferably, may be continuously present downstream of a nucleotide sequence coding a protein to be expressed.

According to a preferable embodiment of the present invention, the promoter operable in the animal cells may be a cytomegalovirus (CMV) promoter, an adenovirus late promoter, a vaccinia virus 7.5K promoter, a Simian virus 40 (SV40) promoter, an SV40E1 promoter, a herpes simplex virus (HSV) tk promoter, a respiratory syncytial virus (RSV) promoter, an elongation factor 1-α (EF1-α) promoter, a metallothionein promoter, a β-actin promoter, a human interleukin-2 (IL-2) gene promoter, a human interferon (IFN) gene promoter, a human IL-4 gene promoter, a human lymphotoxin gene promoter, or human granulocyte-macrophage colony-stimulating factor (GM-CSF) gene promoter. The CMV promoter, SV40 promoter, SV40E1 promoter, EF1-α promoter, metallothionein promoter, or β-actin promoter is more preferable, and the CMV promoter is most preferable.

According to a preferable embodiment of the present invention, the vector of the present invention may be a nucleotide sequence coding a protein to be expressed. Preferable examples of the protein may include hormone, cytokine, antibody, peptide aptamer, Adnectin, affibody (U.S. Pat. No. 5,831,012), avimer ('Silverman, J. et al, *Nature Biotechnology* 23(12):1556 (2005)), or a Kunitz domain (Kunitz domain, Arnoux B et al., *Acta Crystallogr. D Biol. Crystallogr.* 58 (Pt 7):12524 (2002)), and (Nixon, A E, *Current opinion in drug discovery & development* 9(2):2618 (2006). More preferably, the protein to be expressed by using the vector of the present invention may be erythropoietin (EPO), EPO analogs, or anti-human epidermal growth factor receptor 2 (anti-HER2) antibodies. EPO, novel erythropoiesis stimulating proteins (NESPs; A30N, H32T, P87V, W88N, and P90T) as EPO analogs, or anti-HER2 antibodies may be most preferable.

The EPO analogs include mutants having modification of one or more amino acids from the human EPO amino acid sequence. The EPO analogs may be prepared by the mutagenesis through addition, deletion, or substitution of amino acid residues, whereby the glycosylation sites may be increased or may be changed. The EPO analogs have more carbohydrate chains than the human EPO, and include at least one additional glycosylation site. In addition, the EPO analogs exhibit a higher sialic acid level than the naturally occurring human EPO due to the additional glycosylation site. However, the protein secondary or tertiary structure, which is important in biological activity, is not changed by the additional glycosylation site. The EPO analogs may have one, two, or three additional sites for N-cosylation or O-glycosylation. For example, the leucine residue at position 69 is substituted with asparagine, which serves as a fourth site for N-glycosylation.

Examples of the EPO analogs to be expressed in the vectors of the present invention may be ones in which an additional site for glycosylation is introduced to at least one of positions 30, 51, 57, 69, 88, 89, 136, and 138 in the EPO sequence (e.g., sequence of GenBank Accession #M11319). More preferably, the EPO analogs may be NESPs including A30N, H32T, P87V, W88N, and P90T mutations.

According to a preferable embodiment of the present invention, the polyadenylation sequence includes a bovine growth hormone terminator, herpes simplex virus (HSV)-derived thymidine kinase (TK), or SV40-derived polyadenylation sequence.

A preferable construct of the vector of the present invention may be, in a 5' to 3' direction, a promoter operable in animal cells—an expression protein gene—a polyadenylation sequence—CSP-B 5'-SAR, and a more preferable construct is a promoter operable in animal cells—an expression protein gene—a polyadenylation sequence—CSP-B 5'-SAR—CSP-B 5'-SAR.

The vector of the present invention may further include a selection marker. Examples of the selection marker include resistance genes against antibiotics acting on eukaryotic cells, and preferably include resistance genes against neomycin, geneticin (G418), and kanamycin.

According to a preferable embodiment of the present invention, the vector of the present invention is used in expressing a target protein in animal cells. The animal cells include mammalian cells, rodent cells, avian cells, and insect cells. The animal cells more preferably include Chinese hamster ovary (CHO) cells, VERO cells, HeLa cells, W138 cells, baby hamster kidney (BHK) cells, COS cells, and Madin-Darby Canine Kidney (MDCK) cells. The CHO cells, VERO cells, HeLa cells, or MDCK cells are still more preferable, and the CHO cells are most preferable.

According to a preferable embodiment of the present invention, the vector of the present invention includes a dihydrofolate reductase (DHFR) coding sequence. The sequence is useful in vector amplification.

According to another aspect of the present invention, the present invention provides animal cells transfected with the foregoing expression vectors of the present invention.

According to still another aspect of the present invention, the present invention provides a method for producing recombinant proteins, the method including incubating the foregoing transfected animal cells of the present invention.

According to a preferable embodiment of the present invention, the method for producing recombinant proteins includes: (i) incubating the transfected animal cells of the present invention; and (ii) collecting recombinant proteins produced in the incubating.

In the related art, CSP-B 5'-SAR used herein was not used in an attempt to be introduced into expression vectors for animal cells to improve productivity in recombinant proteins for medical substances. As can be seen from the following examples, the introduction of CSP-B 5'-SAR into vectors can improve the target protein expression level in animal cells. By developing the method in which CSP-B 5'-SAR, a new factor that was not previously used, is introduced into vectors to produce recombinant proteins, the target protein expression efficiency can be further improved and the industrial productivity of protein medical substances can be increased.

According to reports in the related art, there were no attempts to introduce CSP-B 5'-SAR into expression vectors for animal cells to improve productivity of recombinant proteins for medical substances. Moreover, studies were not conducted that, in the case where one, two, and three copies of SAR factors are introduced in the vectors and then animal cells are transfected with the vectors, how many copies of SAR factors are included in the vector in order to achieve the highest productivity of recombinant proteins. Moreover, detailed preceding study results about the increase effect in the target gene expression level depending on the position of the SAR factor have not been disclosed.

When the expression vectors of the present invention are introduced into cells to produce transfected animal cells, the vectors may be introduced into cells by various methods. The vectors may be injected into animal cells by, for example, micro-injection (Capecchi, M. R., *Cell,* 22:479 (1980)), calcium phosphate precipitation (Graham, F. L. et al., *Virology,* 52:456 (1973)), electroporation (Neumann, E. et al., *EMBO J.,* 1:841 (1982)), liposome-mediated transfection (Wong, T. K. et al., *Gene,* 10:87 (1980)), DEAE-dextran treatment (Gopal, *Mol. Cell. Biol.* 5:1188-1190 (1985)), gene bombardment (Yang et al., *Proc. Natl. Acad. Sci.,* 87:9568-9572 (1990)), or the like.

The transfected animal cells may be incubated by various methods known in the art using protocols. As a medium usable herein, any medium that can be generally used to incubate animal cells may be employed. For example, Eagle's minimum essential medium (Eagles's MEM, Eagle, H. *Science* 130:432 (1959)), α-MEM (Stanner, C. P. et al., *Nat. New Biol.* 230:52 (1971)), Iscove's MEM (Iscove, N. et al., J. Exp. Med. 147:923 (1978)), 199 medium (Morgan et al., *Proc. Soc. Exp. Bio. Med.,* 73:1 (1950)), CMRL 1066, RPMI 1640 (Moore et al., *J. Amer. Med. Assoc.* 199:519 (1967)), F12 (Ham, *Proc. Natl. Acad. Sci. USA* 53:288 (1965)), F10 (Ham, R. G. Exp. *Cell Res.* 29:515 (1963)), Dulbecco's modification of Eagle's medium (DMEM, Dulbecco, R. et al., *Virology* 8:396 (1959)), a mixture of DMEM and F12 (Barnes, D. et al., *Anal. Biochem.* 102:255 (1980)), Way-mouth's MB752/1 (Waymouth, C. *J. Natl. Cancer Inst.* 22:1003 (1959)), McCoy's 5A (McCoy, T. A., et al., *Proc. Soc. Exp. Biol. Med.* 100:115 (1959)), MCDB series (Ham, R. G. et al., *In Vitro* 14:11 (1978)), and the like may be used. Detailed descriptions of incubations and media of animal cells are disclosed in R. Ian Freshney, *Culture of Animal Cells, A Manual of Basic Technique*, Alan R Liss, Inc., New York, which is incorporated by reference into the present specification.

Advantageous Effects

Features and advantages of the present invention are summarized as follows:

(a) The vectors of the present invention include CSP-B 5'-SAR, and can have effects of overcoming gene expression suppression depending on positions of foreign genes introduced into animal cells and significantly improve the target protein expression level.

(b) The vectors of the present invention can effectively express recombinant proteins for medical substances (e.g., EPO) or antibodies (e.g., anti-HER2 antibody) in animal cells.

(c) The vectors of the present invention and the method for producing recombinant proteins using the vectors can be very usefully employed in industrial mass production of medical substances.

MODE FOR CARRYING OUT THE INVENTION

Figure 1:
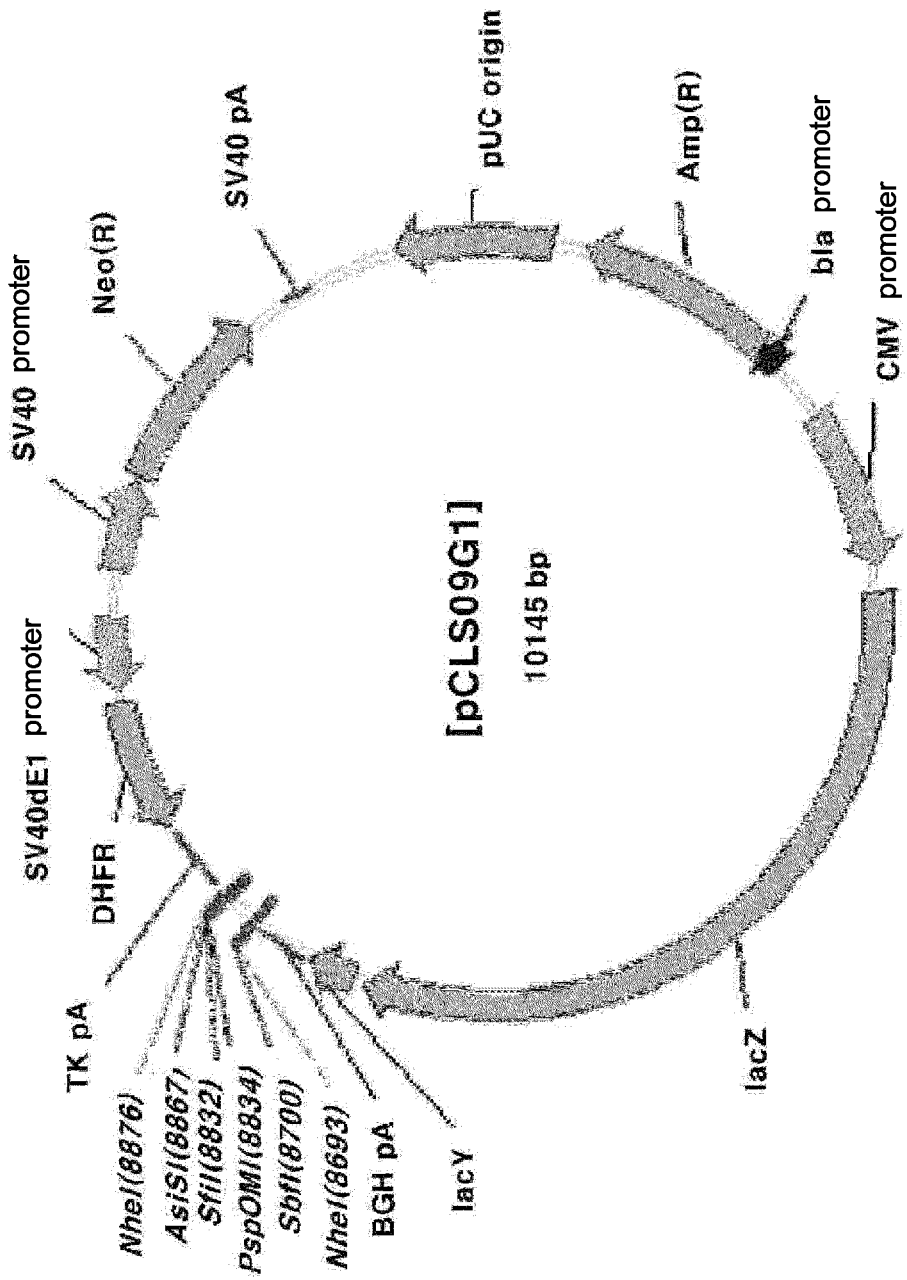
FIG. 1 schematically shows a structure of a β-galactosidase expression vector. Here, lac Z represents a β-galactosidase gene; BGH pA represents a polyadenylation sequence of a bovine growth hormone gene; and TK pA represents a polyadenylation sequence of a thymidine kinase gene.
Figure 2A:
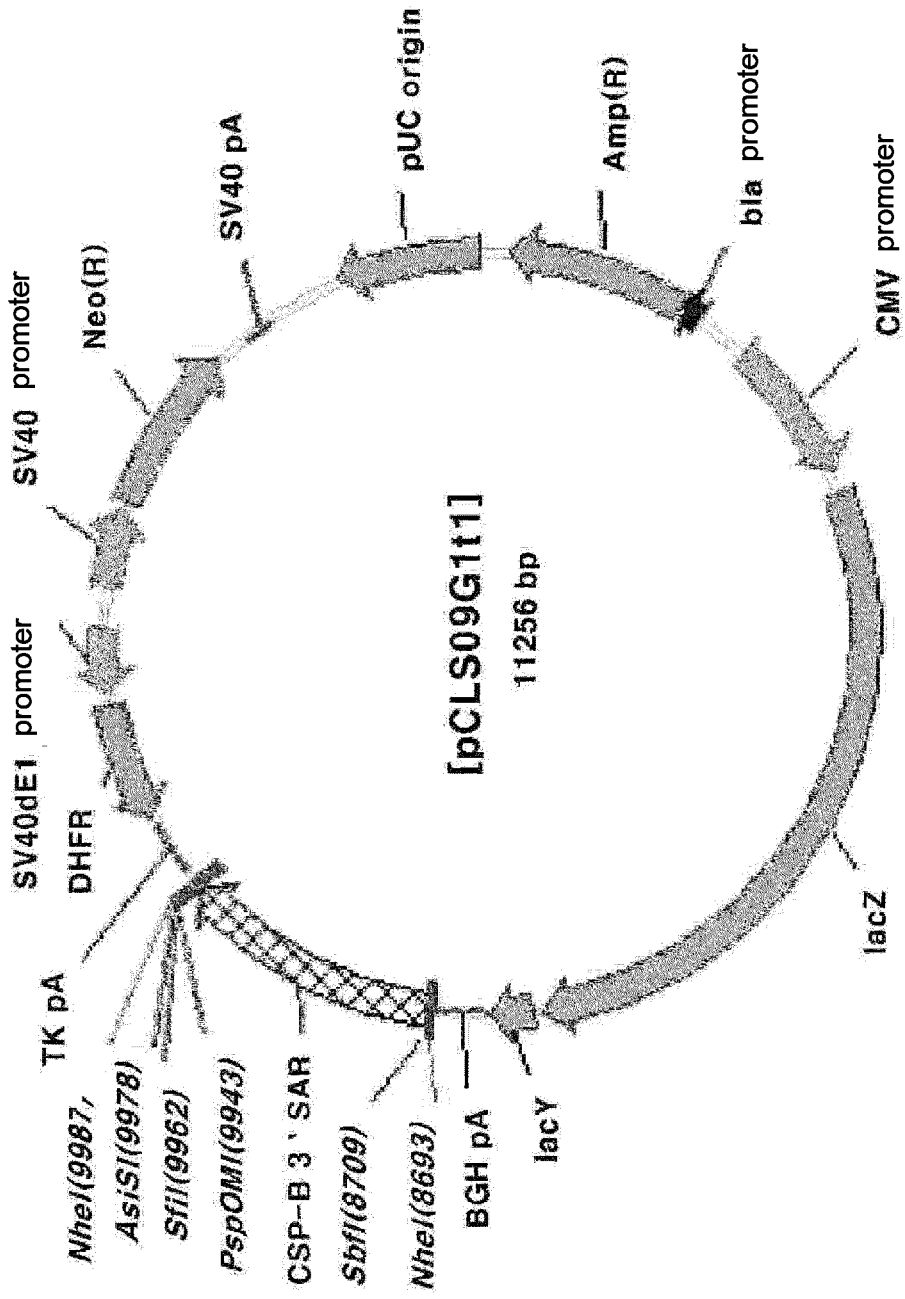
FIGS. 2a-2c schematically show three structures (a, b, and c) of β-galactosidase expression vectors including one copy of SAR/MAR factor.
Figure 2B:
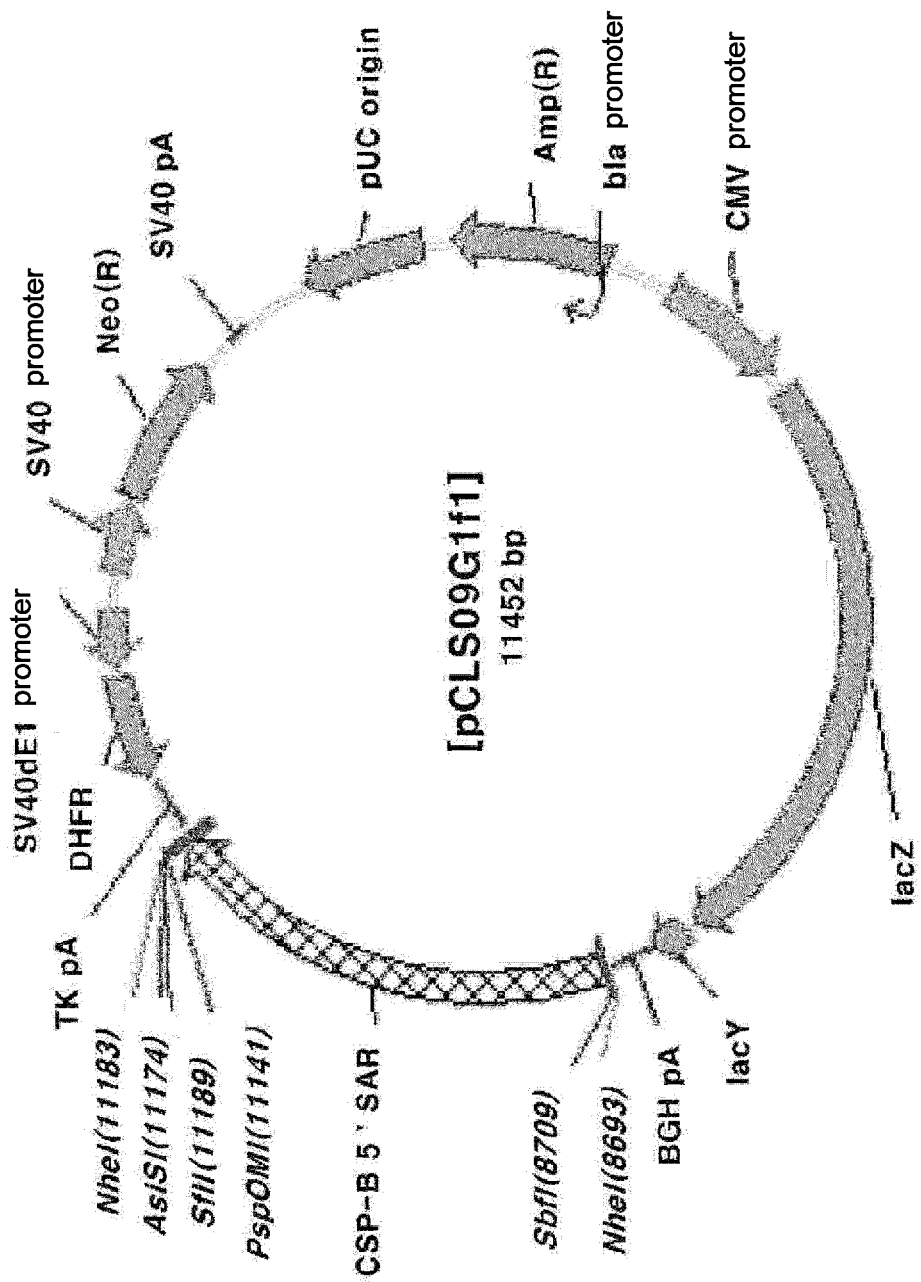
Figure 2C:
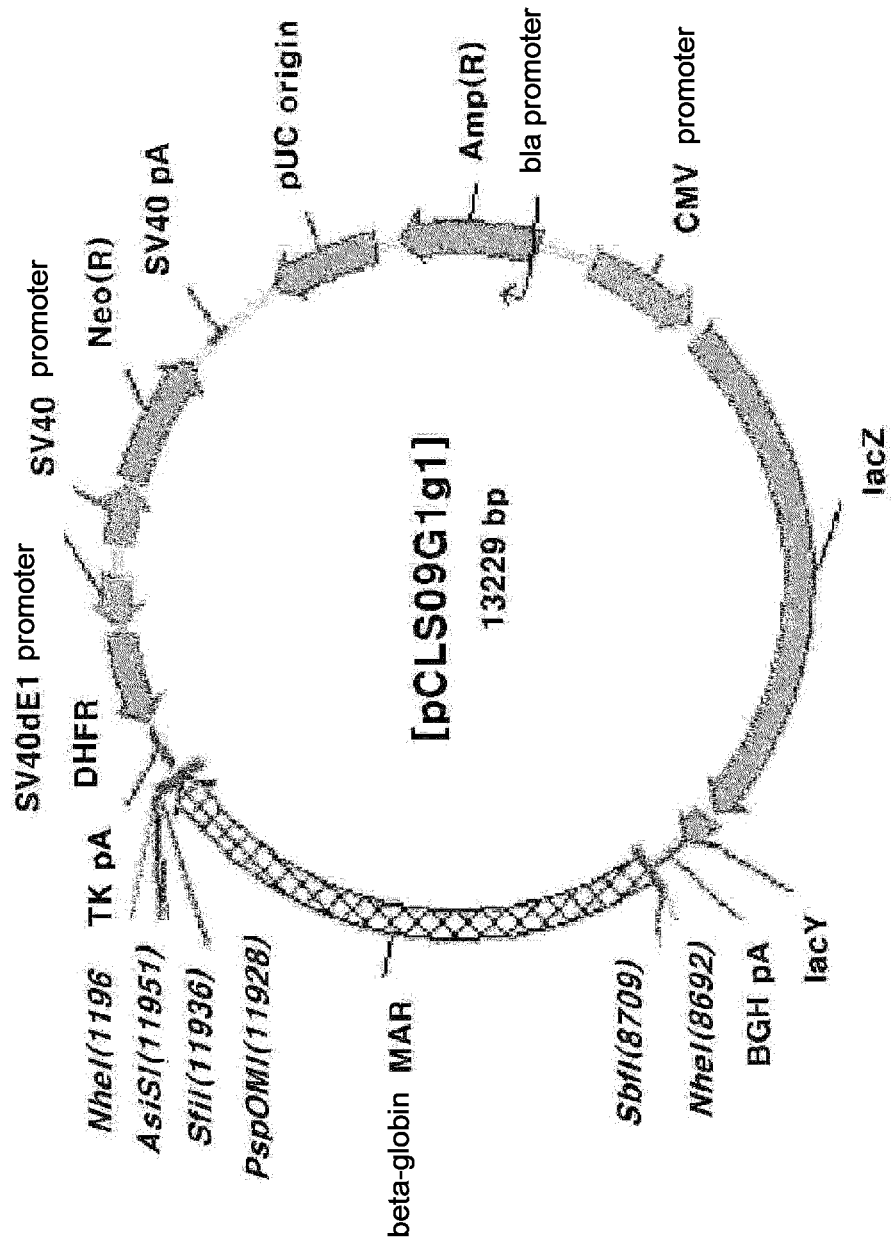
Figure 3A:
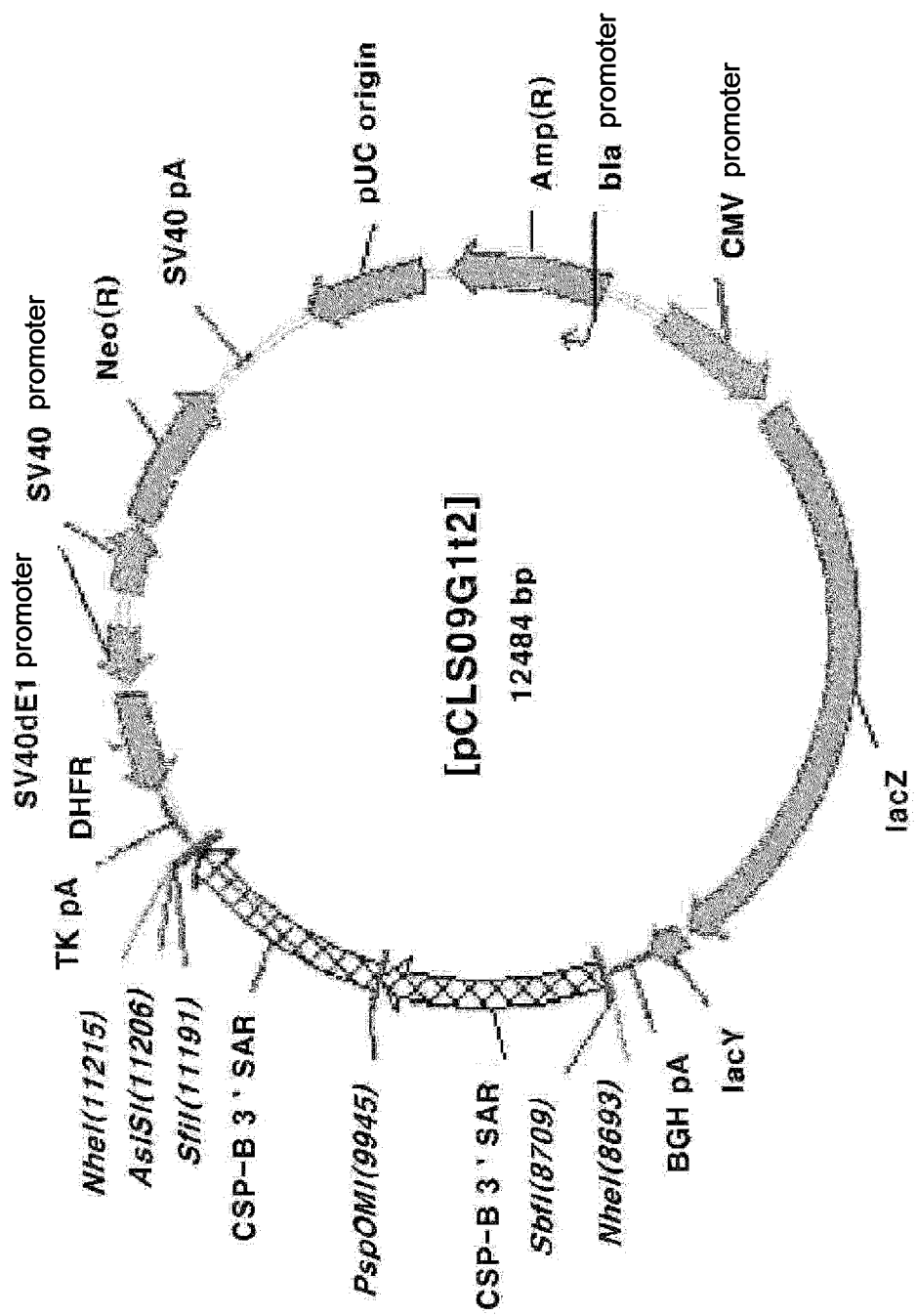
FIGS. 3a-3d schematically show four structures (a, b, c, and d) of β-galactosidase expression vectors including two copies of SAR factors.
Figure 3B:
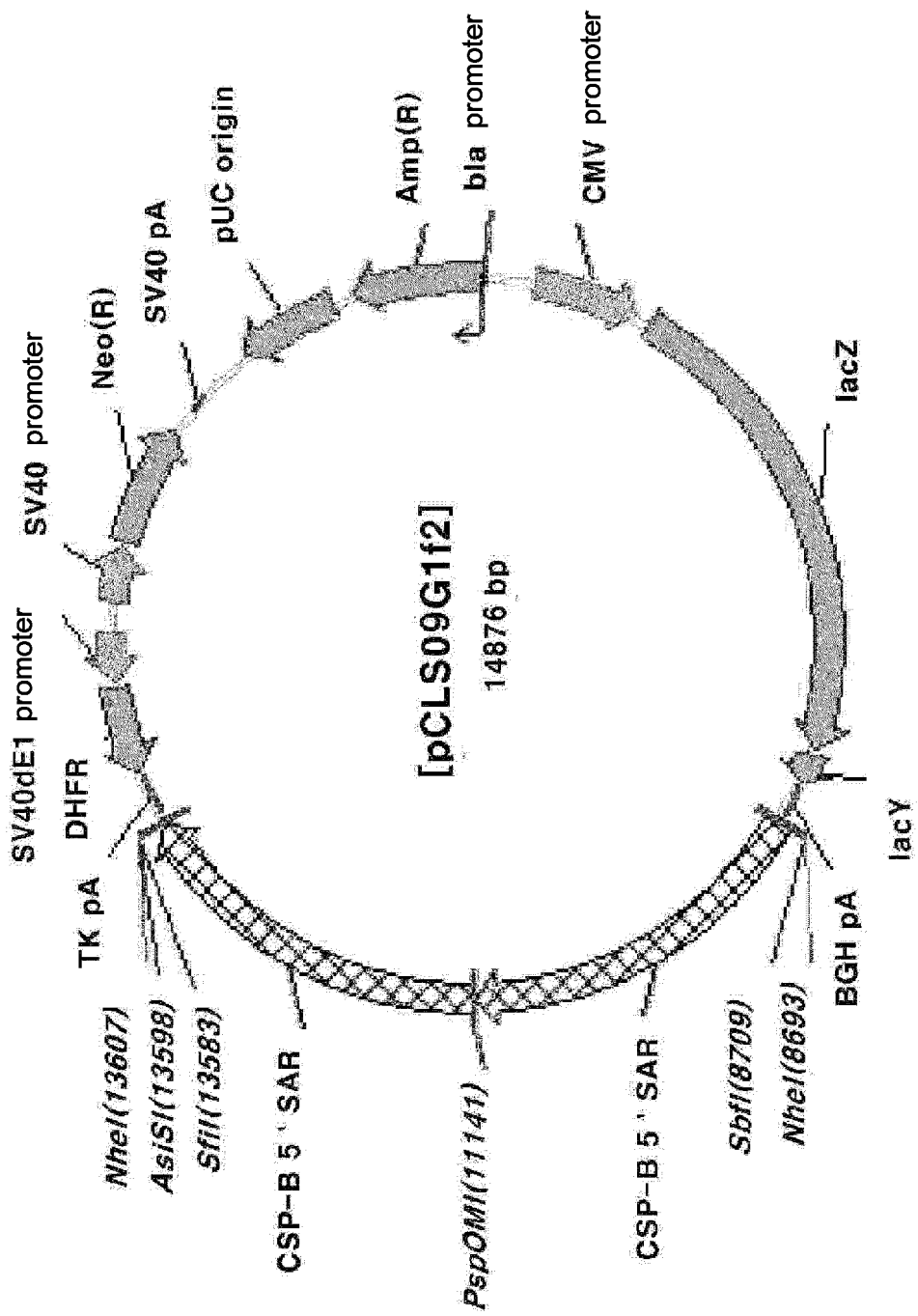
Figure 3C:
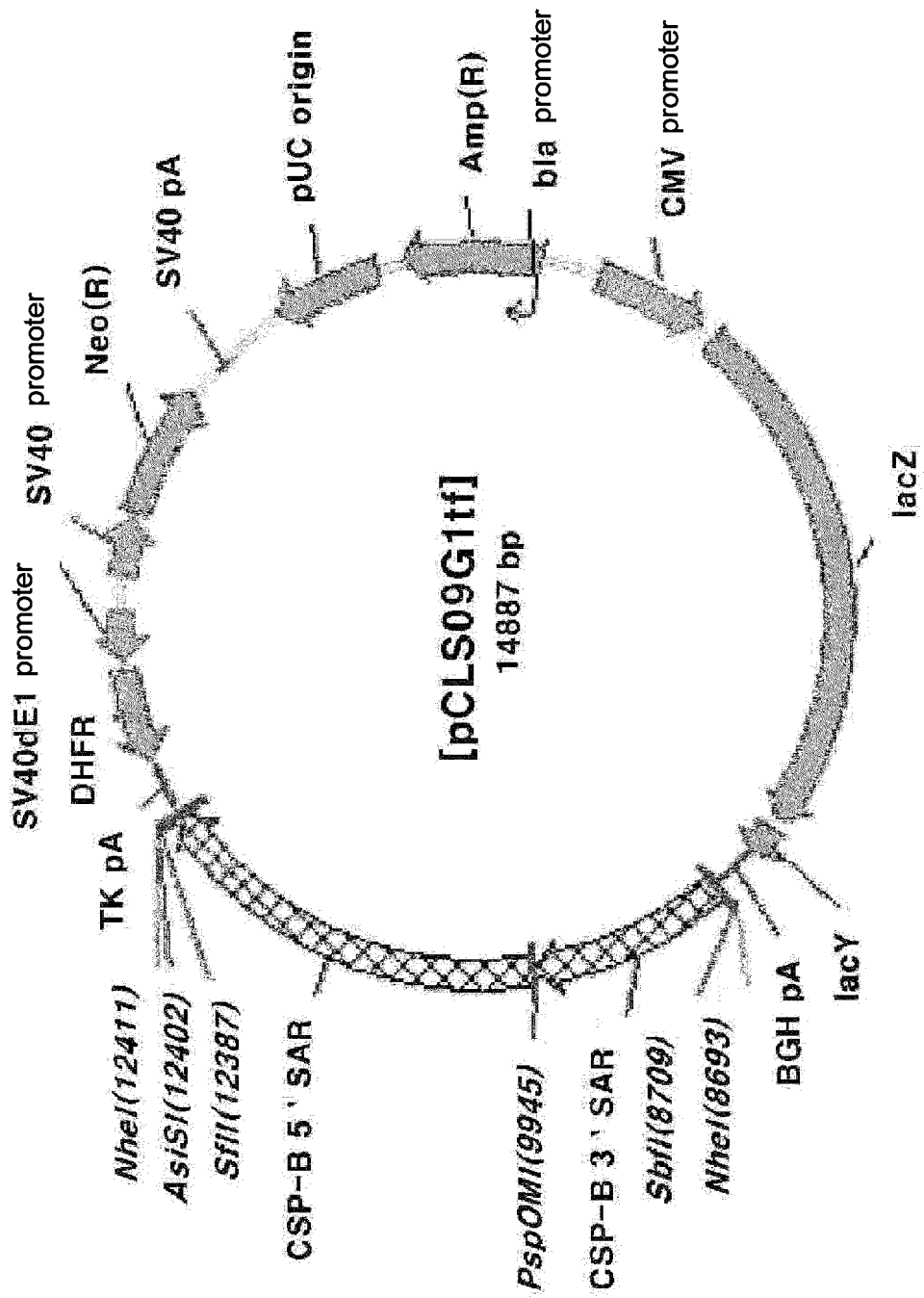
Figure 3D:
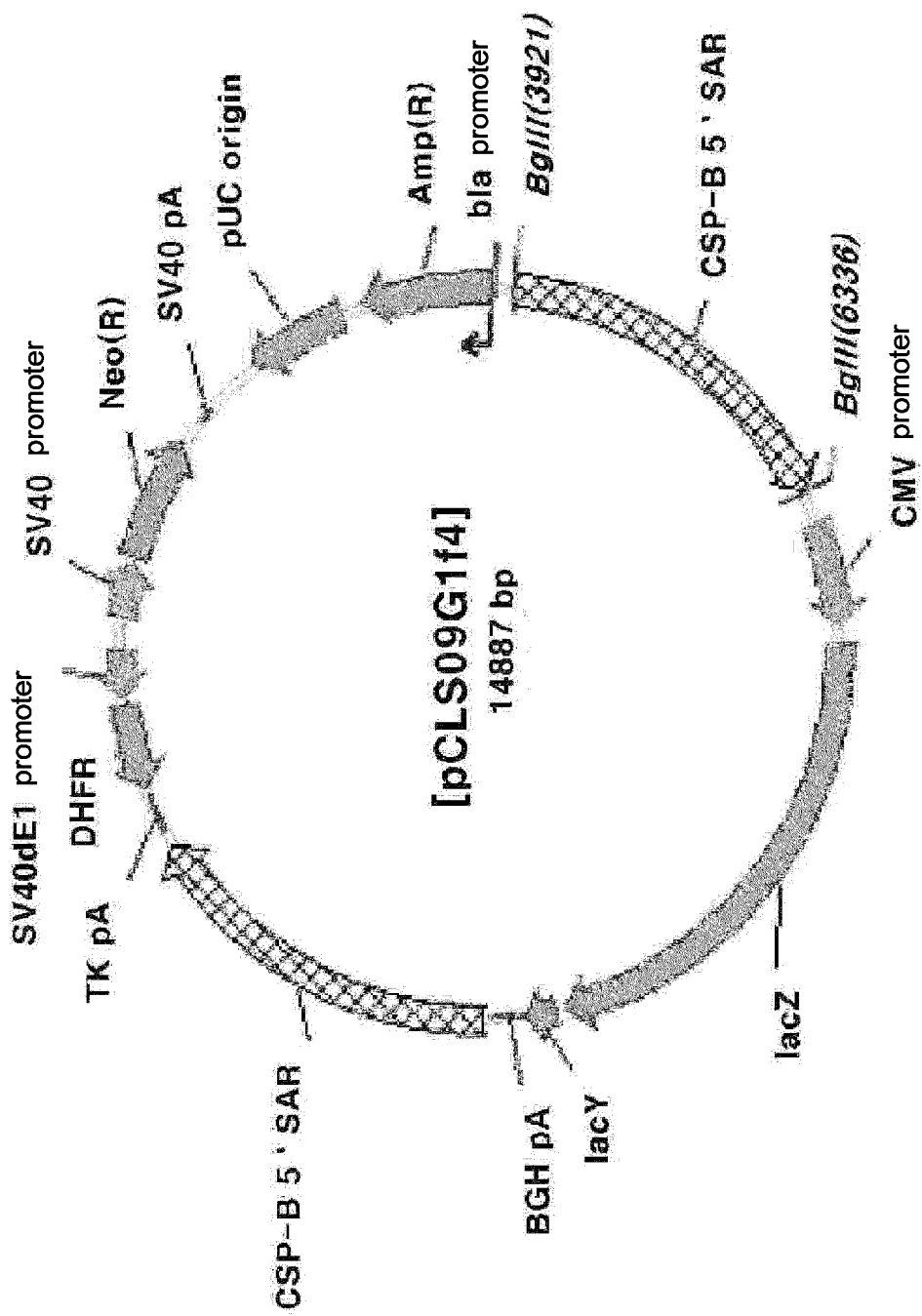
Figure 4:
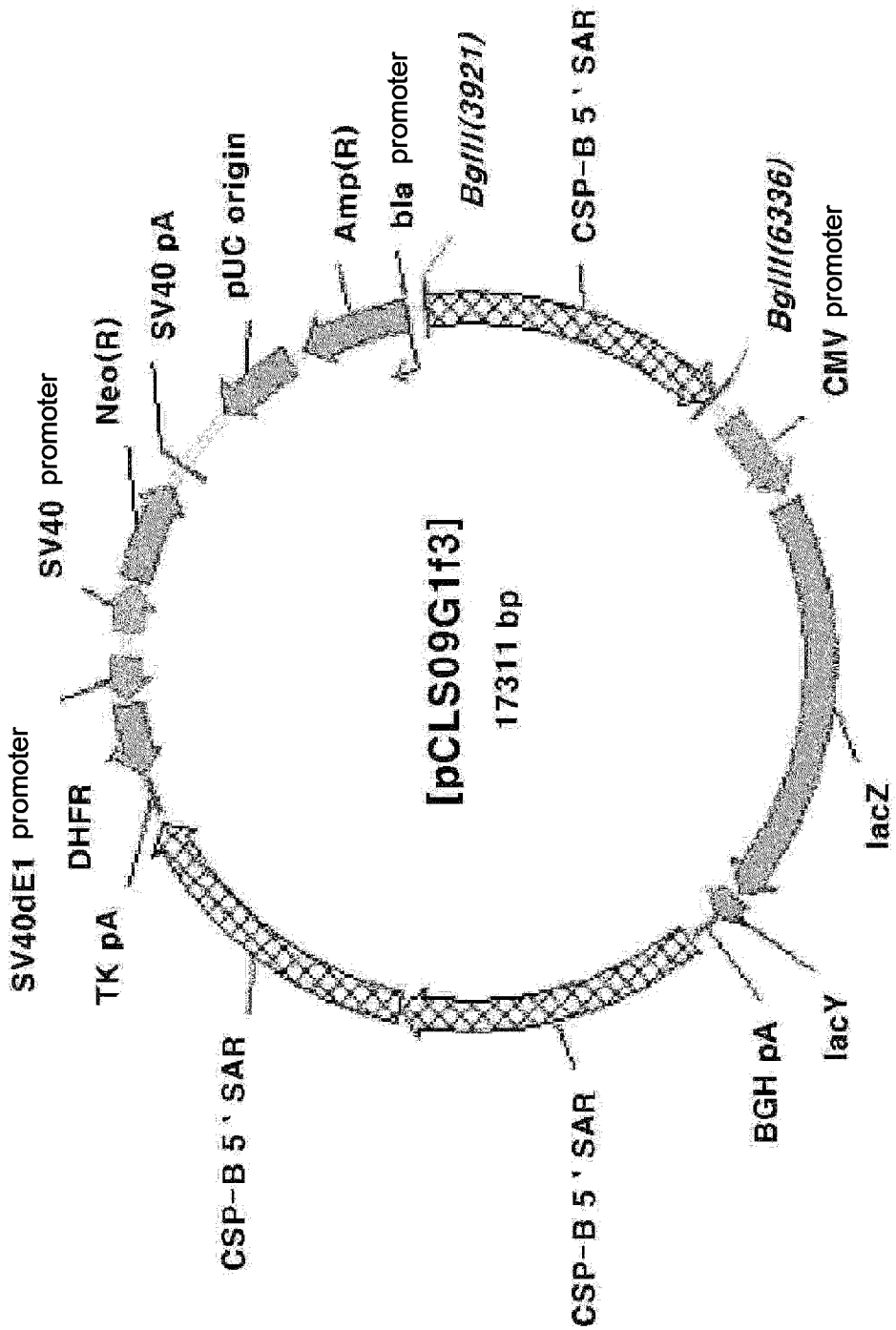
FIG. 4 schematically shows a structure of a β-galactosidase expression vector including three copies of CSP-B 5'-SAR.
Figure 5A:
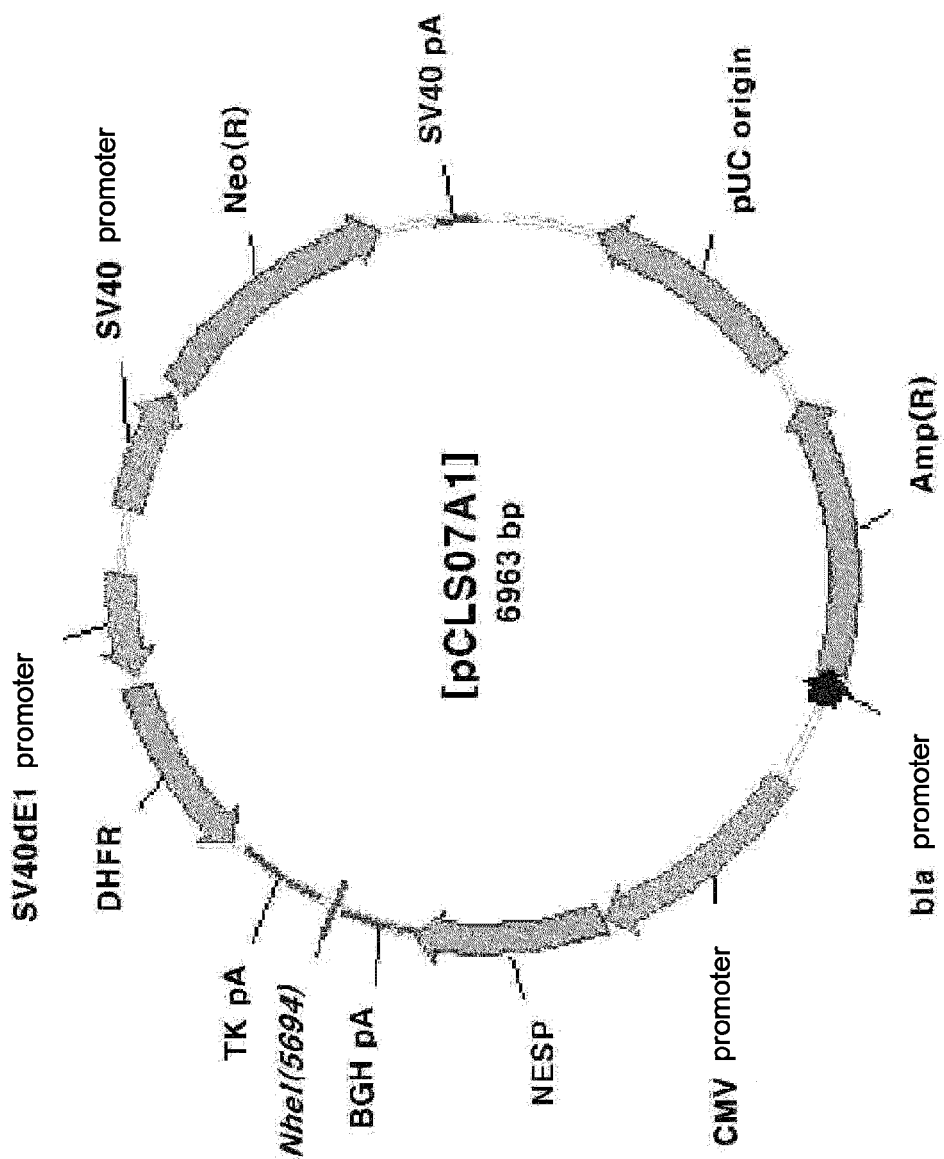
FIGS. 5a-5b schematically show two (a and b) structures of NESP expression vectors.
Figure 5B:
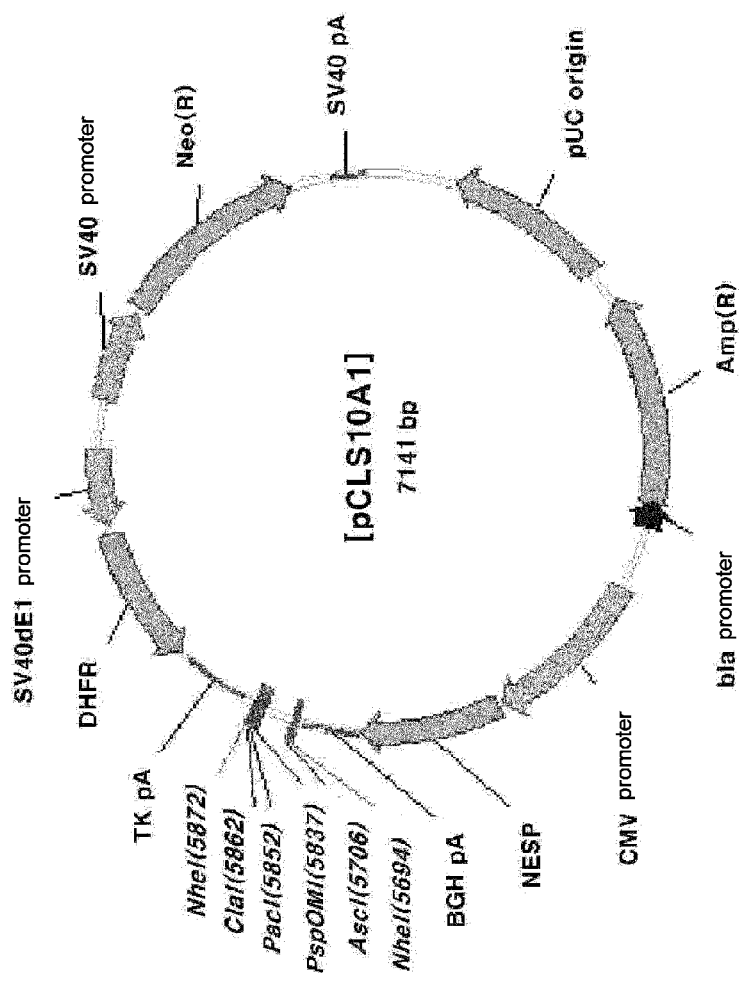
Figure 6A:
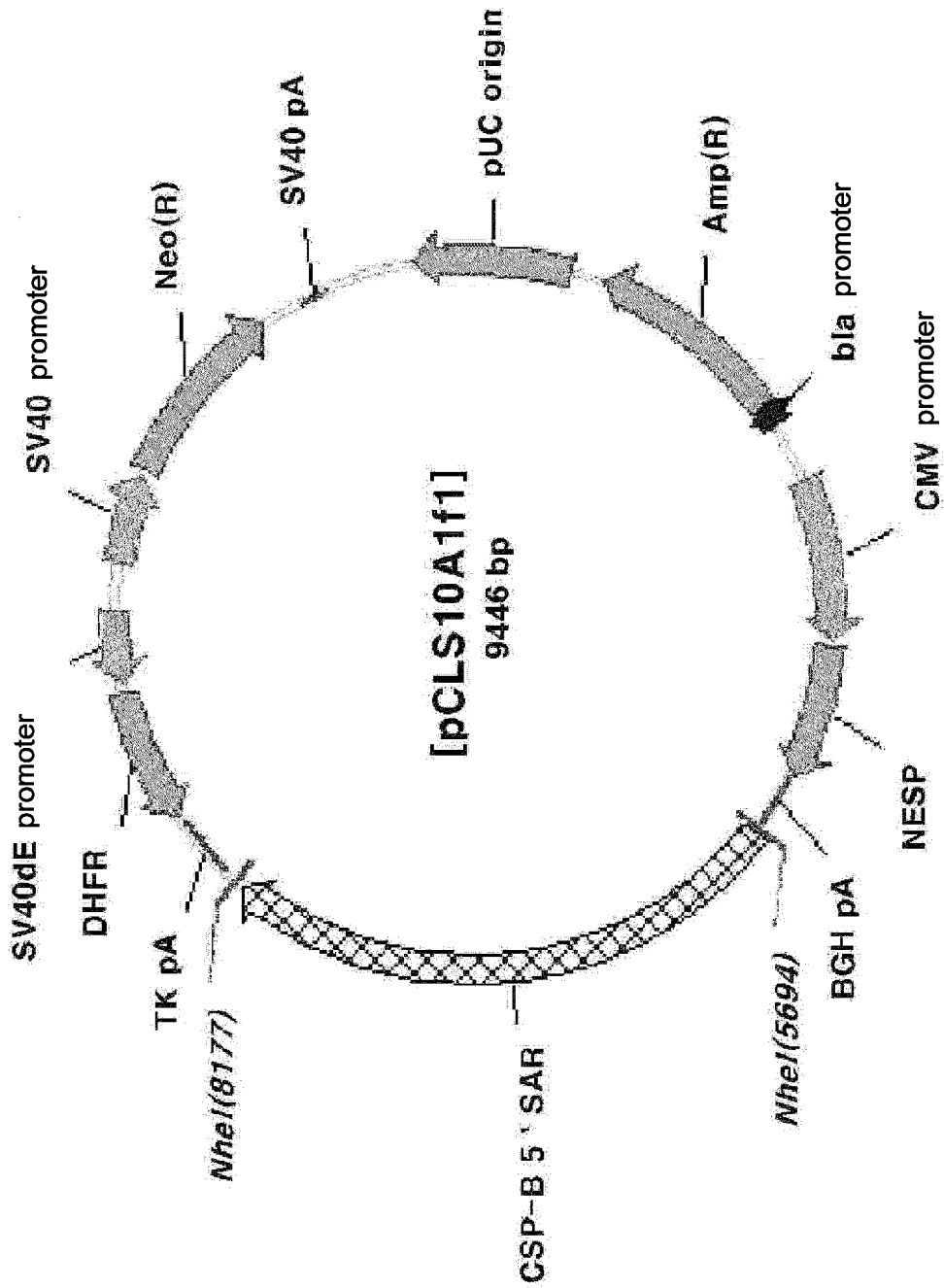
FIGS. 6a-6b schematically show two (a and b) structures of NESP expression vectors including SAR/MAR factors.
Figure 6B:
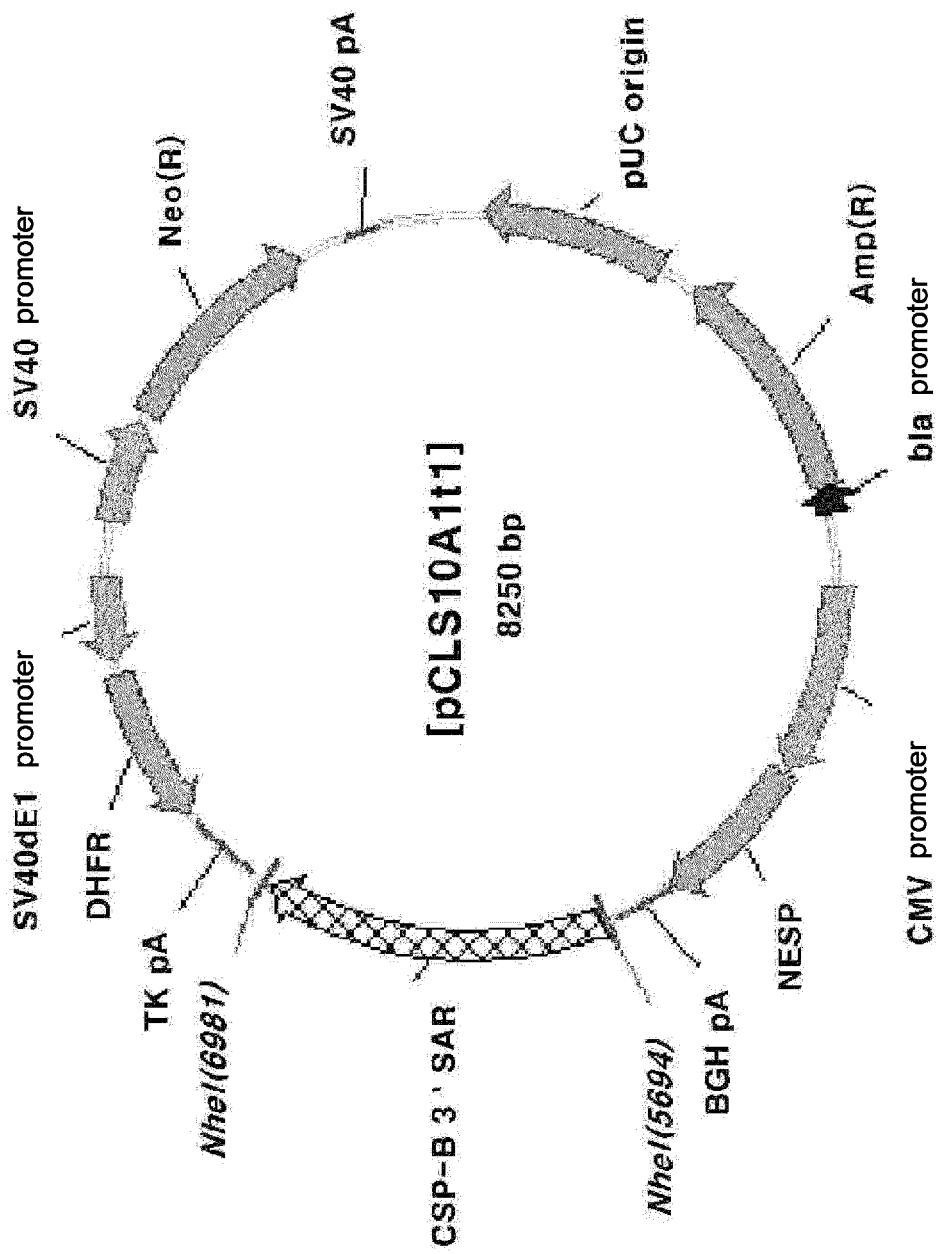

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

Preparation of SAR/MAR Factor

Preparation of Human CSP-B 5'-SAR and CSP-B 3'-SAR

For polymerase chain reaction (PCR) amplification of human CSP-B 5'-SAR DNA registered as GenBank Accession #M62717 and #AL136018, genomic DNA of human natural killer cells (NK cells, ATCC CRL-2407) was prepared. The genomic DNA was prepared from the NK cells using a DNA isolation kit (DNEASY® Blood & Tissue Kit, Qiagen, Cat. No. 69504), and was used as a template for 5'-SAR DNA PCR.

PCR was performed using the Cs5S300F primer (attct tcagc acctc cttaa ttttt ctccc; SEQ ID NO: 5) and the Cs5S300R primer (ccagg cagcc aaaga tcagt agttg tgttg; SEQ ID NO: 6) while using the genomic DNA of the NK cells as a template. The PCR was performed under the conditions of 35 cycles of 10 seconds at 98° C., 30 seconds at 60° C., and 2 minutes and 30 seconds at 72° C.

Then, the PCR product was cloned into the PGEM-T® vector (Promega, Cat. No. A3600) to prepare the PGEMT®-CS5S.3.0K vector.

For preparation of human CSP-B 3'-SAR DNA registered as Gen Bank Accession #M62716 and #AL136018, PCR was performed using the 2kCspSF primer (tggtt ccttc attgg aaaag gaaaa cac; SEQ ID NO: 7) and the 2kCspSR primer (tccgc tgagg ctgtg cccac agcca cc; SEQ ID NO: 8) while using the genomic DNA of the NK cells as a template. Then, PCR was performed using the CspSF primer (ggatc ccatt ctcct tgatg tacta at; SEQ ID NO: 9) and the CspSR primer (gaatt caaac aactc aatag caaga aac; SEQ ID NO: 10) while using the primary PCR product as a template. The PCRs were performed under the conditions of 30 cycles of 10 seconds at 98° C., 30 seconds at 60° C., and 5 minutes at 72° C. The secondary PCR product was cloned into the PGEM-T® vector to prepare the PGEMT®-CS3S.1.2K vector.

Preparation of Human β-Globin MAR

For PCR amplification of human β-globin MAR DNA registered as GenBank Accession #L22754 and #NW_001838021, genomic DNA of human G-2 cells was prepared. The genomic DNA was prepared from the G-2 cells using a DNA isolation kit, and was used as a template for 5' MAR DNA PCR. PCR was performed using the Bg5MF-100E-NheI primer (aattg ctagc ttgta ttctg tttcg tgagg caagg ttt; SEQ ID NO: 11) and the Bg5MR-100R-XhoI primer (aattc tcgag ttcct ctcta tgttg gctca aatgt cct; SEQ ID NO: 12) while using the genomic DNA of the G-2 cells as a template. The PCR was performed under the conditions of 30 cycles of 10 seconds at 98° C., 30 seconds at 60° C., and 3 minutes and 30 seconds at 72° C. Then, the PCR product was cloned into the PCDNA™3.3TOPO® vector (Invitrogen, Cat. No. K8300-01) to prepare the PCDNA™3.3-BG5M vector.

Example 2

Preparation of β-Galactosidase Expression Vector

Preparation of pC06

For preparation of the pC06 vector sequentially including the cytomegalovirus (CMV) promoter, multiple cloning sites (MCS), and the bovine growth hormone (BGH) polyadenylation sequence (pA), the following experiment was conducted. First, PCR was performed using the V6_F primer (aagct tggat ccgaa ttcat cgatg gccgg ccggt accct cgagc tgtgc cttct agttg ccagc; SEQ ID NO: 13) and the V6_R primer (gctag ctaga gcccc agctg gttct ttccg; SEQ ID NO: 14) while using the pcDNA3.1(−) vector (Invitrogen, Cat. No. V795-20) as a template. The PCR was performed under the conditions of 30 cycles of 10 seconds at 98° C., 30 seconds at 60° C., and 1 minute at 72° C. Then, the PCR product was cloned into the PCDNA™3.3TOPO® vector (Invitrogen) to prepare the pC06 vector.

Preparation of pC04'

For preparation of the pC04' sequentially including the Simian virus 40 (SV40) promoter, the Kozak sequence (gc-catc), the dihydrofolate reductase (dhfr) gene, the herpes simplex virus thymidine kinase (HSV-TK) pA, the following experiment was conducted. First, PCR was performed using the PsvApaDraF primer (aaaat tgggc cccac tacgt gctgt ggaat gtgtg tcagt taggg t; SEQ ID NO: 15) and the PsvKzDHR primer (tggtc gaacc atgat ggcgc gaaac gatcc tcatc ctgtc tct; SEQ ID NO: 16) while using the PCDNA™3.3 vector as a template. Then, PCR was performed using the DHKzPsvF primer (ggatc gtttc gcgcc atcat ggttc gacca ttgaa ctgca tcg; SEQ ID NO: 17) and the TKNheNdeR primer (tgtgt gcata tggct agcga taaca atttc acaca ggaaa cag; SEQ ID NO: 18) while using the POPTIVEC™-TOPO® vector as a template. The PCRs were performed under the conditions of 30 cycles of 10 seconds at 98° C., 30 seconds at 60° C., and 1 minute at 72° C. Then, these two PCR products were ligated through overlapping PCR, and cloned between the ApaI and NdeI restriction sites of the PGEM-T® vector, to prepare the pC04' vector.

Preparation of pC04

For preparation of the pC04 vector in which one 72-bp enhancer (ggtgt ggaaa gtccc caggc tcccc agcag gcaga agtat gcaaa gcatg catct caatt agtca gcaac ca; SEQ ID NO: 19) was removed from the SV40 promoter included in the pC04' vector (SV40dEI promoter), the following experiment was conducted. First, the pC04' vector was digested with the restriction enzyme SphI, and then the thus obtained large DNA fragment was self-ligated, to prepare the pC04 vector.

Preparation of pCLS07 Vector

For preparation of the pCLS07 vector including the SV40dE1 promoter, the Kozak sequence, the dhfr gene, and TK pA, which were inserted between the BGH pA and the SV40 promoter of the pC06 vector, the following experiment was conducted. First, PCR was performed using the PsvApaDraF primer and the TKNheNdeR primer while using the pC04 vector as a template. The PCR was performed under the conditions of 30 cycles of 10 seconds at 98° C., 30 seconds at 60° C., and 1 minute and 20 seconds at 72° C. Then, this PCR product and the pC06 vector were digested with the restriction enzymes DraIII and NheI, respectively, and the thus obtained two large DNA fragments are ligated to prepare the pCLS07 vector.

Preparation of pCLS08 Vector

For preparation of the pCLS08 vector by inserting MCS into the NheI restriction site of the pCLS07 vector, the following experiment was conducted. First, PCR was conducted using the NhAsE1F primer (aattg ctagc atata gcgat cgcgc aggac agctt ccgac agcag ggcca gg; SEQ ID NO: 20) and the BbPsSbNhE1R primer (aattg ctagc atata cctgc aggta tatgg gccca tatag ctgag gttga atgag aatat cactg tccca gacac; SEQ ID NO: 21) while using the erythropoietin gene cloned into the PGEM-T® vector as a template, to prepare MCS. The PCR was performed under the conditions of 30 cycles of 10 seconds at 98° C., 30 seconds at 60° C., and 15 seconds at 72° C. Then, this PCR product was cloned into the NheI restriction site of the pCLS07 vector to prepare the pCLS08 vector.

Preparation of pCLS08G1 Vector

For preparation of the pCLS08G1 vector by inserting the lac Z and lac Y genes between the HindIII and XhoI restriction sites of the pCLS08 vector, the following experiment was conducted. First, PCR was performed using the galHinF primer (aatta agctt ctcgc gcaac ctatt ttccc ctcga ac; SEQ ID NO: 22) and the galXhoR primer (aattc tcgag ccgag tttgt cagaa agcag accaa ac; SEQ ID NO: 23) while using the pSV-β-galactosidase vector (Promega, Cat. No. TB094) as a template, to amplify the lac Z and lac Y genes. The PCR was performed under the conditions of 30 cycles of 10 seconds at 98° C., 30 seconds at 60° C., and 3 minutes and 30 seconds at 72° C. Then, this PCR product was cloned between HindIII and XhoI restriction sites of the pCLS08 vector to prepare the pCLS08G1 vector.

Preparation of pCLS09G1 Vector

For preparation of the pCLS09G1 vector by exchanging the MCS between two NheI restriction sites of the pCLS08G1 vector with another MCS, the following experiment was conducted. First, PCR was performed using the NhSbE1F primer (aattg ctagc atata cctgc aggtt gaatg agaat atcac tgtcc cagac a; SEQ ID NO: 24) and the NhAsSfPsE1R primer (aattg ctagc atata gcgat cgcta tatgg ccatg atggc catat agggc ccagg acagc ttccg acagc agggc caggc; SEQ ID NO: 25) while using the erythropoietin gene cloned into the PGEM-T® vector as a template, to prepare new MCS. The PCR was performed under the conditions of 30 cycles of 10 seconds at 98° C., 30 seconds at 60° C., and 15 seconds at 72° C. Then, the existing MCS between the two NheI restriction sites of the pCLS80G1 vector was removed, and the new MCS generated through the PCR was cloned thereinto, to prepare pCLS09GI vector. The map of the pCLS09G1 vector was shown in FIG. 1.

Example 3

Preparation of β-Galactosidase Expression Vector Including SAR/MAR Factor

Preparation of pCLS09G1t1 Vector

For preparation of the pCLS09G1t1 vector by inserting the CSP-B 3'-SAR between the SbfI and PspOMI restriction sites of the pCLS09G1 vector, the following experiment was conducted. First, PCR was conducted using the cs3sSbf1F primer (aattc ctgca gggga tccca ttctc cttga tgtac taat; SEQ ID NO: 26) and the cs3sPsp1R primer (aattg ggccc gaatt caaac aactc aatag caaga aac; SEQ ID NO: 27) while using the pGEMT-CS3S.1.2k vector as a template, to amplify CSP-B 3'-SAR. The PCR was performed under the conditions of 30 cycles of 10 seconds at 98° C., 30 seconds at 60° C., and 2 minutes and 30 seconds at 72° C. Then, this PCR product was cloned between the SbfI and PspOMI restriction sites of the pCLS09G1 vector to prepare the pCLS09G1t1 vector.

Preparation of pCLS09G1f1 Vector

For preparation of the pCLS09G1f1 vector by inserting the CSP-B 5'-SAR between the SbfI and PspOMI restriction sites of the pCLS09G1 vector, the following experiment was conducted. First, PCR was conducted using the cs5sSbf1F primer (aattc ctgca gggaa ttcct aaaca gagca attag gtaag; SEQ ID NO: 28) and the cs5sPsp1R primer (aattg ggccc gaatt ccagt gtaaa cgtct tcctt gt; SEQ ID NO: 29) while using the pGEMT-CS5S.3.0k vector as a template, to amplify CSP-B 5'-SAR. The PCR was performed under the conditions of 30 cycles of 10 seconds at 98° C., 30 seconds at 60° C., and 2 minutes and 30 seconds at 72° C. Then, this PCR product was cloned between the SbfI and PspOMI restriction sites of the pCLS09G1 vector to prepare the pCLS09G1f1 vector.

Preparation of pCLS09G1g1 Vector

For preparation of the pCLS09G1g1 vector by inserting the β-globin MAR between the SbfI and PspOMI restriction sites of the pCLS09G1 vector, the following experiment was conducted. First, PCR was performed using the glmSbf1F primer (aattc ctgca ggttg tattc tgttt cgtga ggcaa ggttt; SEQ ID NO: 30) and the glmPsp1R primer (aattg ggccc ttcct ctcta tgttg gctca aatgt cct; SEQ ID NO: 31) while using the pcDNA3.3-Bg5M vector as a template, to amplify the β-globin MAR. The PCR was performed under the conditions of 30 cycles of 10 seconds at 98° C., 30 seconds at 60° C., and 3 minutes and 20 seconds at 72° C. Then, this PCR product was cloned between the SbfI and PspOMI restriction sites of the pCLS09G1 vector to prepare the pCLS09G1g1 vector.

Preparation of pCLS09G1t2 Vector

For preparation of the pCLS09G1t2 vector by inserting CSP-B 3'-SAR between the PspOMI and SfiI restriction sites of the pCLS09G1t1 vector, the following experiment was conducted. First, PCR was performed using the cs3sPsp2F primer (aattg ggccc ggatc ccatt ctcct tgatg tacta at; SEQ ID NO: 32) and the cs3sSfi2R primer (aattg gccat gatgg ccgaa ttcaa acaac tcaat agcaa gaaac; SEQ ID NO: 33) while using the pGEMT-CS3S.1.2k vector as a template, to amplify CSP-B 3'-SAR. The PCR was performed under the conditions of 30 cycles of 10 seconds at 98° C., 30 seconds at 60° C., and 2 minutes and 30 seconds at 72° C. Then, this PCR product was cloned between the PspOMI and SfiI restriction sites of the pCLS09G1t1 vector to prepare the pCLS09G1t2 vector.

Preparation of pCLS09G1f2 Vector

For preparation of the pCLS09G1f2 vector by inserting CSP-B 5'-SAR between the PspOMI and SfiI restriction sites of the pCLS09G1f1 vector, the following experiment was conducted. First, PCR was performed using the cs5sPsp2F primer (aattg ggccc gaatt cctaa acaga gcaat taggt aag; SEQ ID NO: 34) and the cs5sSfi2R primer (aattg gccat gatgg ccgaa ttcca gtgta aacgt cttcc ttgt; SEQ ID NO: 35) while using the pGEMT-CS5S.3.0k vector as a template, to amplify CSP-B 5'-SAR. The PCR was performed under the conditions of 30 cycles of 10 seconds at 98° C., 30 seconds at 60° C., and 2 minutes and 30 seconds at 72° C. Then, this PCR product was cloned between the PspOMI and SfiI restriction sites of the pCLS09G1f1 vector to prepare the pCLS09G1f2 vector.

Preparation of pCLS09G1tf Vector

For preparation of the pCLS09G1tf vector by inserting CSP-B 5'-SAR between the PspOMI and SfiI restriction sites of the pCLS09G1t1 vector, the following experiment was conducted. First, PCR was performed using the cs5sPsp2F primer (aattg ggccc gaatt cctaa acaga gcaat taggt aag; SEQ ID NO: 34) and the cs5sSfi2R primer (aattg gccat gatgg ccgaa ttcca gtgta aacgt cttcc ttgt; SEQ ID NO: 35) while using the pGEMT-CS5S.3.0k vector as a template, to amplify CSP-B 5'-SAR. The PCR was performed under the conditions of 30 cycles of 10 seconds at 98° C., 30 seconds at 60° C., and 2 minutes and 30 seconds at 72° C. Then, this PCR product was cloned between the PspOMI and SfiI restriction sites of the pCLS09G1t1 vector to prepare the pCLS09G1tf vector.

Preparation of pCLS09G1f3 Vector

For preparation of the pCLS09G1f3 vector by inserting the CSP-B 5'-SAR into the BglII restriction site between the CMV promoter and the bla promoter of the pCLS09G1f2 vector, the following experiment was conducted. First, PCR was performed using the cs5sBgl3F primer (aatta gatct gaatt cctaa acaga gcaat taggt aag; SEQ ID NO: 36) and the cs5sBgl3R primer (aatta gatct gaatt ccagt gtaaa cgtct tcctt gt; SEQ ID NO: 37) while using the pGEMT-CS5S.3.0k vector as a template, to amplify CSP-B 5'-SAR. The PCR was performed under the conditions of 30 cycles of 10 seconds at 98° C., 30 seconds at 60° C., and 2 minutes and 30 seconds at 72° C. Then, this PCR product was cloned into the BglII restriction site of the pCLS09G1f2 vector to prepare the pCLS09G1f3 vector.

Preparation of pCLS09G1f4 Vector

For preparation of the pCLS09G1f4 vector, in which SAR factors are located at both sides of the lac Z and lac Y genes, by inserting CSP-B 5'-SAR into the BglII restriction site between the CMV promoter and the bla promoter of the pCLS09G1f1 vector, the following experiment was conducted. First, PCR was performed using the cs5sBgl3F primer (aatta gatct gaatt cctaa acaga gcaat taggt aag; SEQ ID NO: 36) and the cs5sBgl3R primer (aatta gatct gaatt ccagt gtaaa cgtct tcctt gt; SEQ ID NO: 37) while using the pGEMT-CS5S.3.0k vector as a template, to amplify CSP-B 5'-SAR. The PCR was performed under the conditions of 30 cycles of 10 seconds at 98° C., 30 seconds at 60° C., and 2 minutes and 30 seconds at 72° C. Then, this PCR product was cloned into the BglII restriction site of the pCLS09G1f1 vector to prepare the pCLS09G1f4 vector.

Example 4

β-Galactosidase Expression Using SAR/MAR Factor-Introduced Vector

Transfection Using pCLS09G1, pCLS09G1f1, pCLS09G1t1, or pCLS09G1g1 Vector

In order to verify the effect due to the respective introduction of one copy of CSP-B 5'-SAR, CSP-B 3'-SAR, and β-globin MAR into the vectors, CHO DG44 cells (Invitrogen, Cat. No. 12609) were transfected as follows.

Adhesion culture type DG44 cells were dispensed in a 6-well plate at $4 \times 10^5$ cells per well. After 24 hours, it was confirmed that cells completely adhered to the plate bottom. 500 μl of the OPTI-MEM® medium (Gibco, Cat. No. 31985-070) was dispensed into each of three sterilized tubes, and then 2 μg of the prepared pCLS09G1, pCLS09G1f1, pCLS09G1t1, or pCLS09G1g1 vectors were mixed therewith, followed by mild pipetting. 500 μl of the OPTI-MEM® medium was dispensed into each of three sterilized tubes. 10 μl of LIPOFECTAMINE® 2000 (Invitrogen, Cat. No. 11668-027) was mixed therewith, followed by mild pipetting, and then left for 5 minutes at room temperature. DNA and a reagent solution were mixed, and then left at room temperature for 20 minutes. This mixture was put into wells of a 6-well plate prepared for each DNA, followed by well mixing.

Verification on β-Galactosidase Activity of Cell Pool Transfected with pCLS09G1, pCLS09G1f1, pCLS09G1t1, or pCLS09G1g1

DG44 cells were transfected with the pCLS09G1, pCLS09G1f1, pCLS09G1t1, or pCLS09G1g1 vector. After 24 hours, the medium was exchanged with a medium containing 10% FBS and 500 μg/ml of GENETICIN®. Medium exchange was performed every three or four days, and the cells were cultured under the conditions of 37° C. and 5% CO$_2$ for three weeks, thereby preparing a stable cell pool.

Figure 7:
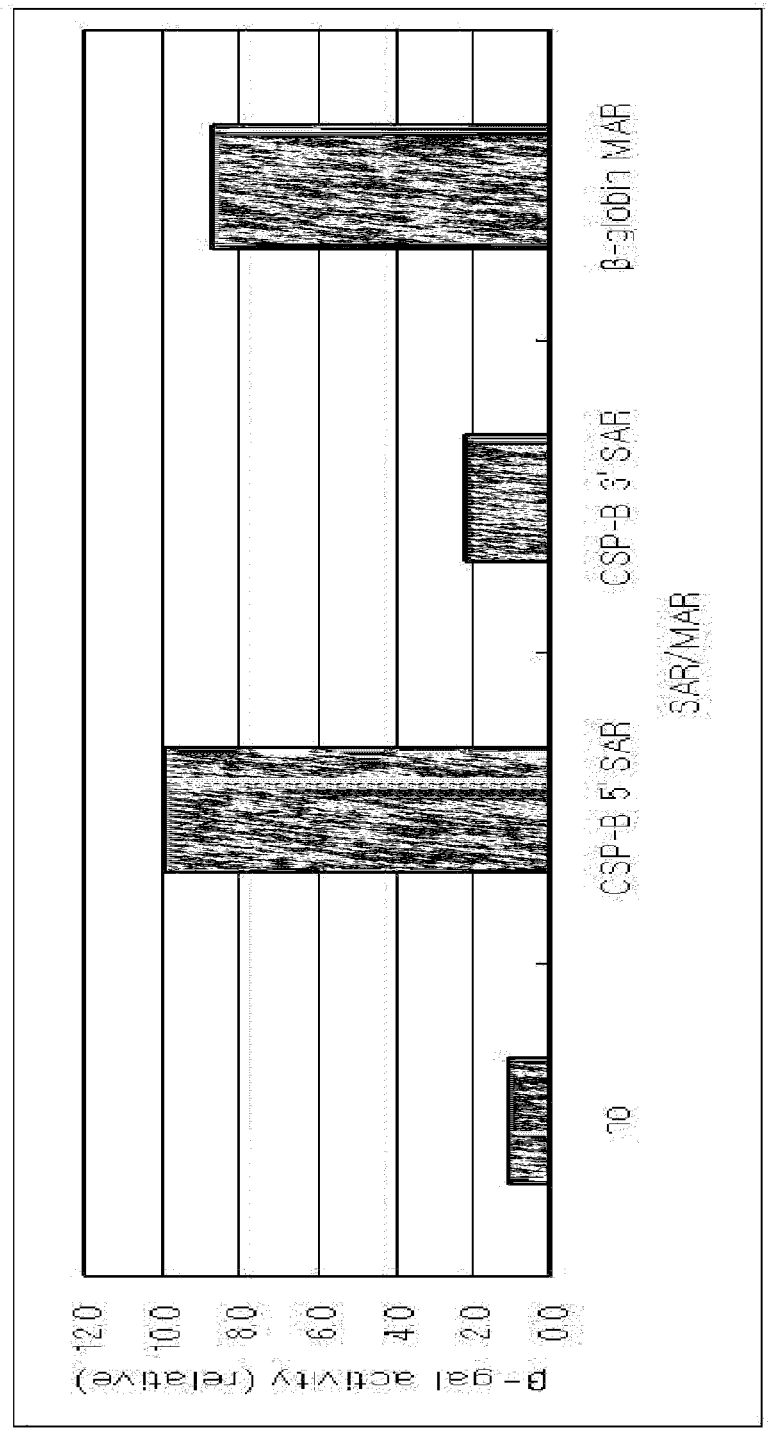
FIG. 7 is a graph showing the β-galactosidase activity (relative) of cells transfected with each of vectors including one copy of SAR/MAR factor introduced thereinto.

A β-galactosidase analysis kit (Stratagen, Cat. No. 200383) was used to verify β-galactosidase activity on the stable cells transfected, and then obtain β-galactosidase activities according to vectors and relative β-galactosidase activities based on the pCLS09G1 vector. As shown in Table 1 and FIG. 7, the β-galactosidase activity was increased for the SAR/MAR factor-introduced vectors as compared with the SAR/MAR factor-not-introduced vector. In addition, the pCLS09G1f1 vector including CSP-B 5'-SAR exhibited higher β-galactosidase activity than pCLS09G1g1 including β-globin MAR. Therefore, it is preferable to introduce the CSP-B 5'-SAR into vectors to increase the target protein expression level.

TABLE 1

| Vector used for transfection | Introduced SAR/MAR | β-galactosidase activity (units/mg) | Relative β-galactosidase activity |
|---|---|---|---|
| pCLS09G1 | None | 3.4 | 1.0 |
| pCLS09G1f1 | CSP-B 5'-SAR | 34.3 | 10.0 |
| pCLS09G1t1 | CSP-B 3'-SAR | 7.4 | 2.2 |
| pCLS09G1g1 | P-globin MAR | 29.8 | 8.7 |

Verification on β-Galactosidase Activity of Cell Pool Transfected with pCLS09G1f1, pCLS09G1f2, pCLS09G1f3, or pCLS09G1f4

Figure 8:
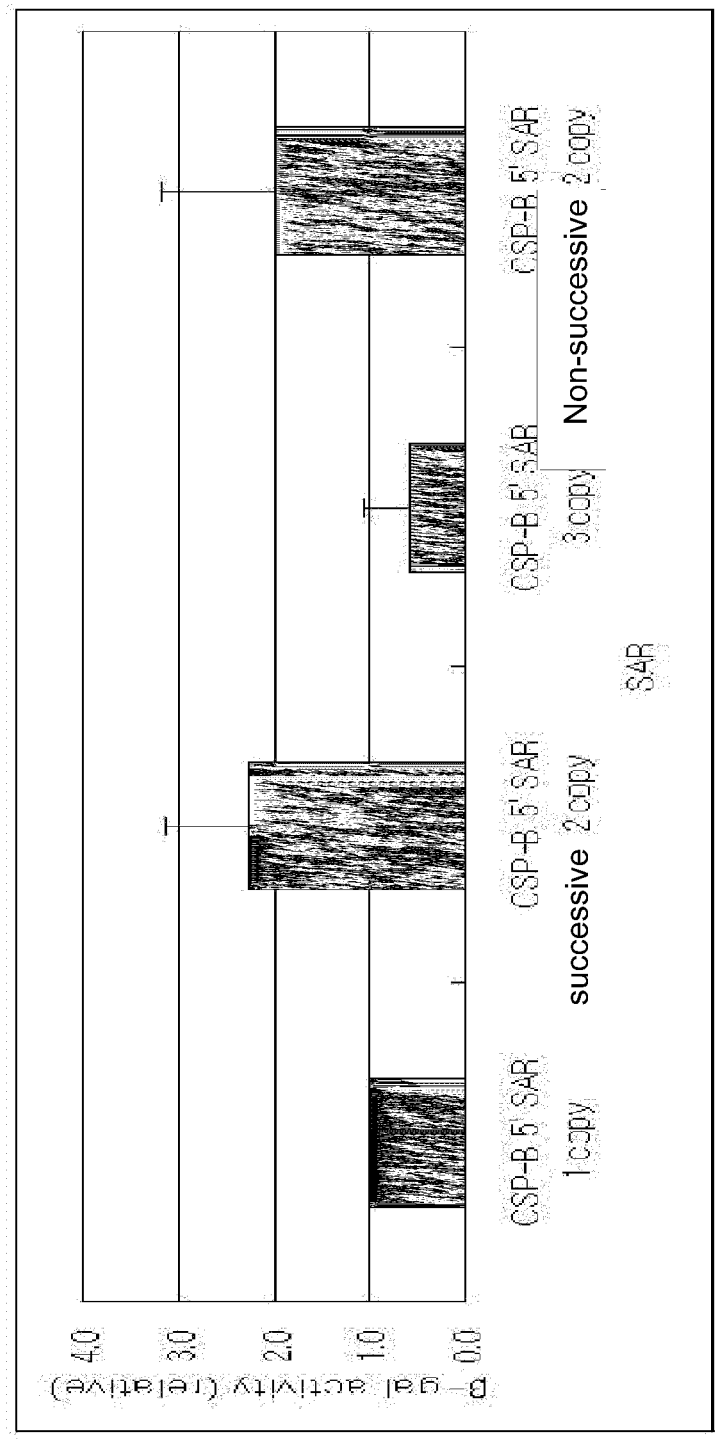
FIG. 8 is a graph showing the β-galactosidase activity (relative) of cells transfected with each of vectors including one copy, two copies, and three copies of SAR factors introduced thereinto.
Figure 9:
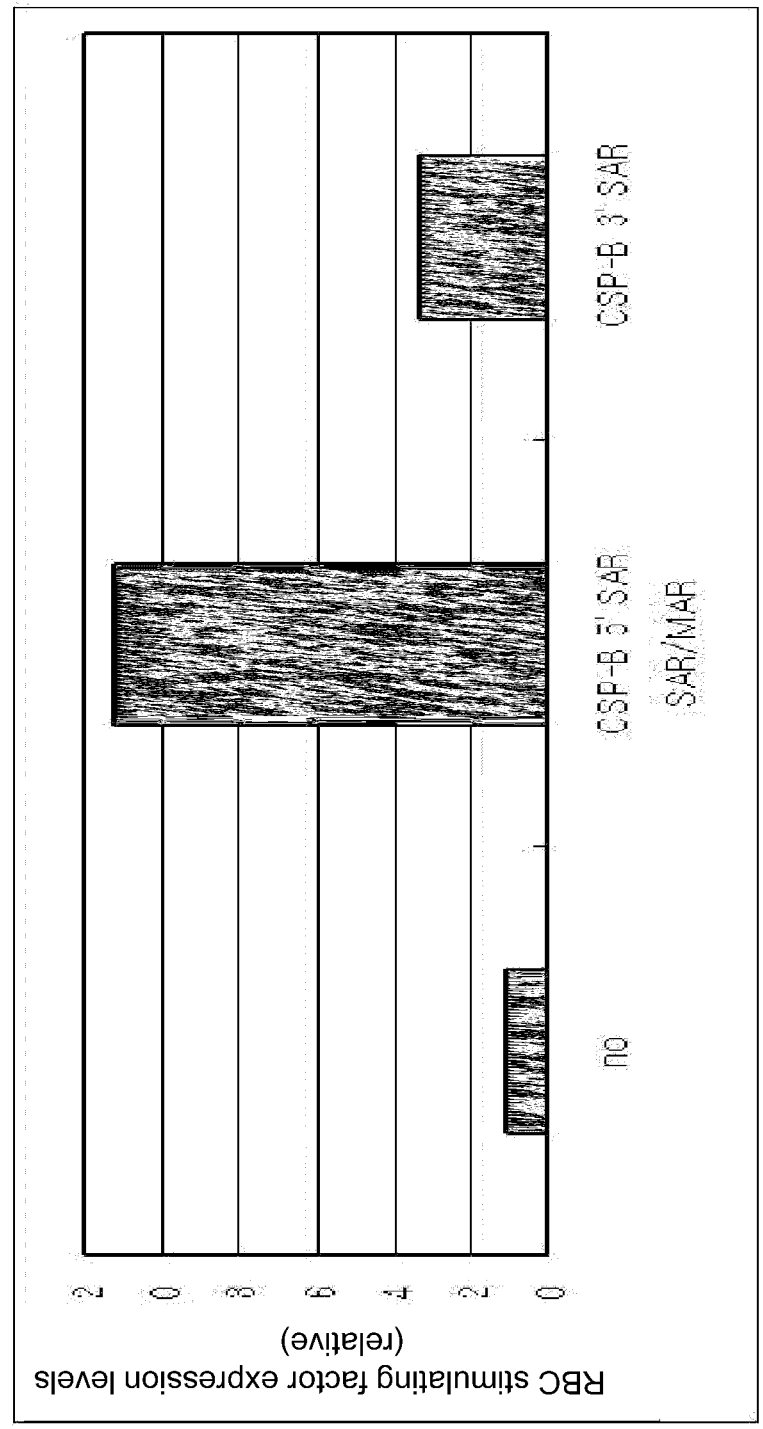
FIG. 9 is a graph showing the NESP (erythropoiesis-stimulating factor) expression level (relative) of cells transfected with each of vectors including SAR factors introduced thereinto.

The following experiment was conducted to verify that the CSP-B 5'-SAR increased the target protein expression levels and investigate the change in the target protein expression level depending on the copy number of SAR factors introduced into the vector. DG44 cells were transfected with the pCLS09G1f1, pCLS09G1f2, pCLS09G1f3, or pCLS09G1f4 vector and then selected with the Geneticin-containing medium, thereby obtaining cell pools. The β-galactosidase activity on the stable cells transfected was verified. The β-galactosidase activities depending on the vectors were obtained. As shown in Table 2 and FIG. 8, the vector including two copies of SAR factors introduced thereinto exhibited higher β-galactosidase activity than the vectors including one copy or three copies of SAR factors introduced thereinto. That is, the increase in the target protein expression levels due to the SAR factor is varied depends on the copy number of SAR factor, and it was verified that the introduction of two copies of SAR factor into vectors can lead to the maximum increase in the target protein expression level.

TABLE 2

| Vector used for transfection | Introduced SAR | β-galactosidase activity (units/mg) | | | | Relative β-galactosidase activity | | | |
|---|---|---|---|---|---|---|---|---|---|
| | | Set 1 | Set 2 | Set 3 | Mean | Set 1 | Set 2 | Set 3 | Mean |
| pCLS09G1f1 | One copy of CSP-B 5'-SAR | 116 | 30 | 50 | 65 | 1.0 | 1.0 | 1.0 | 1.0 |
| pCLS09G1f2 | Continuous two copies of CSP-B 5'-SAR | 147 | 103 | 107 | 119 | 1.3 | 3.4 | 2.1 | 2.3 |
| pCLS09G1f3 | Three copies of CSP-B 5'-SAR | 12 | 36 | 19 | 22 | 0.1 | 1.2 | 0.4 | 0.6 |
| pCLS09G1f4 | Non-continuous two copies of CSP-B 5'-SAR | 112 | 112 | 66 | 97 | 1.0 | 3.7 | 1.3 | 2.0 |

Example 5

Preparation of NESP Expression Vector

Preparation of Erythropoietin Gene

For the cloning of the 582-bp erythropoietin gene registered as GenBank Accession #M11319 (human fetal liver genomic erythropoietin gene) and GenBank Accession #NM000799 (human erythropoietin mRNA), the following experiment was conducted. First, PCR was performed using the IE1 ATGF primer (atggg ggtgc acgaa tgtcc tgcct; SEQ ID NO: 38) and the 1E1TGAR primer (tcatc tgtcc cctgt cctgc aggcc t; SEQ ID NO: 39) while using the Human liver MARATHON®-Ready cDNA library (BD, Cat. No. 7407-1) as a template. The PCR was performed under the conditions of 40 cycles of 10 seconds at 98° C., 30 seconds at 58° C., and 1 minute at 72° C. Then, this PCR product was cloned into the PGEM-T® vector.

Preparation of NESP Gene

For preparation of genes of erythropoietin analogs, NESPs (A30N, H32T, P87V, W88N, and P90T), as described in claim 3 of Korean Patent Application No. 1995-0701453, the following experiment was conducted. First, for preparation of genes of erythropoietin analogs A30N and H32T, PCR was performed using the M13R primer (gaaac agcta tgacc atg; SEQ ID NO: 40) and the IA1g1R primer (ctcat tcaag ctgca tgttt catta cagcc cgtcg tgat; SEQ ID NO: 41) and PCR was performed using the M13F primer (caggg ttttc ccagt cacga; SEQ ID NO: 42) and the IA1g1F primer (atcac gacgg gctgt aatga aacat gcagc ttgaa tgag; SEQ ID NO: 43), while using the erythropoietin gene cloned into the pGEM-T vector as a template. The PCRs were performed under the conditions of 30 cycles of 10 seconds at 98° C., 30 seconds at 60° C., and 40 seconds at 72° C. Then, these two PCR products were ligated through overlapping PCR, and then cloned between the NdeI and SphI restriction sites of the pGEM-T vector.

In order to mutate the genes of the analogs A30N and H32T into genes of the analogs A30N, H32T, P87V, W88N, and P90T and attach the Kozak sequence (gccacc) before the transcription initiation codon, PCR was performed using the M13R primer and the IA1G2R primer (cacat gcagc tgcag tgtct cattc acctg ggaag agttg ac; SEQ ID NO: 44) and PCR was performed using the M13F primer and the IA1G2F primer (gtcaa ctctt cccag gtgaa tgaga cactg cagct gcatg tg; SEQ ID NO: 45), while using the genes of the analogs, A30N and H32T, cloned into the pGEM-T vector as a template. The PCRs were performed under the conditions of 30 cycles of 10 seconds at 98° C., 30 seconds at 60° C., and 40 seconds at 72° C. Then, overlapping PCR was performed using the IE1KzATGHinF primer (aatta agctt gccac catgg gggtg cacga atgtc ctgcc t; SEQ ID NO: 46) and the IE1TGAXhoR primer (aattc tcgag tcatc tgtcc cctgt cctgc aggcc t; SEQ ID NO: 47) while using these two PCR products as a template. The PCR was performed under the conditions of 30 cycles of 10 seconds at 98° C., 30 seconds at 60° C., and 50 seconds at 72° C.

Preparation of pCLS07A1 Vector

The PCR product of the NESP genes were cloned between the HindIII and XhoI restriction sites of the MSC of the pCLS07 vector, to prepare the pCLS07A1 vector.

Example 6

Preparation of NESP Expression Vector Including SAR Factor

Preparation of pCLS10A1 Vector

For preparation of the pCLS10A1 vector by inserting MCS for the SAR or MAR factor introduction into the NheI restriction site of the pCLS07A1 vector capable of exhibiting NESP in animal cells, the following experiment was conducted. First, PCR was performed using the NhAsf1F primer (aattg ctagc atata ggcgc gccaa cttga ttagg gtgat ggttc acgta g; SEQ ID NO: 48) and the NhClPaPsf1R primer (aattg ctagc atata atcga ttata tttaa ttaaa tatag ggccc ttgag tgttg ttcca gtttg gaaca aga; SEQ ID NO: 49) while the pcDNA3.1(−) vector as a template, to obtain MCS. The PCR was performed under the conditions of 30 cycles of 10 seconds at 98° C., 30 seconds at 60° C., and 15 seconds at 72° C. This PCR product was cloned into the NheI restriction site of the pCLS07A1 vector to prepare the pCLS10A1.

Preparation of pCLS10A1t1 Vector

For preparation of the pCLS10A1t1 vector by inserting the CSP-B 3'-SAR between the AscI and PspOMI restriction sites of the pCLS10A1 vector, the following experiment was conducted. First, PCR was performed using the cs3sAsc1F primer (aattg gcgcg ccgga tccca ttctc cttga tgtac taat; SEQ ID NO: 50) and the cs3sPsp1R primer (aattg ggccc gaatt caaac aactc aatag caaga aac; SEQ ID NO: 51) while using the PGEMT®-CS3S.1.2K vector as a template, to amplify CSP-B 3'-SAR. The PCR was performed under the conditions of 30 cycles of 10 seconds at 98° C., 30 seconds at 60° C., and 2 minutes and 30 seconds at 72° C. Then, this PCR product was cloned between the AscI and PspOMI restriction sites of the pCLS10A1 vector to prepare the pCLS10A1 t1 vector.

Preparation of pCLS10A1f1 Vector

For preparation of the pCLS10A1f1 vector by inserting the CSP-B 5'-SAR between the AscI and PspOMI restriction sites of the pCLS10A1 vector, the following experiment was conducted. First, PCR was performed using the cs5sAsc1F primer (aattg gcgcg ccgaa ttcct aaaca gagca attag gtaag; SEQ ID NO: 52) and the cs5sPsp1R primer (aattg ggccc gaatt ccagt gtaaa cgtct tcctt gt; SEQ ID NO: 53) while using the PGEM-T®CS5S.3.0.K vector as a template, to amplify the CSP-B 5'-SAR. The PCR was performed under the conditions of 30 cycles of 10 seconds at 98° C., 30 seconds at 60° C., and 2 minutes and 30 seconds at 72° C. Then, this PCR product was cloned between the AscI and PspOMI restriction sites of the pCLS10A1 vector to prepare the pCLS10A1f1 vector.

Example 7

NESP Expression Using SAR Factor-Introduced Vector

Verification on NESP Expression Level of DG44 Cell Pool Transfected with pCLS07A1, pCLS10A1f1, or pCLS10A1t1

In order to verify whether the effect of the SAR factor, which was confirmed through the β-galactosidase activity experiment, is also applied to expressions of other recombinant proteins, the following experiment was conducted. DG44 cells were transfected with the pCLS07A1, pCLS10A1f1, or pCLS10A1t1 vector including the target protein NESP and the SAR factor, and selected with the GENETICIN®-containing medium, thereby obtaining a cell pool. The NESP expression level was verified by enzyme-linked immunosorbent assay (ELISA). As shown in Table 3 and FIG. 9, it was verified that the introduction of the SAR factor increased the expression level. In particular, the NESP expression level was increased by 11.2 fold when CSP-B 5'-SAR was introduced downstream of the NESP gene than when CSP-B 5'-SAR was not introduced.

TABLE 3

| Vector used for transfection | Introduced SAR/MAR | NESP expression level (μg/Ml) | Relative NESP expression level |
|---|---|---|---|
| pCLS07A1 | None | 0.7 | 1.0 |
| pCLS10A1f1 | CSP-B 5'-SAR | 7.9 | 11.2 |
| pCLS10A1t1 | CSP-B 3'-SAR | 2.3 | 3.2 |

Verification on Frequency of Formation of Positive Clones Expressing NESP

In order to verify effects of the SAR factor of overcoming gene expression suppression depending on positions of foreign genes, DG44 cells were transfected with the pCLS07A1, pCLS10A1t1, or pCLS10A1f1 vector, and single colonies were created by using a 96-well plate. The colony formation frequency for each vector was confirmed through microscopic observation. The culture liquid was taken up and the expression level of NESP was measured, thereby obtaining the frequency of formation of positive clones expressing NESP for each vector. As shown in Tables 4 and 5, 82% of colony formation frequency was shown when the SAR factor was not introduced, and 90% and 50% of wells showed colony formation for the introductions of CSP-B 5'-SAR and CSP-B 3'-SAR, respectively. Further, the frequency of positive clones was approximately 40% for non-introduction of SAR factors and the introduction of CSP-B 3'-SAR, and increased to 59% for the introduction of CSP-B 5'-SAR. That is, it can be verified that the introduction of CSP-B 5'-SAR overcome gene expression suppression depending on positions of foreign genes and thus more clones expressing the target protein NESP were formed.

TABLE 4

| Vector used for transfection | Introduced SAR/MAR | Total number of wells | Number of colony-forming wells | Colony formation frequency (%) |
|---|---|---|---|---|
| pCLS07A1 | None | 240 | 197 | 82 |
| pCLS10A1f1 | CSP-B 5'-SAR | 240 | 217 | 90 |

TABLE 4-continued

| Vector used for transfection | Introduced SAR/MAR | Total number of wells | Number of colony-forming wells | Colony formation frequency (%) |
|---|---|---|---|---|
| pCLS10A1t1 | CSP-B 3'-SAR | 240 | 119 | 50 |

TABLE 5

| Vector used for transfection | Introduced SAR/MAR | Total number of colonies | Number of Positive clones | Frequency of positive clones (%) |
|---|---|---|---|---|
| pCLS07A1 | None | 197 | 89 | 45 |
| pCLS10A1f1 | CSP-B 5'-SAR | 217 | 127 | 59 |
| pCLS10A1t1 | CSP-B 3'-SAR | 119 | 51 | 43 |

Verification on NESP Expression Level of Single Clone

Figure 10:
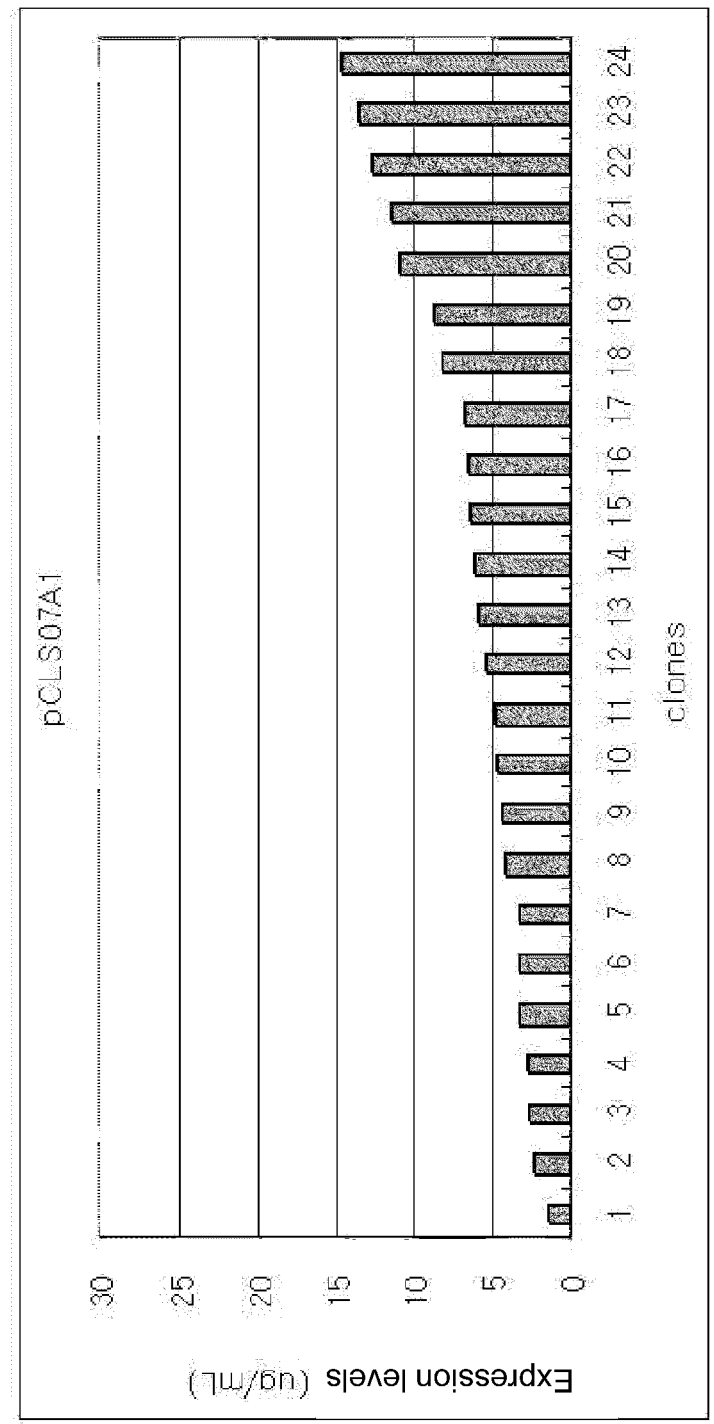
FIG. 10 is a graph showing NESP expression levels of 24 clones randomly selected from cells transfected with the SAR factor-not-introduced pCLS07A1 vector.
Figure 11:
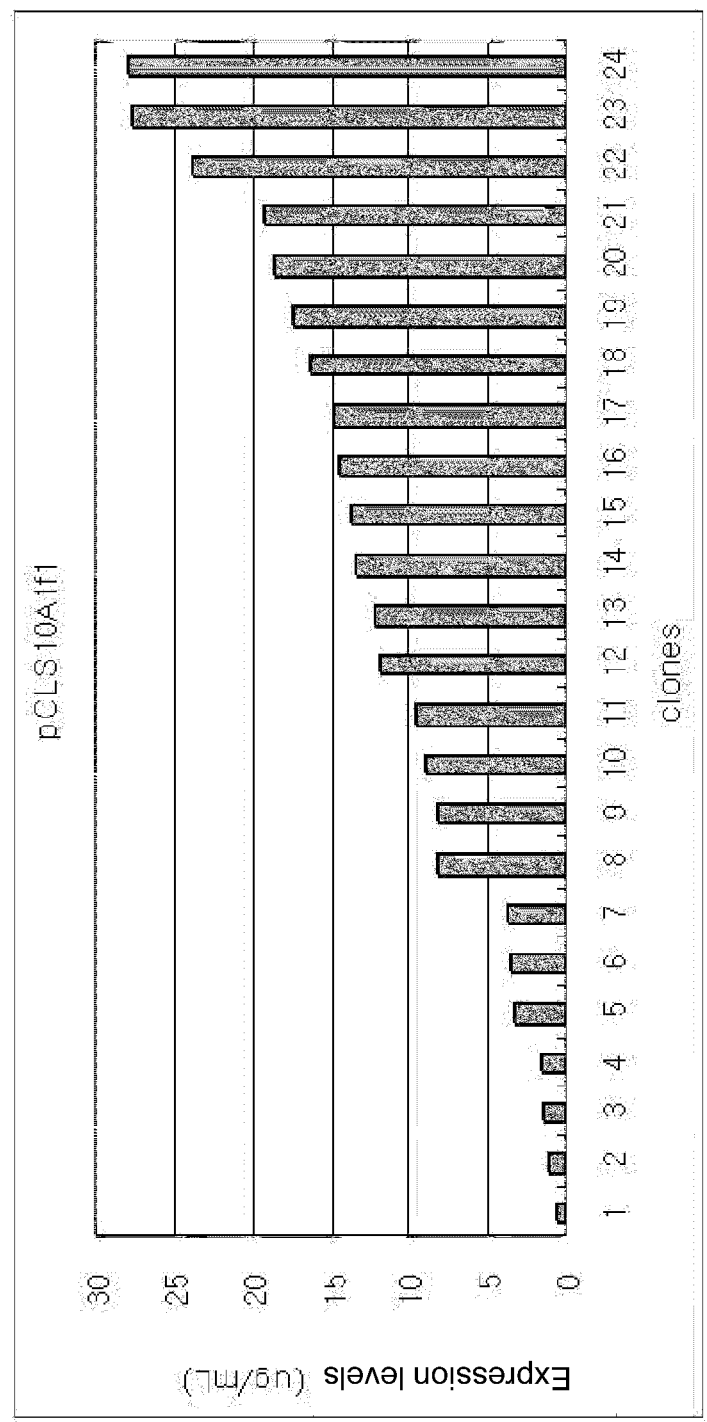
FIG. 11 is a graph showing NESP expression levels of 24 clones randomly selected from cells transfected with the pCLS10A1f1 vector including CSP-B 5'-SAR introduced thereinto.

Among positive clones on the 96-well plate, of which NESP expression was confirmed, 24 positive clones were arbitrarily selected for each vector and subcultured in a 24-well plate. The culture liquid was taken up and the expression level was measured. As shown in FIGS. 10 and 11, the number of high-expression clones that exhibited an expression level of 10 μg/Ml or higher among 24 arbitrarily selected positive clones was 13 for the CSP-B 5'-SAR-introduced vector and 5 for the SAR factor-not introduced vector. That is, it was verified that the frequency of high-expression clones increased when CSP-B 5'-SAR was introduced into the vector.

Example 8

Preparation of Anti-HER2 Expression Vector

Preparation of pC01 Vector

For preparation of the pC01 vector sequentially including a neomycin-resistant gene, an ampicillin-resistant gene, a CMV promoter, MCS, and BGH pA, the following experiment was conducted. First, PCR was performed using the V1_F primer (aagct tcctc agcat cgatg gccgg ccgga tcct gtgcc ttcta gttgc cagcc atctg t; SEQ ID NO: 54) and the V1_R primer (tagag cccca gctgg ttctt tccgc ctcag; SEQ ID NO: 55) while using the pcDNA3.1(−) vector as a template. The PCR was performed under the conditions of 30 cycles of 10 seconds at 98° C., 30 seconds at 60° C., and 1 minute at 72° C. Then, this PCR product was cloned into the pcDNA3.3-TOPO vector to prepare the pC01 vector.

Preparation of pC02 Vector

For preparation of the pC02 vector sequentially including a CMV promoter, the MCS of the pC01 vector and another MCS, and BGH pA, the following experiment was conducted. First, PCR was performed using the V2_F primer (gaatt ctgta caggt acccc tgcag gctcg agctg tgcct tctag ttgcc agcca tctgt; SEQ ID NO: 56) and the V2_R primer (tagag cccca gctgg ttctt tccgc ctcag; SEQ ID NO: 57) while using the pcDNA3.1(−) vector as a template. The PCR was performed under the conditions of 30 cycles of 10 seconds at 98° C., 30 seconds at 60° C., and 1 minute at 72° C. Then, this PCR product was cloned into the pcDNA3.3-TOPO vector to prepare the pC02 vector.

Preparation of pC03 Vector

For preparation of the pC03 vector sequentially including the neomycin-resistant gene, the ampicillin-resistant gene, the CMV promoter, the first MCS, and the BGH pA of the pC01 vector and the CMV promoter, the second MCS, and the BGH pA of the pC02 vector, the following experiment was conducted. First, the pC01 vector was digested with restriction enzymes DraIII and AgeI, thereby obtaining a large DNA fragment. Then, PCR was performed using the PcmvAgeF primer (aatct gaccg gtgtt aggcg ttttg cgctg cttcg cg; SEQ ID NO: 58) and the BGHNheDraR primer (ttact acact acgtg gatcg agcta gctag agccc cagct ggttc tttcc g; SEQ ID NO: 59) while using the pC02 vector as a template. This PCR product was digested with restriction enzymes DraIII and AgeI. The PCR was performed under the conditions of 30 cycles of 10 seconds at 98° C., 30 seconds at 60° C., and 1 minute at 72° C. Last, this PCR product was ligated to the DNA fragment obtained by digesting the pC01 vector with restriction enzymes DraIII and AgeI, thereby preparing the pC03 vector.

Preparation of pCLS05 Vector

For preparation of the pCLS05 vector including the SV40dE1 promoter, the Kozak sequence, the DHFR sequence, and TK pA inserted between the BGH pA and the SV40 promoter of the 140pC03 vector, the following experiment was conducted. First, PCR was performed using the PsvApaDraF primer and the TKNheNdeR primer while using the pC04 vector as a template. The PCR was performed under the conditions of 30 cycles of 10 seconds at 98° C., 30 seconds at 60° C., and 1 minute and 30 seconds at 72° C. Then, this PCR product and the pC03 vector were digested with restriction enzymes DraIII and NheI, and the thus obtained two large DNA fragments are ligated to prepare the pCLS05 vector.

Preparation of pCLS05H1 Vector

For preparation of the pCLS05H1 vector by inserting the anti-HER2 antibody heavy chain gene between EcoRI and XhoI restriction sites of the pCLS05 vector, the following experiment was conducted. First, PCR was performed using the H1ssF primer (ctctt cttgg tagca acagc tacag gtgtc cactc cgagg tccaa ctggt cgaaa gcggt gga; SEQ ID NO: 60) and the H1TGAXhoR primer (aattc tcgag tcatt taccc ggaga caggg agagg ctctt; SEQ ID NO: 61) while using the synthesized anti-HER2 antibody gene as a template, to amplify a heavy chain gene having a part of the signal sequence. PCR was performed using the H1ssEcoF primer (aattg aattc gccac catgg gatgg agctg tatca tcctc ttctt ggtag caaca gctac agg; SEQ ID NO: 62) and the H1TGAXhoR primer (SEQ ID NO: 61) while using this PCR product as a template, to amplify a heavy chain gene having the Kozak sequence and the signal sequence. The PCR was performed under the conditions of 30 cycles of 10 seconds at 98° C., 30 seconds at 60° C., and 1 minute and 30 seconds at 72° C. Then, this PCR product was cloned into the PGEM-T® vector and then digested with restriction enzymes EcoRI and XhoI, to obtain the heavy chain gene having the Kozak sequence and the signal sequence, which was then cloned between the EcoRI and XhoI restriction sites of the pCLS05 vector, thereby preparing the pCLS05H1 vector.

Preparation of pCLS05H2 Vector

Figure 12A:
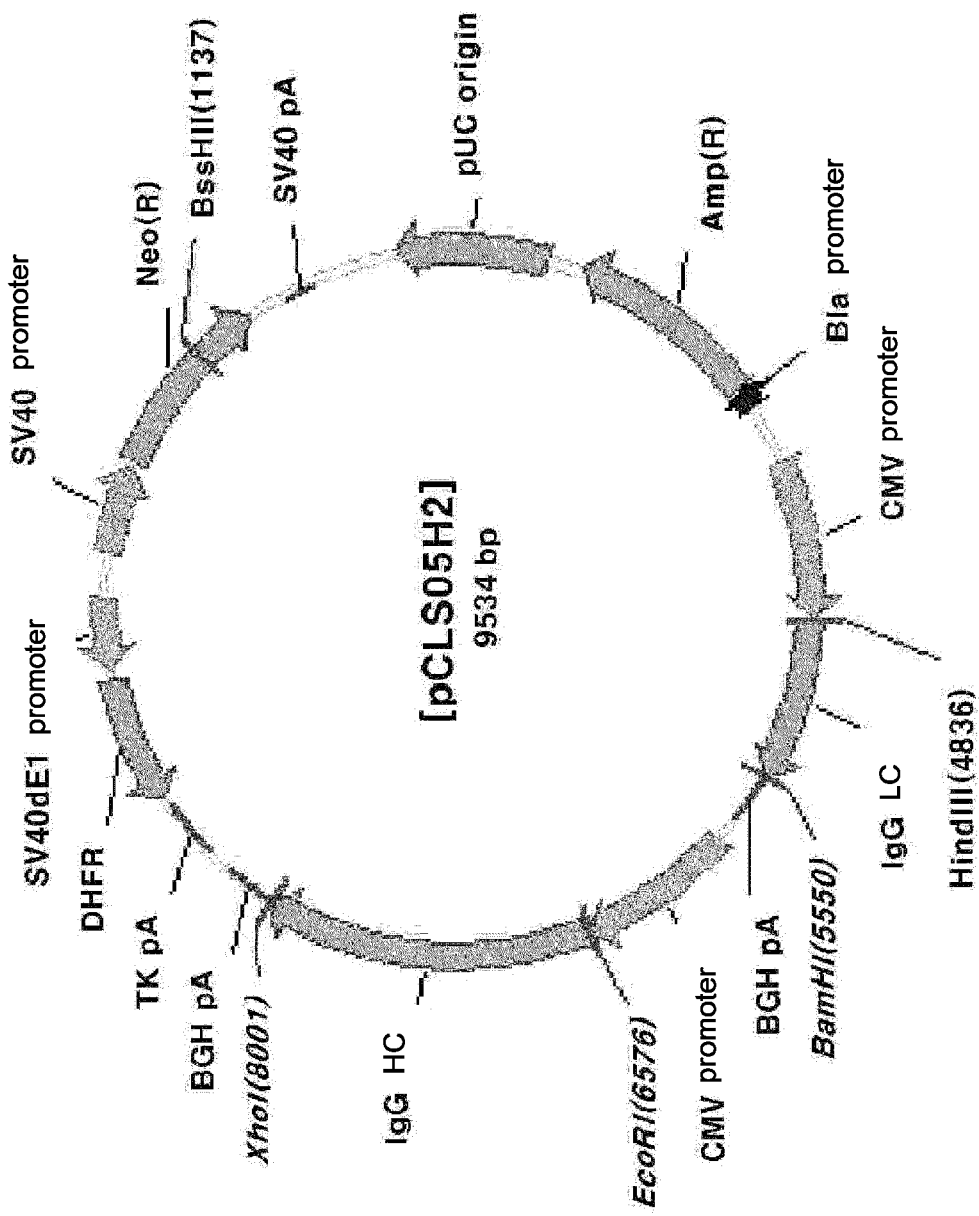
FIGS. 12a-12b schematically show two (a and b) structures of anti-HER2 antibody expression vectors.

For preparation of the pCLS05H2 vector by inserting the anti-HER2 antibody light chain gene between HindIII and BamHI restriction sites of the pCLS05H1 vector, the following experiment was conducted. First, PCR was performed using H2ssF primer (ctctt cttgg tagca acagc tacag gtgtc cactc cgata tccag atgac ccaga gtccc tct; SEQ ID NO: 63) and the H2TGABamR primer (aattg gatcc tcaac actct cccct gttga agctc tttgt; SEQ ID NO: 64) while using the synthesized anti-HER2 gene as a template, to amplify a light chain gene having a part of the signal sequence. PCR was performed using the H2ssHinF primer (aatta agctt gccac catgg gatgg agctg tatca tcctc ttctt ggtag caaca gctac agg; SEQ ID NO: 65)

and the H2TGABamR primer (SEQ ID NO: 64) while using this PCR product as a template, to amplify a light chain gene having the Kozak sequence and the signal sequence. The PCR was performed under the conditions of 30 cycles of 10 seconds at 98° C., 30 seconds at 60° C., and 1 minute at 72° C. Then, this PCR product was cloned into the pGEM-T vector and then digested with restriction enzymes HindIII and BamHI, to obtain a light chain gene having the Kozak sequence and the signal sequence, which was then cloned between the HindIII and BamHI restriction sites of the pCLS05H1 vector, thereby preparing the pCLS05H2 vector. The map of the pCLS05H2 vector is shown in FIG. 12a.

Example 9

Preparation of Anti-HER2 Expression Vector Including SAR Factor

Preparation of pCLS05H2f2 Vector

Figure 12B:
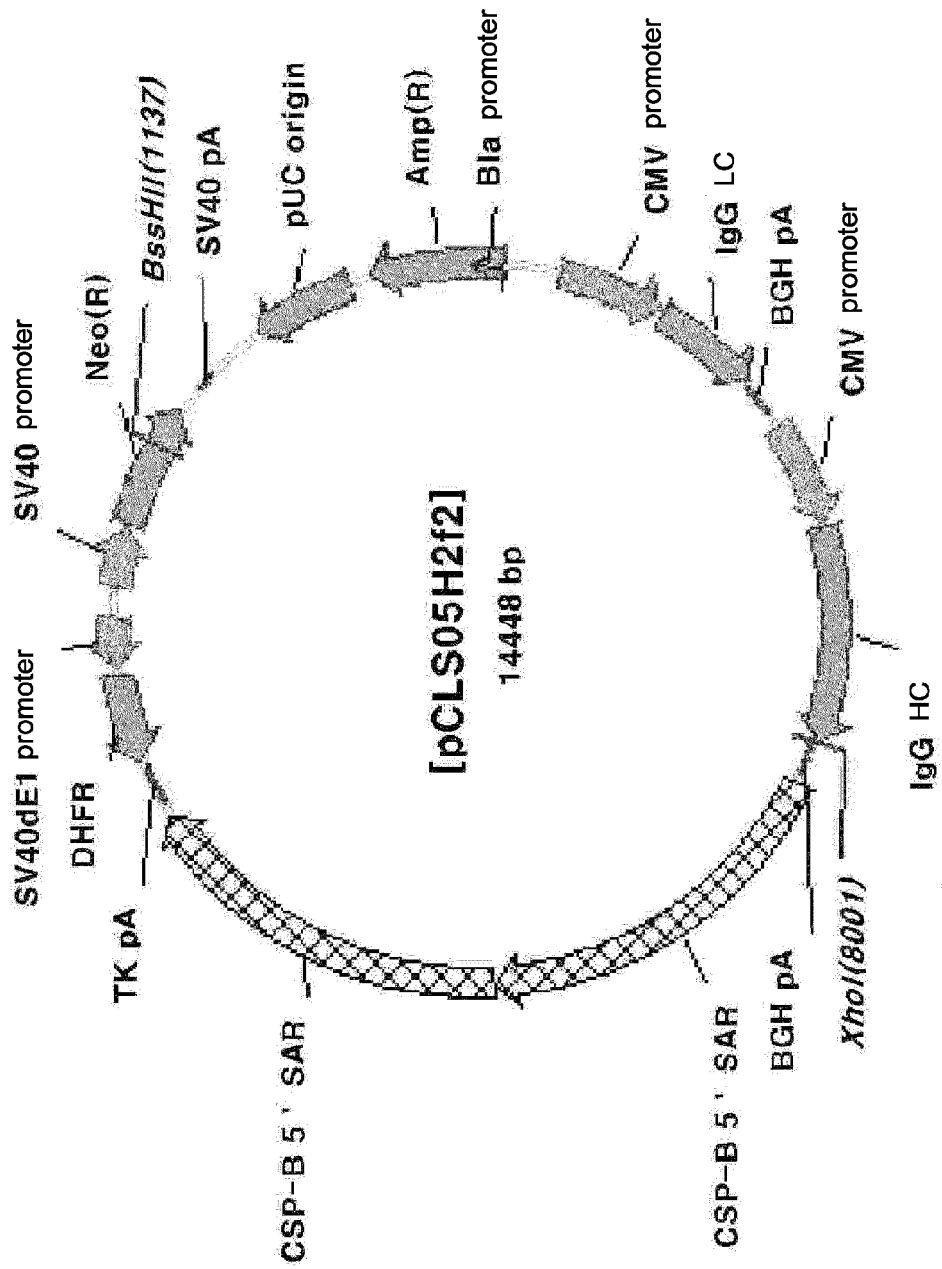

For preparation of the pCLS05H2f2 vector by introducing two copies of CSP-B 5'-SAR between the heavy chain gene and the DHFR gene of the pCLS05H2 vector that can express the anti-HER2 antibody in animal cells, the following experiment was conducted. The pCLS05H2 vector and the pCLS09G1f2 vector were digested with restriction enzymes XhoI and BssHII, and the thus obtained two large DNA fragments were ligated to prepare the pCLS05H2f2 vector. The map of the pCLS05H2f2 vector is shown in FIG. 12b.

Example 10

Anti-HER2 Antibody Expression Using SAR Factor-Introduced Vector

Figure 13:
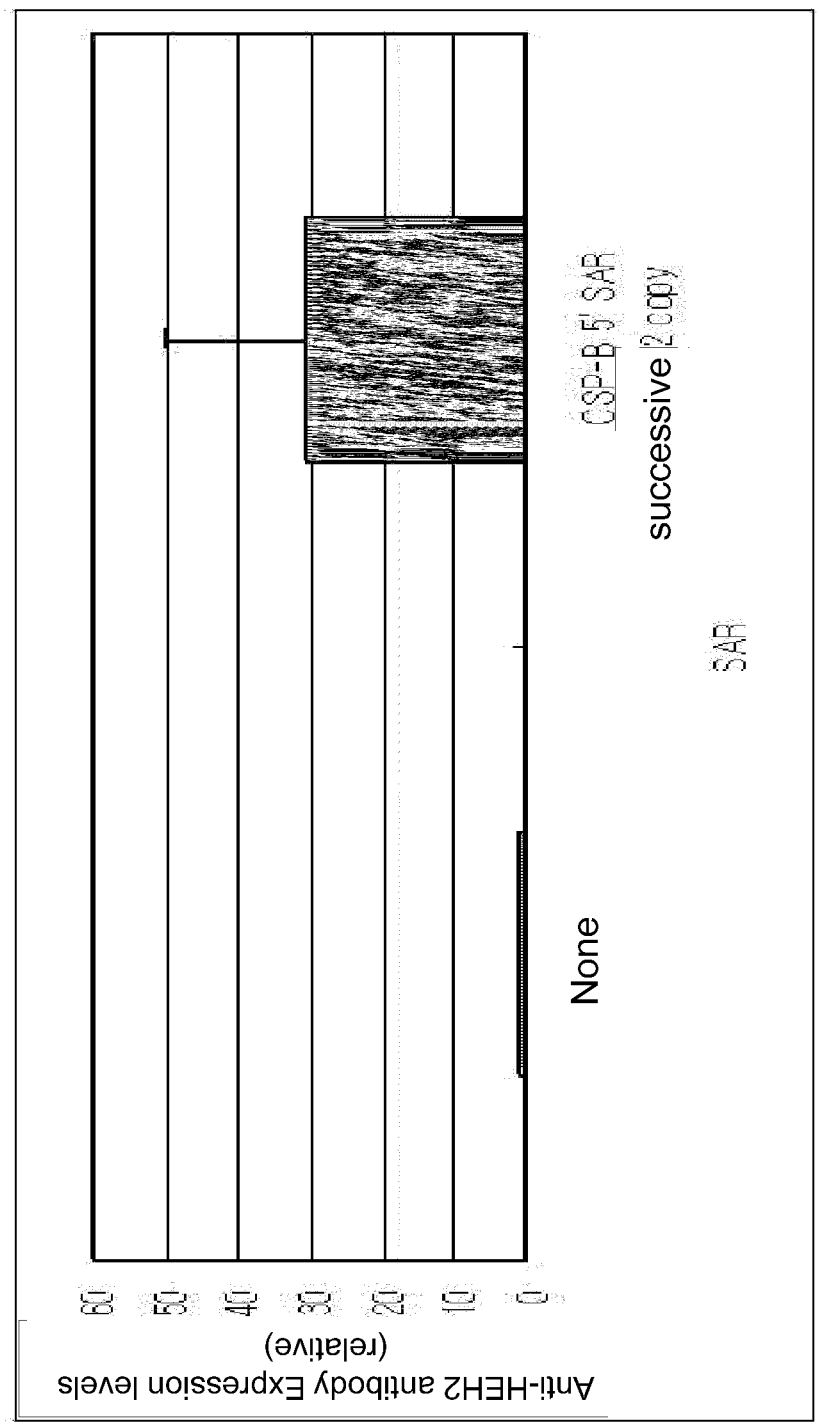
FIG. 13 is a graph showing the anti-HER2 antibody expression level (relative) of cells transfected with the vector including two copies of SAR factors introduced thereinto.

Verification on Anti-HER2 Antibody Expression Level of DG44 Cell Pool Transfected with pCLS05H2 or pCLS05H2f2 Vector DG44 cells were transfected with the pCLS05H2 vector including a gene of the target protein anti-HER2 antibody and the pCLS05H2f2 vector including the antibody gene and the SAR factor, respectively, and then selected with GENETICIN®-containing medium, to obtain cell pools. The anti-HER2 antibody expression levels for the respective vectors were verified by enzyme-linked immunosorbent assay (ELISA). As shown in Table 6 and FIG. 13, it was confirmed that the anti-HER2 antibody expression level was 30-fold higher when two copies of SAR factors were introduced than when the SAR factor was not introduced. The GENETICIN® resistance was exhibited and the surviving cells were relatively more numerous when the pCLS05H2f2 vector including the SAR factor was used.

TABLE 6

| Vector used for transfection | Introduced SAR | Anti-HER2 antibody expression level (μg/Ml) | | | | Relative anti-HER2 antibody expression level | | | |
|---|---|---|---|---|---|---|---|---|---|
| | | Set 1 | Set 2 | Set 3 | Mean | Set 1 | Set 2 | Set 3 | Mean |
| pCLS05H2 | None | 0.29 | 0.50 | 0.26 | 0.35 | 1.0 | 1.0 | 1.0 | 1.0 |
| pCLS05H2f2 | CSP-B Continuous two copies of 5'-SAR | 6.74 | 8.22 | 13.6 | 9.54 | 22.7 | 16.2 | 52.6 | 30.5 |

Verification on Anti-HER2 Antibody Expression Level of Single Clone

Figure 14:
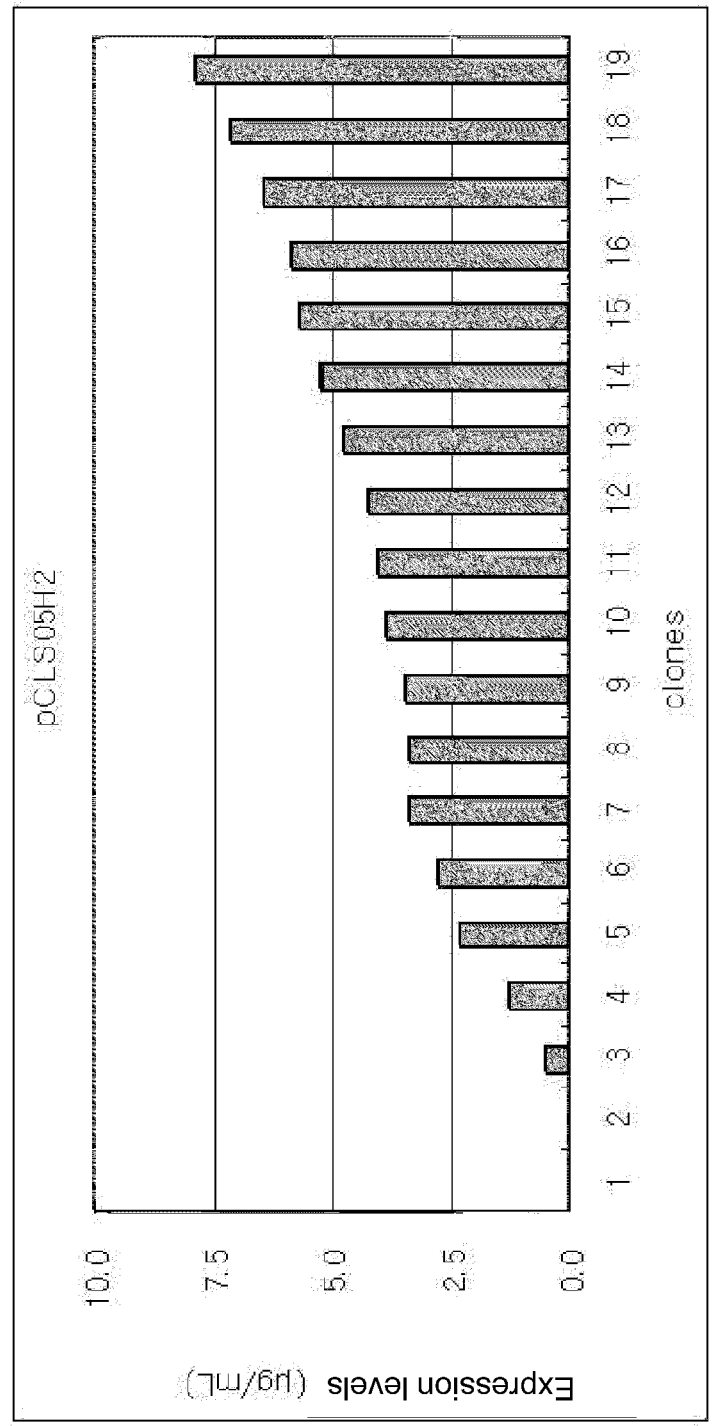
FIG. 14 is a graph showing anti-HER2 antibody expression levels of 19 clones randomly selected from cells transfected with the SAR factor-not-introduced pCLS05H2 vector.
Figure 15:
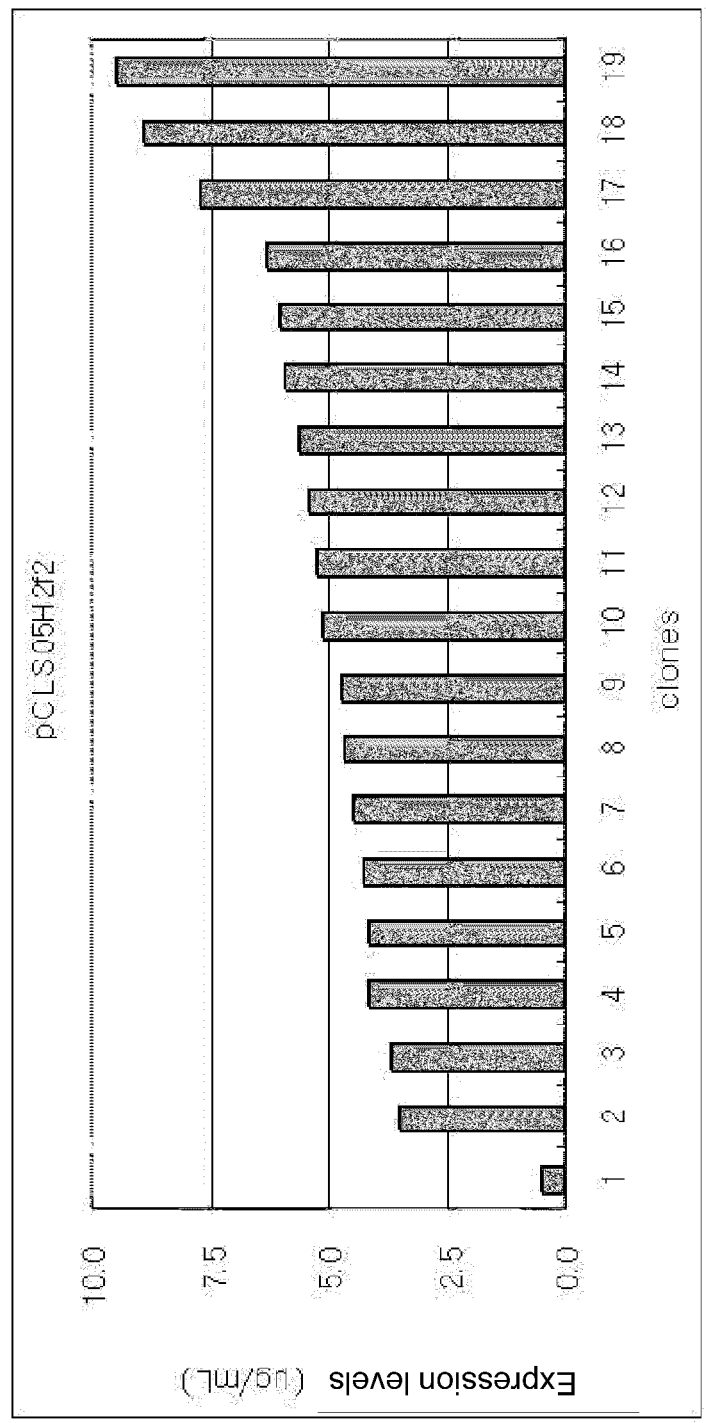
FIG. 15 is a graph showing anti-HER2 antibody expression levels of 19 clones randomly selected from cells transfected with the pCLS05H2f2 vector including two copies of CSP-B 5'-SAR introduced thereinto.

Positive clones on the 96-well plate, of which anti-HER2 antibody expression was confirmed, were arbitrarily selected, and subcultured in a 24-well plate. The culture liquid was taken up and the expression level was measured. As shown in FIGS. 14 and 15, the number of high-expression clones that exhibited an expression level of 5 μg/Ml or higher among 19 arbitrarily selected positive clones was 10 for the vector to which two copies of CSP-B 5'-SAR were introduced and 6 for the vector to which the SAR factor was not introduced. That is, it was verified that the frequency of high-expression clones relatively increased when CSP-B 5'-SAR factor was introduced into the vector.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An expression vector for animal cells, comprising:
   a protein-coding nucleotide sequence to be expressed, wherein the protein is a Novel Erythropoiesis Stimulating Protein (NESP) or an anti-human epidermal growth factor receptor 2 (anti-HER2) antibody;
   a 5'-scaffold attachment region (5'-SAR) of cytotoxic serine protease-B (CSP-B), wherein the 5'-SAR is present in two copies downstream of the protein-coding nucleotide sequence to be expressed, and the two copies of the 5'-SAR are consecutively present in the vector;
   a promoter operable in animal cells; and
   a polyadenylation sequence.

2. The expression vector according to claim 1, wherein the promoter operable in the animal cells is a cytomegalovirus (CMV) promoter, an adenovirus late promoter, a vaccinia virus 7.5K promoter, a Simian virus 40 (SV40) promoter, an SV40E1 promoter, a herpes simplex virus (HSV) tk promoter, a respiratory syncytial virus (RSV) promoter, an elongation factor 1-α (EF1-α) promoter, a metallothionein promoter, a β-actin promoter, a human interleukin-2 (IL-2) gene promoter, a human interferon (IFN) gene promoter, a human IL-4 gene promoter, a human lymphotoxin gene promoter, or a human granulocyte-macrophage colony-stimulating factor (GM-CSF) gene promoter.

3. The expression vector according to claim 1, wherein the polyadenylation sequence is a bovine growth hormone polyadenylation sequence, an HSV thymidine kinase (TK) polyadenylation sequence, or an SV40 polyadenylation sequence.

4. The expression vector according to claim 1, wherein the animal cells are Chinese hamster ovary (CHO) cells, VERO cells, HeLa cells, WI38 cells, baby hamster kidney (BHK) cells, COS cells, or Madin-Darby canine kidney (MDCK) cells.

5. An isolated animal cell transfected with the expression vector according to claim 1.

6. A method for preparing a recombinant protein, comprising incubating the transfected animal cell of claim 5 and expressing the NESP or anti-HER2 antibody.

* * * * *